(12) United States Patent
Quadri et al.

(10) Patent No.: US 11,376,119 B2
(45) Date of Patent: Jul. 5, 2022

(54) VASCULAR IMPLANT AND DELIVERY SYSTEM

(71) Applicant: Edwards Lifesciences CardiAQ LLC, Irvine, CA (US)

(72) Inventors: Arshad Quadri, West Hartford, CT (US); J. Brent Ratz, Winchester, MA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 449 days.

(21) Appl. No.: 16/601,054

(22) Filed: Oct. 14, 2019

(65) Prior Publication Data

US 2020/0038178 A1    Feb. 6, 2020

Related U.S. Application Data

(63) Continuation of application No. 15/288,693, filed on Oct. 7, 2016, now Pat. No. 10,441,412, which is a (Continued)

(51) Int. Cl.
*A61F 2/24* (2006.01)
*A61F 2/95* (2013.01)

(52) U.S. Cl.
CPC ............ *A61F 2/2409* (2013.01); *A61F 2/243* (2013.01); *A61F 2/2418* (2013.01); (Continued)

(58) Field of Classification Search
CPC ........ A61F 2/2418; A61F 2/2436; A61F 2/24; A61F 2/2409; A61F 2/95; A61F 2/243; (Continued)

(56) References Cited

U.S. PATENT DOCUMENTS 3,657,744 A    4/1972 Ersek
3,671,979 A    6/1972 Moulopoulos
(Continued)

FOREIGN PATENT DOCUMENTS

CA    2304325 A1    10/2000
CA    2827556 A1    7/2012
(Continued)

OTHER PUBLICATIONS

Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
(Continued)

*Primary Examiner* — Phong Son H Dang
(74) *Attorney, Agent, or Firm* — Knobbe Martens Olson & Bear LLP

(57) ABSTRACT

A vascular implant for replacing a native heart valve comprises a self expanding stent supporting a valve body having leaflets. The stent preferably comprises an anchoring structure configured to prevent the implant from passing through the valve annulus. For delivery, the implant is compacted within delivery device and secured at one end. During delivery the implant is partially released from the delivery device, and positioning of the implant can be verified prior to full release. The implant can be at least partially resheathed and repositioned if desired.

20 Claims, 45 Drawing Sheets

Related U.S. Application Data continuation of application No. 14/313,160, filed on Jun. 24, 2014, now Pat. No. 9,585,747, which is a continuation of application No. 13/755,863, filed on Jan. 31, 2013, now Pat. No. 9,339,379, which is a continuation of application No. 12/761,349, filed on Apr. 15, 2010, now Pat. No. 8,414,644.

(60) Provisional application No. 61/169,367, filed on Apr. 15, 2009.

(52) U.S. Cl.
CPC .......... *A61F 2/2436* (2013.01); *A61F 2/2439* (2013.01); *A61F 2/95* (2013.01); *A61F 2/9522* (2020.05); *A61F 2002/9534* (2013.01); *A61F 2220/0016* (2013.01); *A61F 2220/0033* (2013.01); *A61F 2220/0075* (2013.01); *A61F 2230/0013* (2013.01); *A61F 2250/001* (2013.01)

(58) Field of Classification Search
CPC ............ A61F 2/2439; A61F 2220/0033; A61F 2220/0016; A61F 2220/0075; A61F 2220/001; A61F 2220/0013
See application file for complete search history.

(56) References Cited

U.S. PATENT DOCUMENTS

| | | |
|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,843,167 A * | 12/1998 | Dwyer .................... A61F 2/07 623/1.14 |
| 5,855,601 A * | 1/1999 | Bessler ................. A61F 2/2418 623/2.38 |
| 5,957,949 A * | 9/1999 | Leonhardt ................ A61F 2/07 606/198 |
| 6,077,297 A * | 6/2000 | Robinson ................. A61F 2/95 623/1.11 |
| 6,086,612 A | 7/2000 | Jansen |
| 6,113,612 A * | 9/2000 | Swanson .................. A61F 2/88 623/1.15 |
| 6,113,631 A | 9/2000 | Jansen |
| 6,168,614 B1 | 1/2001 | Andersen et al. |
| 6,251,093 B1 | 6/2001 | Valley et al. |
| 6,280,466 B1 * | 8/2001 | Kugler ................... A61F 2/07 623/1.15 |
| 6,312,465 B1 | 11/2001 | Griffin et al. |
| 6,358,277 B1 | 3/2002 | Duran |
| 6,425,916 B1 * | 7/2002 | Garrison ............... A61F 2/2436 623/2.11 |
| 6,440,164 B1 | 8/2002 | Di Matteo et al. |
| 6,458,153 B1 | 10/2002 | Bailey et al. |
| 6,482,228 B1 | 11/2002 | Norred |
| 6,527,800 B1 * | 3/2003 | McGuckin, Jr ....... A61F 2/2475 623/1.24 |
| 6,582,462 B1 | 6/2003 | Andersen et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,858,034 B1 * | 2/2005 | Hijlkema .................. A61F 2/95 623/1.11 |
| 6,875,231 B2 | 4/2005 | Anduiza et al. |
| 6,893,460 B2 | 5/2005 | Spenser et al. |
| 6,908,481 B2 | 6/2005 | Cribier |
| 6,936,058 B2 * | 8/2005 | Forde ...................... A61F 2/95 606/108 |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,264,632 B2 * | 9/2007 | Wright ..................... A61F 2/95 623/1.11 |
| 7,276,078 B2 | 10/2007 | Spenser et al. |
| 7,329,278 B2 | 2/2008 | Seguin et al. |
| 7,335,218 B2 | 2/2008 | Wilson et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,771,463 B2 * | 8/2010 | Ton .......................... A61F 2/88 623/1.11 |
| 7,803,185 B2 | 9/2010 | Gabbay |
| 7,806,919 B2 | 10/2010 | Bloom et al. |
| 7,815,673 B2 | 10/2010 | Bloom et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 * | 8/2011 | Righini ................. A61F 2/2436 623/2.11 |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |

(56) References Cited

U.S. PATENT DOCUMENTS

| | | | |
|---|---|---|---|
| 8,167,934 B2 | 5/2012 | Styrc et al. | |
| 8,182,528 B2 | 5/2012 | Salahieh et al. | |
| 8,182,530 B2 | 5/2012 | Huber | |
| 8,216,301 B2 | 7/2012 | Bonhoeffer et al. | |
| 8,219,229 B2 | 7/2012 | Cao et al. | |
| 8,220,121 B2 | 7/2012 | Hendriksen et al. | |
| 8,221,493 B2 | 7/2012 | Boyle et al. | |
| 8,226,710 B2 | 7/2012 | Nguyen et al. | |
| 8,236,045 B2 * | 8/2012 | Benichou | A61F 2/2412 623/2.11 |
| 8,246,675 B2 | 8/2012 | Zegdi | |
| 8,246,678 B2 | 8/2012 | Salahieh et al. | |
| 8,252,051 B2 | 8/2012 | Chau et al. | |
| 8,252,052 B2 | 8/2012 | Salahieh et al. | |
| 8,287,584 B2 | 10/2012 | Salahieh et al. | |
| 8,303,653 B2 | 11/2012 | Bonhoeffer et al. | |
| 8,313,525 B2 | 11/2012 | Tuval et al. | |
| 8,323,335 B2 | 12/2012 | Rowe et al. | |
| 8,353,953 B2 | 1/2013 | Giannetti et al. | |
| 8,403,983 B2 | 3/2013 | Quadri et al. | |
| 8,414,644 B2 | 4/2013 | Quadri et al. | |
| 8,414,645 B2 | 4/2013 | Dwork et al. | |
| 8,444,689 B2 | 5/2013 | Zhang | |
| 8,449,599 B2 * | 5/2013 | Chau | A61F 2/246 623/1.26 |
| 8,454,685 B2 | 6/2013 | Hariton et al. | |
| 8,460,368 B2 | 6/2013 | Taylor et al. | |
| 8,470,023 B2 | 6/2013 | Eidenschink et al. | |
| 8,475,521 B2 | 7/2013 | Suri et al. | |
| 8,475,523 B2 | 7/2013 | Duffy | |
| 8,479,380 B2 | 7/2013 | Malewicz et al. | |
| 8,486,137 B2 | 7/2013 | Suri et al. | |
| 8,491,650 B2 | 7/2013 | Wiemeyer et al. | |
| 8,500,733 B2 | 8/2013 | Watson | |
| 8,500,798 B2 | 8/2013 | Rowe et al. | |
| 8,511,244 B2 | 8/2013 | Holecek et al. | |
| 8,512,401 B2 | 8/2013 | Murray, III et al. | |
| 8,518,096 B2 | 8/2013 | Nelson | |
| 8,518,106 B2 | 8/2013 | Duffy et al. | |
| 8,562,663 B2 | 10/2013 | Mearns et al. | |
| 8,579,963 B2 | 11/2013 | Tabor | |
| 8,579,964 B2 | 11/2013 | Lane et al. | |
| 8,579,965 B2 | 11/2013 | Bonhoeffer et al. | |
| 8,585,755 B2 | 11/2013 | Chau et al. | |
| 8,585,756 B2 | 11/2013 | Bonhoeffer et al. | |
| 8,591,570 B2 | 11/2013 | Revuelta et al. | |
| 8,597,348 B2 | 12/2013 | Rowe et al. | |
| 8,617,236 B2 | 12/2013 | Paul et al. | |
| 8,640,521 B2 | 2/2014 | Righini et al. | |
| 8,647,381 B2 | 2/2014 | Essinger et al. | |
| 8,652,145 B2 | 2/2014 | Maimon et al. | |
| 8,652,201 B2 | 2/2014 | Oberti et al. | |
| 8,652,202 B2 | 2/2014 | Alon et al. | |
| 8,652,203 B2 | 2/2014 | Quadri et al. | |
| 8,668,733 B2 | 3/2014 | Haug et al. | |
| 8,673,000 B2 | 3/2014 | Tabor et al. | |
| 8,679,174 B2 | 3/2014 | Ottma et al. | |
| 8,679,404 B2 | 3/2014 | Liburd et al. | |
| 8,685,086 B2 | 4/2014 | Navia et al. | |
| 8,721,708 B2 | 5/2014 | Seguin et al. | |
| 8,721,714 B2 | 5/2014 | Kelley | |
| 8,728,154 B2 | 5/2014 | Alkhatib | |
| 8,728,155 B2 | 5/2014 | Montorfano et al. | |
| 8,740,974 B2 | 6/2014 | Lambrecht et al. | |
| 8,740,976 B2 | 6/2014 | Tran et al. | |
| 8,747,458 B2 | 6/2014 | Tuval et al. | |
| 8,747,459 B2 | 6/2014 | Nguyen et al. | |
| 8,747,460 B2 | 6/2014 | Tuval et al. | |
| 8,758,432 B2 | 6/2014 | Solem | |
| 8,764,818 B2 | 7/2014 | Gregg | |
| 8,771,344 B2 | 7/2014 | Tran et al. | |
| 8,771,345 B2 | 7/2014 | Tuval et al. | |
| 8,771,346 B2 | 7/2014 | Tuval et al. | |
| 8,778,020 B2 | 7/2014 | Gregg et al. | |
| 8,784,337 B2 | 7/2014 | Voeller et al. | |
| 8,784,478 B2 | 7/2014 | Tuval et al. | |
| 8,784,481 B2 | 7/2014 | Alkhatib et al. | |
| 8,790,387 B2 | 7/2014 | Nguyen et al. | |
| 8,795,356 B2 | 8/2014 | Quadri et al. | |
| 8,795,357 B2 | 8/2014 | Yohanan et al. | |
| 8,808,356 B2 | 8/2014 | Braido et al. | |
| 8,828,078 B2 | 9/2014 | Salahieh et al. | |
| 8,828,079 B2 * | 9/2014 | Thielen | A61F 2/2427 623/2.17 |
| 8,834,564 B2 | 9/2014 | Tuval et al. | |
| 8,845,718 B2 | 9/2014 | Tuval et al. | |
| 8,858,620 B2 | 10/2014 | Salahieh et al. | |
| 8,870,948 B1 | 10/2014 | Erzberger et al. | |
| 8,870,950 B2 | 10/2014 | Hacohen | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,911,455 B2 | 12/2014 | Quadri et al. | |
| 8,926,693 B2 | 1/2015 | Duffy et al. | |
| 8,926,694 B2 | 1/2015 | Costello | |
| 8,939,960 B2 | 1/2015 | Rosenman et al. | |
| 8,945,209 B2 | 2/2015 | Bonyuet et al. | |
| 8,951,299 B2 | 2/2015 | Paul et al. | |
| 8,956,404 B2 * | 2/2015 | Bortlein | A61F 2/2418 623/2.11 |
| 8,961,593 B2 | 2/2015 | Bonhoeffer et al. | |
| 8,961,595 B2 | 2/2015 | Alkhatib | |
| 8,974,524 B2 | 3/2015 | Yeung et al. | |
| 8,979,922 B2 | 3/2015 | Jayasinghe et al. | |
| 8,986,372 B2 | 3/2015 | Murry, III et al. | |
| 8,986,375 B2 | 3/2015 | Garde et al. | |
| 8,992,608 B2 | 3/2015 | Haug et al. | |
| 8,998,979 B2 | 4/2015 | Seguin et al. | |
| 8,998,980 B2 | 4/2015 | Shipley et al. | |
| 9,005,273 B2 | 4/2015 | Salahieh et al. | |
| 9,011,521 B2 | 4/2015 | Haug et al. | |
| 9,011,523 B2 | 4/2015 | Seguin | |
| 9,011,524 B2 | 4/2015 | Eberhardt | |
| 9,028,545 B2 | 5/2015 | Taylor | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,055,937 B2 | 6/2015 | Rowe et al. | |
| 9,066,801 B2 | 6/2015 | Kovalsky et al. | |
| 9,078,749 B2 | 7/2015 | Lutter et al. | |
| 9,078,751 B2 | 7/2015 | Naor | |
| 9,084,676 B2 | 7/2015 | Chau et al. | |
| 9,125,738 B2 | 9/2015 | Figulla et al. | |
| 9,138,312 B2 | 9/2015 | Tuval et al. | |
| 9,161,834 B2 | 10/2015 | Taylor et al. | |
| 9,173,737 B2 | 11/2015 | Hill et al. | |
| 9,180,004 B2 | 11/2015 | Alkhatib | |
| 9,186,249 B2 | 11/2015 | Rolando et al. | |
| 9,220,594 B2 | 12/2015 | Braido et al. | |
| 9,241,790 B2 | 1/2016 | Lane et al. | |
| 9,248,014 B2 | 2/2016 | Lane et al. | |
| 9,277,990 B2 | 3/2016 | Klima et al. | |
| 9,277,993 B2 | 3/2016 | Gamarra et al. | |
| 9,289,291 B2 | 3/2016 | Gorman, III et al. | |
| 9,289,296 B2 | 3/2016 | Braido et al. | |
| 9,295,551 B2 | 3/2016 | Straubinger et al. | |
| 9,326,815 B2 | 5/2016 | Watson | |
| 9,331,328 B2 | 5/2016 | Eberhardt et al. | |
| 9,339,382 B2 | 5/2016 | Tabor et al. | |
| 9,351,831 B2 | 5/2016 | Braido et al. | |
| 9,351,832 B2 | 5/2016 | Braido et al. | |
| 9,364,321 B2 | 6/2016 | Alkhatib et al. | |
| 9,445,897 B2 | 9/2016 | Bishop et al. | |
| 9,456,877 B2 | 10/2016 | Weitzner et al. | |
| 9,681,968 B2 | 6/2017 | Goetz et al. | |
| 9,700,329 B2 | 7/2017 | Metzger et al. | |
| 9,700,411 B2 | 7/2017 | Klima et al. | |
| 9,795,479 B2 | 10/2017 | Lim et al. | |
| 9,833,313 B2 | 12/2017 | Board et al. | |
| 9,861,473 B2 | 1/2018 | Lafontaine | |
| 9,861,476 B2 | 1/2018 | Salahieh et al. | |
| 9,861,477 B2 | 1/2018 | Backus et al. | |
| 9,867,698 B2 | 1/2018 | Kovalsky et al. | |
| 9,877,830 B2 | 1/2018 | Lim et al. | |

(56) References Cited

U.S. PATENT DOCUMENTS

| | | | |
|---|---|---|---|
| 9,889,029 B2 | 2/2018 | Li et al. | |
| 9,895,225 B2 | 2/2018 | Rolando et al. | |
| 9,925,045 B2 | 3/2018 | Creaven et al. | |
| 2001/0007956 A1 | 7/2001 | Letac et al. | |
| 2001/0047180 A1* | 11/2001 | Grudem | A61B 17/11 606/153 |
| 2001/0047200 A1* | 11/2001 | White | A61F 2/91 623/1.15 |
| 2002/0016623 A1 | 2/2002 | Kula et al. | |
| 2002/0032481 A1* | 3/2002 | Gabbay | A61F 2/2409 623/2.14 |
| 2002/0045929 A1 | 4/2002 | Diaz | |
| 2002/0052644 A1* | 5/2002 | Shaolian | A61F 2/856 623/1.13 |
| 2003/0105517 A1 | 6/2003 | White et al. | |
| 2003/0120333 A1 | 6/2003 | Ouriel et al. | |
| 2003/0130729 A1 | 7/2003 | Paniagua et al. | |
| 2003/0176914 A1 | 9/2003 | Rabkin et al. | |
| 2003/0199971 A1 | 10/2003 | Tower et al. | |
| 2003/0220683 A1 | 11/2003 | Minasian et al. | |
| 2004/0087900 A1* | 5/2004 | Thompson | A61F 2/915 623/1.11 |
| 2004/0102842 A1* | 5/2004 | Jansen | A61F 2/2412 623/2.38 |
| 2004/0117009 A1 | 6/2004 | Cali et al. | |
| 2004/0133273 A1 | 7/2004 | Cox | |
| 2004/0186561 A1 | 9/2004 | McGuckin et al. | |
| 2004/0210304 A1 | 10/2004 | Seguin et al. | |
| 2004/0210307 A1 | 10/2004 | Khairkhahan | |
| 2004/0215325 A1 | 10/2004 | Penn et al. | |
| 2004/0225353 A1 | 11/2004 | McGuckin et al. | |
| 2004/0236411 A1 | 11/2004 | Sarac et al. | |
| 2004/0260389 A1* | 12/2004 | Case | A61F 2/2475 623/2.38 |
| 2005/0033398 A1 | 2/2005 | Seguin | |
| 2005/0075727 A1 | 4/2005 | Wheatley | |
| 2005/0090887 A1 | 4/2005 | Pryor | |
| 2005/0096738 A1 | 5/2005 | Cali et al. | |
| 2005/0107872 A1 | 5/2005 | Mensah et al. | |
| 2005/0137682 A1 | 6/2005 | Justino | |
| 2005/0137686 A1* | 6/2005 | Salahieh | A61F 2/2439 623/2.11 |
| 2005/0137687 A1 | 6/2005 | Salahieh et al. | |
| 2005/0137690 A1* | 6/2005 | Salahieh | A61F 2/2427 623/1.36 |
| 2005/0137691 A1* | 6/2005 | Salahieh | A61F 2/2418 623/2.11 |
| 2005/0137693 A1 | 6/2005 | Haug et al. | |
| 2005/0159811 A1 | 7/2005 | Lane | |
| 2005/0182486 A1 | 8/2005 | Gabbay | |
| 2005/0216079 A1 | 9/2005 | MaCoviak | |
| 2005/0234546 A1 | 10/2005 | Nugent et al. | |
| 2005/0283231 A1 | 12/2005 | Haug et al. | |
| 2006/0020321 A1* | 1/2006 | Parker | A61F 2/91 623/1.12 |
| 2006/0020327 A1 | 1/2006 | Lashinski et al. | |
| 2006/0052867 A1* | 3/2006 | Revuelta | A61F 2/2418 623/2.38 |
| 2006/0058872 A1* | 3/2006 | Salahieh | A61F 2/2412 623/1.36 |
| 2006/0095115 A1 | 5/2006 | Bladillah et al. | |
| 2006/0173537 A1* | 8/2006 | Yang | A61F 2/2427 623/2.18 |
| 2006/0195183 A1 | 8/2006 | Navia et al. | |
| 2006/0212110 A1 | 9/2006 | Osborne et al. | |
| 2006/0241745 A1 | 10/2006 | Solem | |
| 2006/0259135 A1 | 11/2006 | Navia et al. | |
| 2006/0265056 A1 | 11/2006 | Nguyen et al. | |
| 2006/0287717 A1 | 12/2006 | Rowe et al. | |
| 2006/0293745 A1 | 12/2006 | Carpentier et al. | |
| 2007/0010876 A1 | 1/2007 | Salahieh et al. | |
| 2007/0043435 A1 | 2/2007 | Seguin et al. | |
| 2007/0050021 A1 | 3/2007 | Johnson | |
| 2007/0100432 A1 | 5/2007 | Case et al. | |
| 2007/0100435 A1 | 5/2007 | Case et al. | |
| 2007/0129794 A1 | 6/2007 | Realyvasquez | |
| 2007/0142906 A1 | 6/2007 | Figulla et al. | |
| 2007/0213813 A1 | 9/2007 | Von Segesser et al. | |
| 2007/0255394 A1 | 11/2007 | Ryan | |
| 2008/0021546 A1 | 1/2008 | Patz et al. | |
| 2008/0071366 A1 | 3/2008 | Tuval et al. | |
| 2008/0082164 A1 | 4/2008 | Friedman | |
| 2008/0082165 A1 | 4/2008 | Wilson et al. | |
| 2008/0097581 A1 | 4/2008 | Shanley | |
| 2008/0147179 A1 | 6/2008 | Cai et al. | |
| 2008/0147183 A1 | 6/2008 | Styrc | |
| 2008/0161911 A1 | 7/2008 | Revuelta et al. | |
| 2008/0177381 A1 | 7/2008 | Navia et al. | |
| 2008/0183273 A1 | 7/2008 | Mesana et al. | |
| 2008/0208328 A1 | 8/2008 | Antocci et al. | |
| 2008/0228254 A1 | 9/2008 | Ryan | |
| 2009/0005863 A1 | 1/2009 | Goetz et al. | |
| 2009/0076598 A1* | 3/2009 | Salahieh | A61F 2/2412 623/2.11 |
| 2009/0088832 A1* | 4/2009 | Chew | A61F 2/88 623/1.42 |
| 2009/0138079 A1 | 5/2009 | Tuval et al. | |
| 2009/0171456 A1 | 7/2009 | Kveen et al. | |
| 2009/0182413 A1 | 7/2009 | Burkart et al. | |
| 2009/0188964 A1 | 7/2009 | Orlov | |
| 2009/0234443 A1* | 9/2009 | Ottma | A61F 2/2418 623/2.11 |
| 2009/0240320 A1* | 9/2009 | Tuval | A61F 2/2418 623/1.24 |
| 2009/0270972 A1 | 10/2009 | Lane | |
| 2009/0276027 A1 | 11/2009 | Glynn | |
| 2009/0276040 A1 | 11/2009 | Rowe et al. | |
| 2009/0281618 A1 | 11/2009 | Hill et al. | |
| 2009/0287296 A1 | 11/2009 | Manasse | |
| 2009/0292350 A1 | 11/2009 | Eberhardt et al. | |
| 2009/0306768 A1 | 12/2009 | Quadri | |
| 2010/0036479 A1* | 2/2010 | Hill | A61F 2/2457 623/1.26 |
| 2010/0049313 A1 | 2/2010 | Alon et al. | |
| 2010/0114305 A1 | 5/2010 | Kang et al. | |
| 2010/0191326 A1 | 7/2010 | Alkhatib | |
| 2010/0204781 A1 | 8/2010 | Alkhatib | |
| 2010/0204785 A1 | 8/2010 | Alkhatib | |
| 2010/0217382 A1 | 8/2010 | Chau et al. | |
| 2010/0249894 A1 | 9/2010 | Oba et al. | |
| 2010/0249911 A1 | 9/2010 | Alkhatib | |
| 2010/0256723 A1 | 10/2010 | Murray | |
| 2010/0305685 A1 | 12/2010 | Millwee et al. | |
| 2011/0004296 A1 | 1/2011 | Lutter et al. | |
| 2011/0029067 A1 | 2/2011 | McGuckin, Jr. et al. | |
| 2011/0208297 A1 | 8/2011 | Tuval et al. | |
| 2011/0208298 A1 | 8/2011 | Tuval et al. | |
| 2011/0224785 A1 | 9/2011 | Hacohen | |
| 2011/0264196 A1 | 10/2011 | Savage et al. | |
| 2011/0313515 A1 | 12/2011 | Quadri et al. | |
| 2012/0022639 A1 | 1/2012 | Hacohen et al. | |
| 2012/0041550 A1 | 2/2012 | Salahieh et al. | |
| 2012/0059454 A1 | 3/2012 | Millwee et al. | |
| 2012/0078360 A1 | 3/2012 | Rafiee | |
| 2012/0101571 A1 | 4/2012 | Thambar et al. | |
| 2012/0101572 A1 | 4/2012 | Kovalsky et al. | |
| 2012/0123529 A1 | 5/2012 | Levi et al. | |
| 2012/0215303 A1 | 8/2012 | Quadri et al. | |
| 2012/0271398 A1 | 10/2012 | Essinger et al. | |
| 2012/0290062 A1 | 11/2012 | McNamara et al. | |
| 2012/0310328 A1 | 12/2012 | Olson et al. | |
| 2013/0006294 A1 | 1/2013 | Kashkarov et al. | |
| 2013/0035759 A1 | 2/2013 | Gross et al. | |
| 2013/0053950 A1 | 2/2013 | Rowe et al. | |
| 2013/0131788 A1 | 5/2013 | Quadri et al. | |
| 2013/0144378 A1 | 6/2013 | Quadri et al. | |
| 2013/0211508 A1 | 8/2013 | Lane et al. | |
| 2013/0253635 A1 | 9/2013 | Straubinger et al. | |
| 2013/0253642 A1 | 9/2013 | Brecker | |
| 2013/0310928 A1 | 11/2013 | Morriss et al. | |
| 2013/0331929 A1 | 12/2013 | Mitra et al. | |
| 2013/0338766 A1 | 12/2013 | Hastings et al. | |
| 2013/0345786 A1 | 12/2013 | Behan | |

(56) References Cited

U.S. PATENT DOCUMENTS

| | | |
|---|---|---|
| 2014/0005764 A1* | 1/2014 | Schroeder ............... A61F 2/07 623/1.13 |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0088565 A1 | 3/2014 | Vongphakdy et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1 | 9/2014 | Ratz et al. |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0142103 A1 | 5/2015 | Vidlund |
| 2015/0148731 A1 | 5/2015 | Mcnamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| DE | 102006052564 B3 | 12/2007 |
| EP | 1171059 A1 | 1/2002 |
| EP | 1255510 A1 | 11/2002 |
| EP | 1259194 B1 | 11/2002 |
| EP | 1281375 A2 | 2/2003 |
| EP | 1369098 A1 | 12/2003 |
| EP | 1472996 A1 | 11/2004 |
| EP | 1734903 A1 | 12/2006 |
| EP | 1827558 A2 | 9/2007 |
| EP | 1239901 B1 | 10/2007 |
| EP | 2124826 A1 | 12/2009 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2319458 A1 | 5/2011 |
| EP | 2398543 A1 | 12/2011 |
| EP | 2496182 A1 | 9/2012 |
| EP | 2566416 A1 | 3/2013 |
| EP | 2745805 A1 | 6/2014 |
| EP | 2419050 B1 | 7/2014 |
| EP | 2749254 A1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |

(56) References Cited

FOREIGN PATENT DOCUMENTS

| | | |
|---|---|---|
| JP | 2008541865 A | 11/2008 |
| WO | 9749355 A1 | 12/1997 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2007134290 A2 | 11/2007 |
| WO | 2008013915 A2 | 1/2008 |
| WO | 2008035337 A2 | 3/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2010121076 A2 | 10/2010 |
| WO | 2010127041 A1 | 11/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Vu, Duc-Thang, et al., "Novel Sutureless Mitral Valve Implantation Method Involving a Bayonet Insertion and Release Mechanism: A Proof of Concept Study in Pigs," The Journal of Thoracic and Cardiovascular Surgery, vol. 143, No. 4, 985-988, Apr. 2012, Applicant believes this may have been available online as early as Feb. 13, 2012.

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as June of 2014.

Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Bavaria, Joseph E. M.D. et al.: "Transcatheter Mitral Valve Implantation: The Future Gold Standard for MR?," Applicant requests the Examiner to consider this reference to be prior art as of December of 2010.

Bavaria, Joseph E. M.D.: "CardiAQ Valve Technologies: Transcatheter Mitral Valve Implantation," Sep. 21, 2009.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages, Applicant believes this may have been available online as early as Feb. 7, 2011.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first-in/382370.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

Boudjemline, Younes, et al., "Steps Toward the Percutaneous Replacement of Atrioventricular Valves," JACC, vol. 46, No. 2, Jul. 19, 2005:360-5.

"CardiAQ™ Valve Technologies reports Successful First-in-Human Trans-Apical implantation of its Second Generation Transcatheter Mitral Valve," CardiAQ Valve Technologies Press Release, May 20, 2014.

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

"Company Overview," at TVT on Jun. 25, 2009.

Condado, Jose Antonio, et al., "Percutaneous Treatment of Heart Valves," Rev Esp Cardio. 2006;59(12):1225-31, Applicant believes this may have been available as early as December of 2006.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages Applicant believes this may have been available online as early as Aug. 25, 2013.

Fanning, Jonathon P., et al., "Transcatheter Aortic Valve Implantation (TAVI): Valve Design and Evolution," International Journal of Cardiology 168 (2013) 1822-1831, Applicant believes this may have been available as early as Oct. 3, 2013.

Feldman, Ted, MD. "Prospects for Percutaneous Valve Therapies," Circulation 2007; 116:2866-2877. Applicant believes that this may be available as early as Dec. 11, 2007.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.

Grube, E. et al., "Percutaneous aortic valve replacement for severe aortic stenosis in high-risk patients using the second- and current third-generation self-expanding CoreValve prosthesis: device suc-

(56) References Cited

OTHER PUBLICATIONS cess and 30-day clinical outcome." J Am Coll Cardiol. Jul. 3, 2007;50(1):69-76. Epub Jun. 6, 2007.
Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Karimi, Houshang, et al., "Percutaneous Valve Therapies," SIS 2007 Yearbook, Chapter 11, pp. 1-11.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.
Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.
Ma, Liang, et al., "'Double-Crowned Valved Stents for Off-Pump Mitral Valve Replacement," European Journal of Cardio-thoracic Surgery 28 (2005) 194-199, Applicant believes this may have been available as early as August of 2005.
Mack, Michael, M.D., "Antegrade Transcatheter Mitral valve Implantation: A Short-term Experience in Swine Model," Applicant believes this may have been presented on May of 2011 at TVT.
Mack, Michael, M.D., "Antegrade Transcatheter Mitral valve Implantation: On-Going Experience in Swine Model," Applicant believes this may have been presented on November of 2011 at TCT.
Masson, Jean-Bernard, et al., "Percutaneous Treatment of Mitral Regurgitation," Circulation: Cardiovascular Interventions, 2:140-146, Applicant believes this may have been available as early as Apr. 14, 2009.
Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.
Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as August of 2008.

Pluth, James R., M.D., et al., "Aortic and Mitral Valve Replacement with Cloth-Covered Braunwald-Cutter Prosthesis a Three-Year Follow-up," The Annals of Thoracic Surgery, vol. 20, No. 3, Sep. 1975, pp. 239-248.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent, "LSI EMT Spotlight," May 15, 2009.
Raitz, J. Brent, "In3 Company Overview," Jun. 24, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ruiz, Carlos E., "Overview of Novel Transcatheter Valve Technologies," Applicant believes this may have been presented on May 27, 2010 at EuroPCR.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, et al., "Transcatheter Mitral Valve Implantation: CardiAQ™," Applicant believes this may have been presented at EuroPCR 2013.
Spillner, J. et al., "New Sutureless 'Atrial—Mitral-Valve Prosthesis' for Minimally Invasive Mitral Valve Therapy," Textile Research Journal, 2010, in 7 pages, Applicant believes this may have been available as early as Aug. 9, 2010.
Sondergaard, Lars, "CardiAQ TMVR FIH—Generation 2," Applicants believe this may have been presented in 2014 at the TVT symposium.
Sondergaard, Lars, et al., "Transcatheter Mitral Valve Implantation: CardiAQ™," Applicant believes this may have been presented at TCT 2013.
Treede et al.: "Transapical transcatheter aortic valve implantation using the JenaValve™ system: acute and 30-day results of the multicentre CE-mark study" http://ejcts.oxfordjournals.org/content/41/6/e131.long Apr. 16, 2012.
Taramasso et al.: "New devices for TAVI: technologies and initial clinical experiences" http://www.nature.com/nrcardioljournal/v11/n3/full/nrcardio.2013.221.html?message-global=remove#access. Jan. 21, 2014.
"Update," Applicant believes this may have been presented on Jun. 6, 2010 at TVT.
Webb, John G., et al., "Transcatheter Aortic Valve Implantation: The Evolution of Prostheses, Delivery Systems and Approaches," Archives of Cardiovascular Disease (2012) 105, 153-159. Applicant believes this may have been available as early as Mar. 16, 2012.
Wayback Machine, Cleveland Clinic Lemer Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.

\* cited by examiner

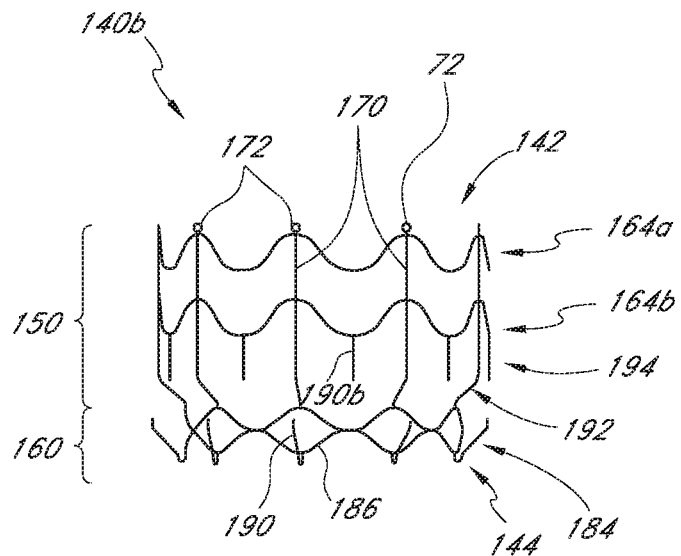
FIG. 7A
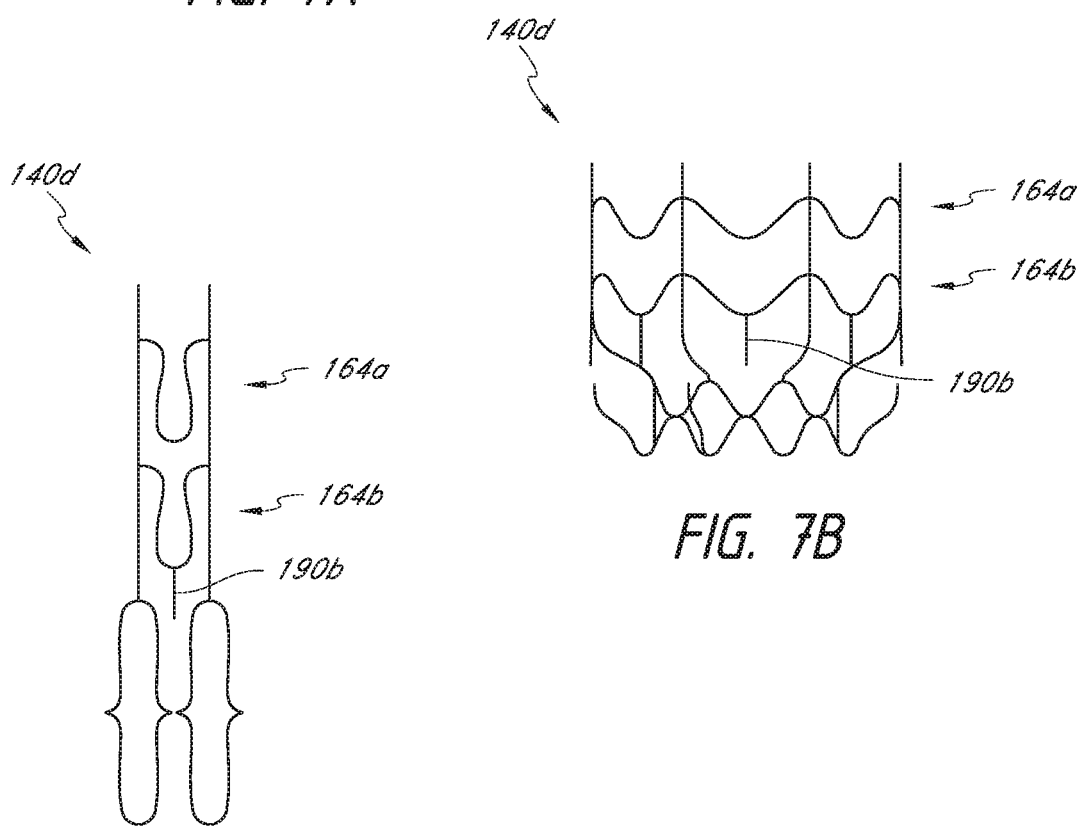
FIG. 7B
FIG. 7C

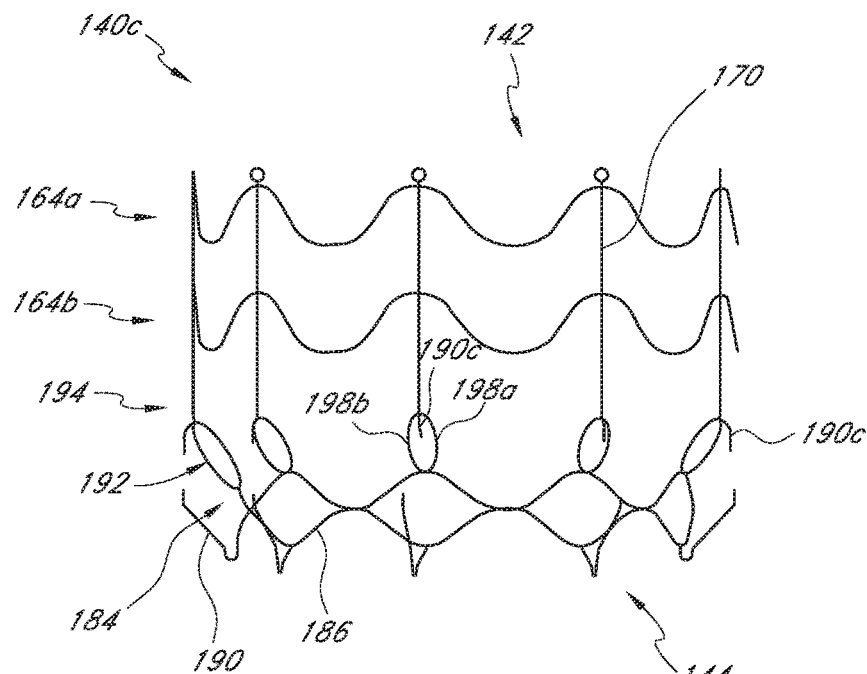
FIG. 8A
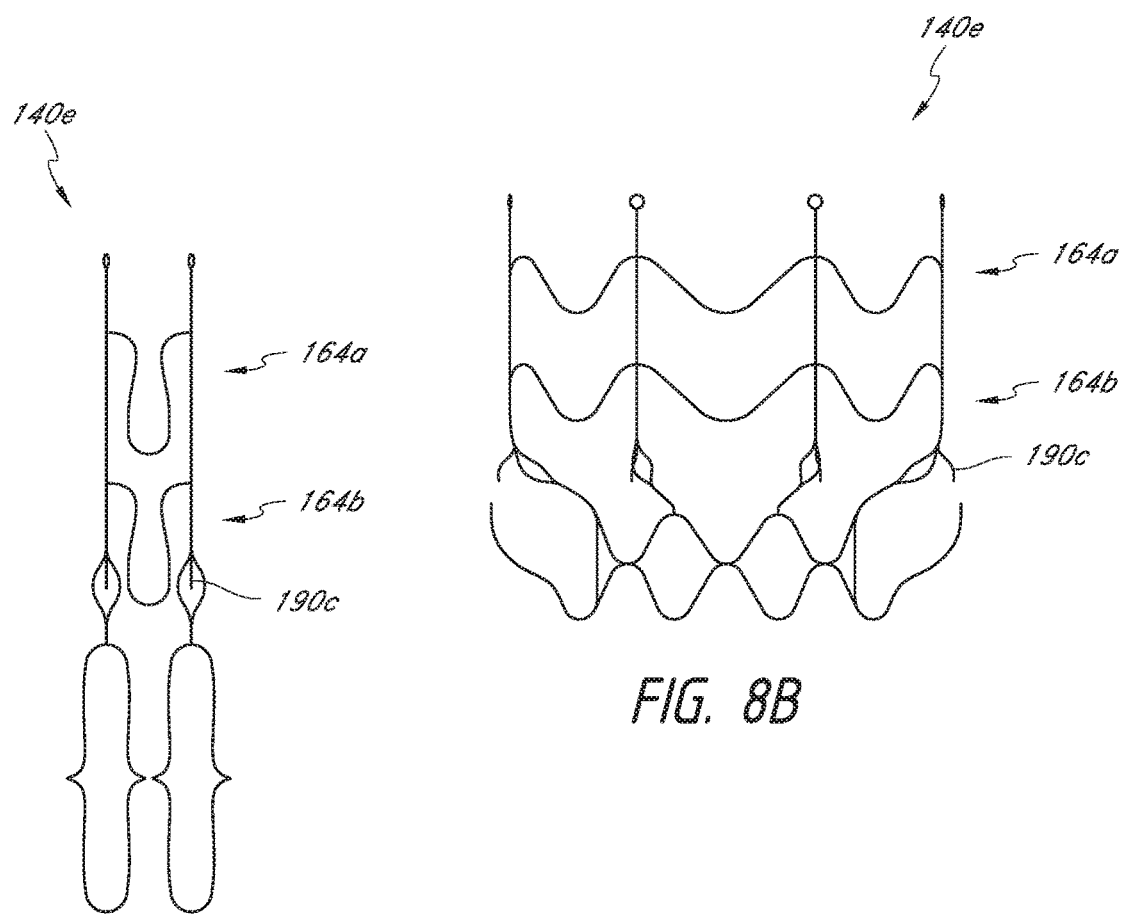
FIG. 8B
FIG. 8C

    
FIG. 9A　　FIG. 9B　　FIG. 9C　　FIG. 9D　　FIG. 9E
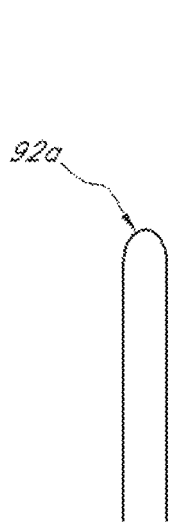 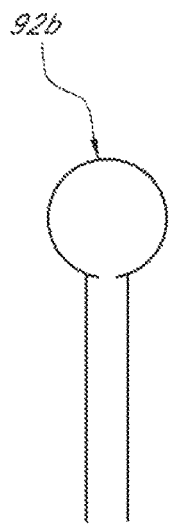  
FIG. 10A　　FIG. 10B　　FIG. 10C　　FIG. 10D

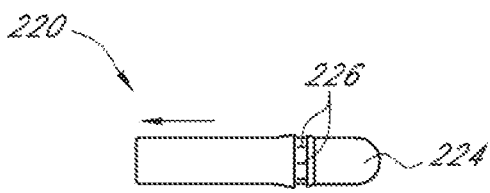
FIG. 12A
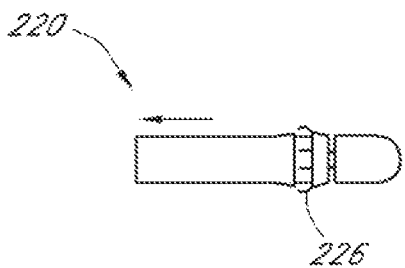
FIG. 12B
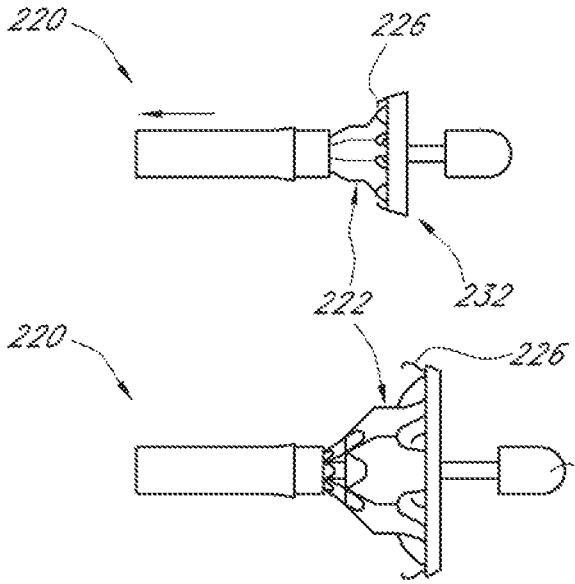
FIG. 12C
FIG. 12D
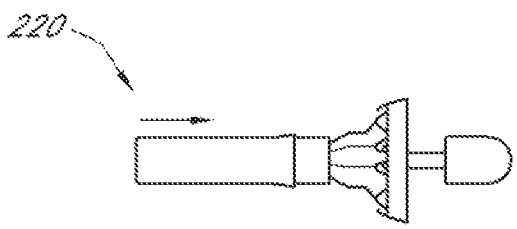
FIG. 12E
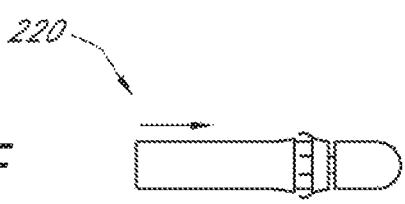
FIG. 12F

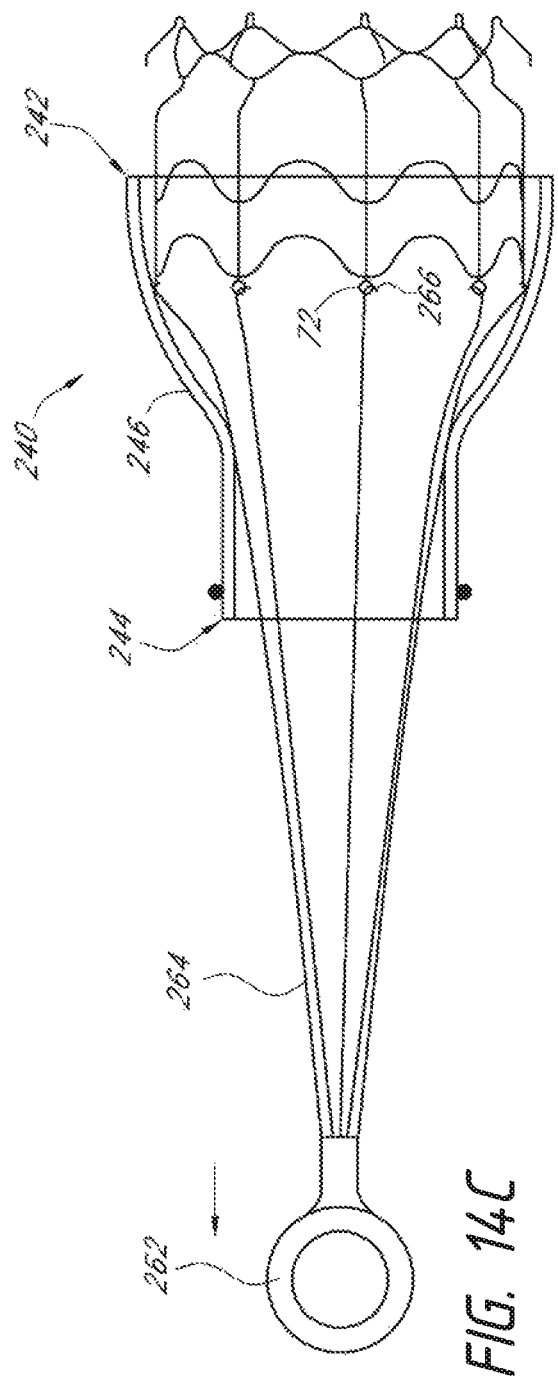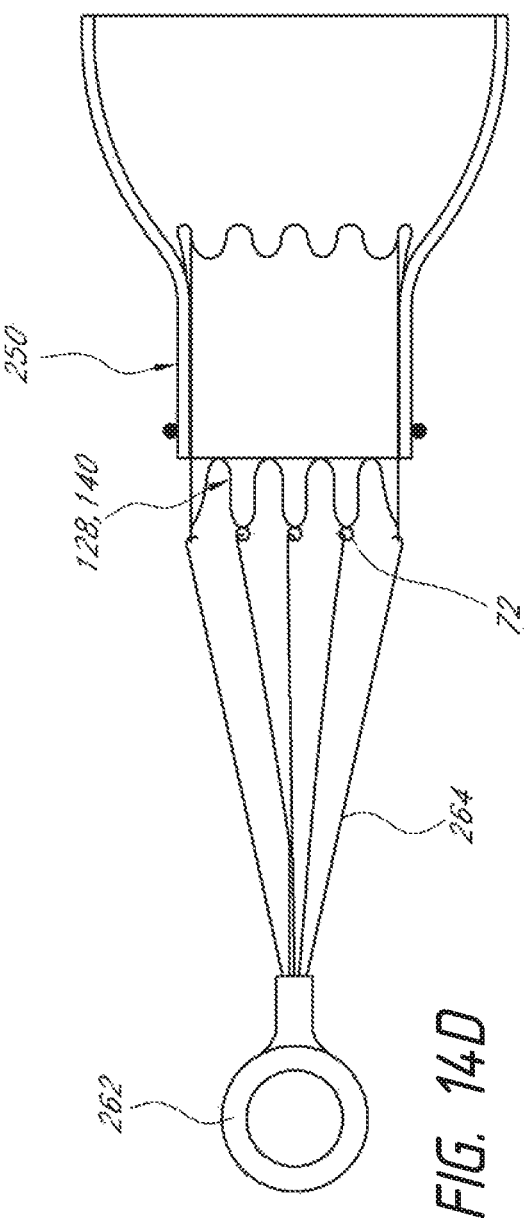

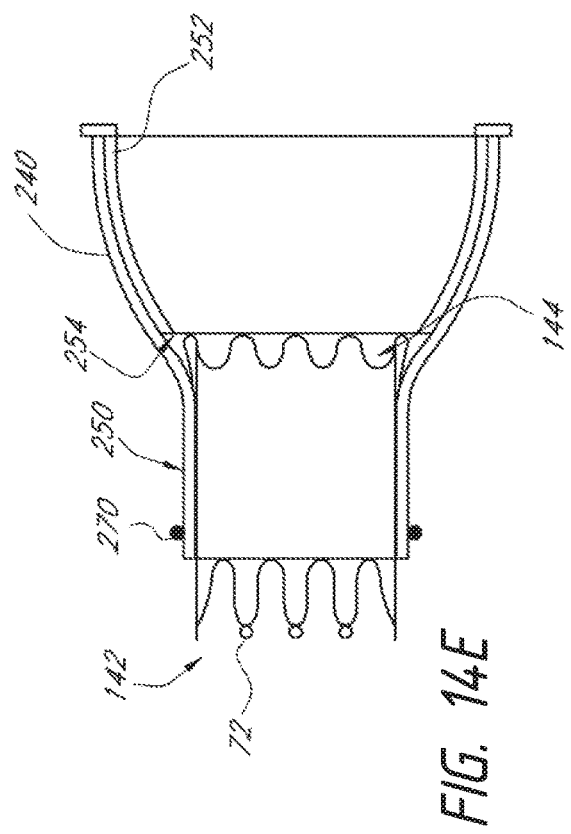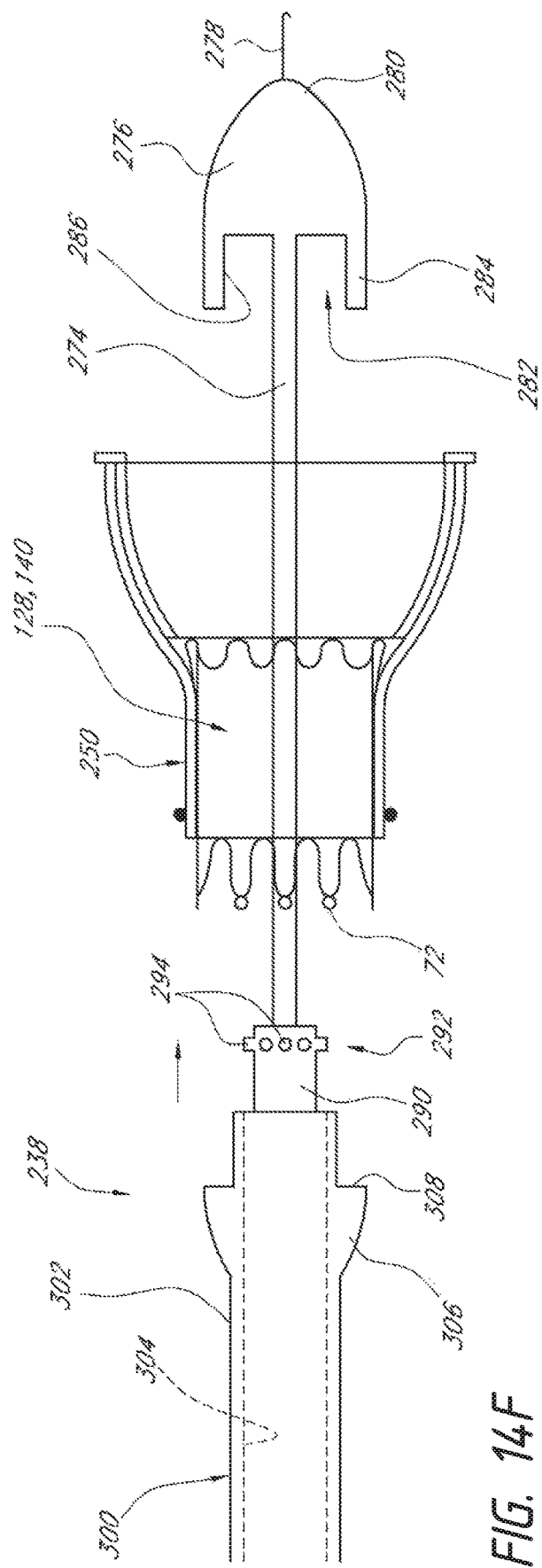

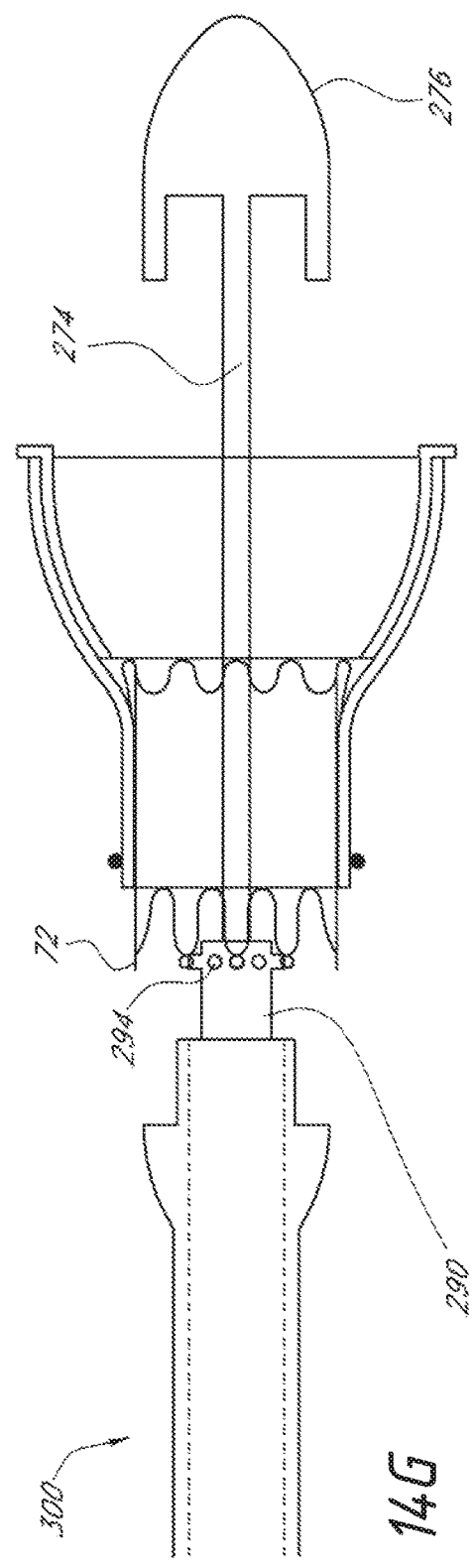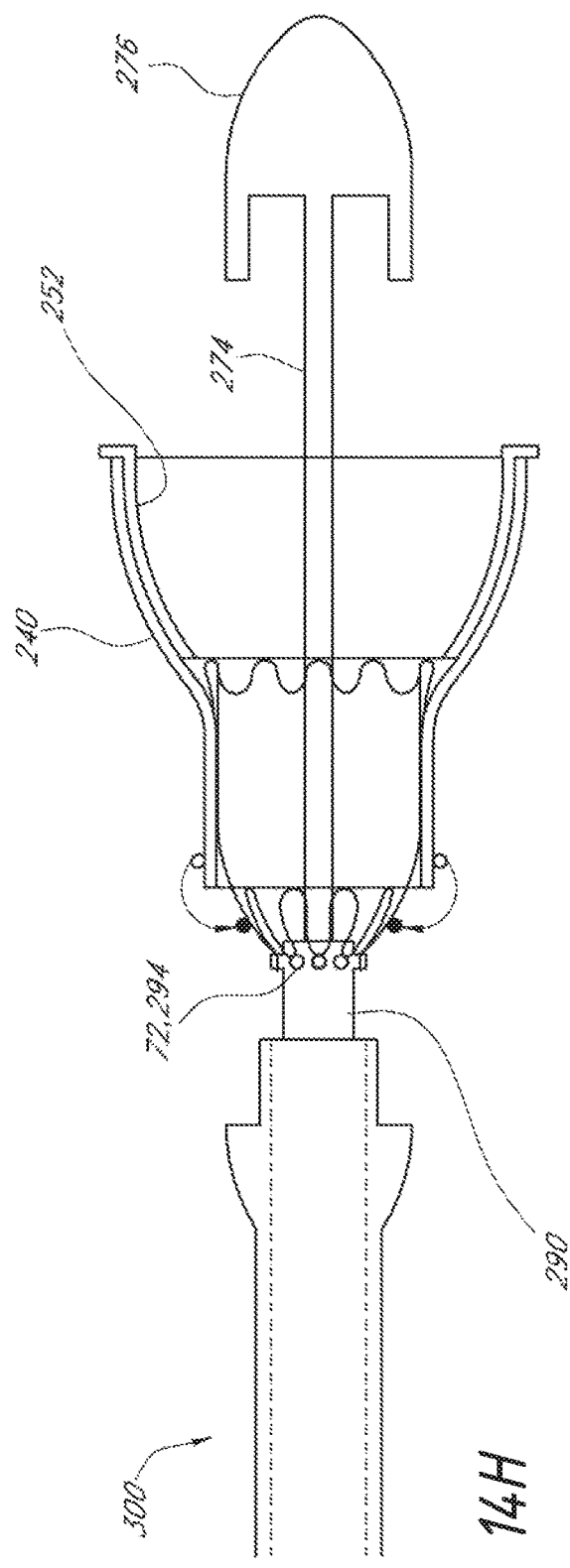

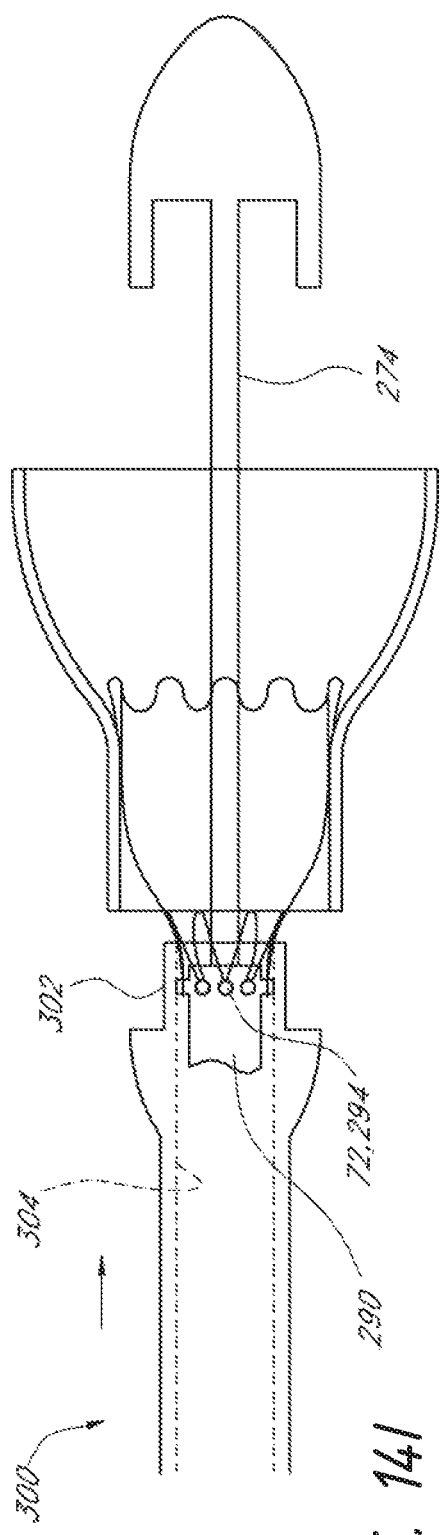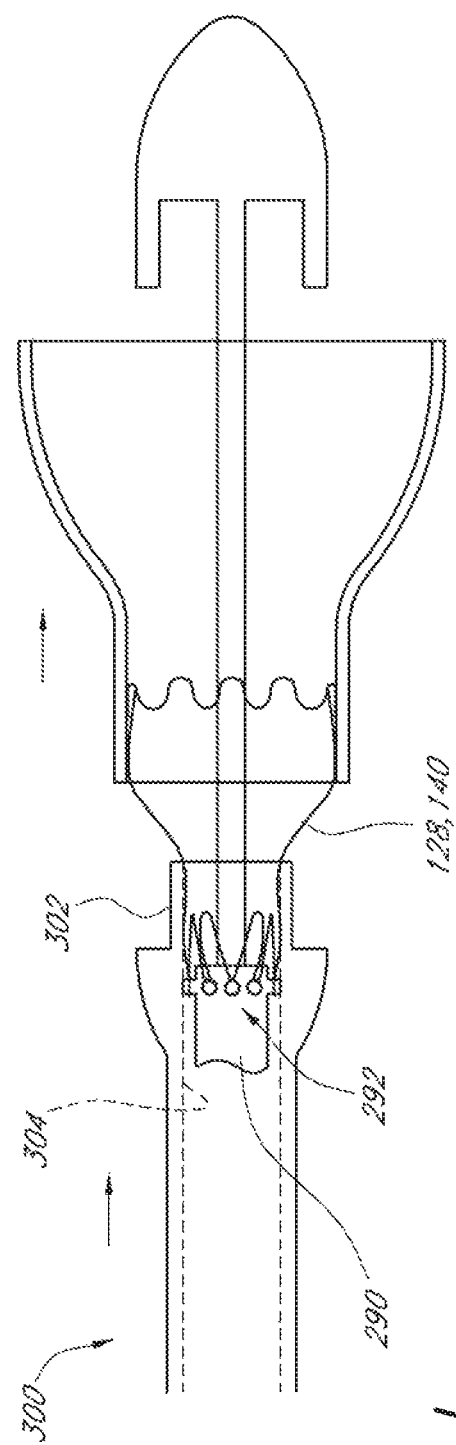

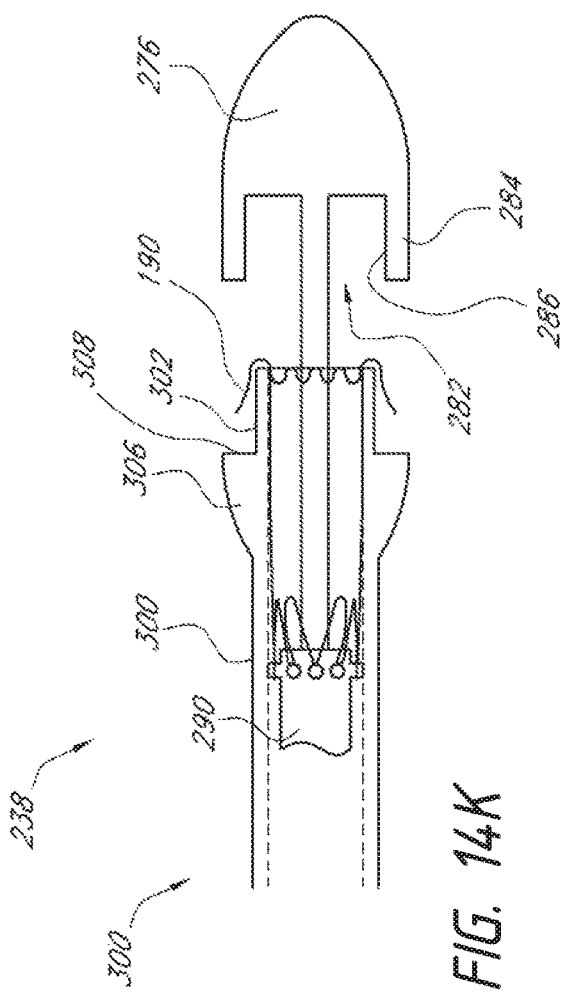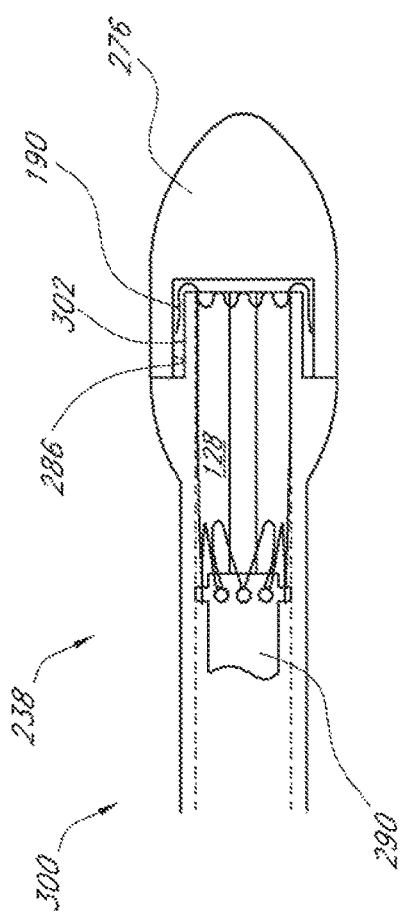

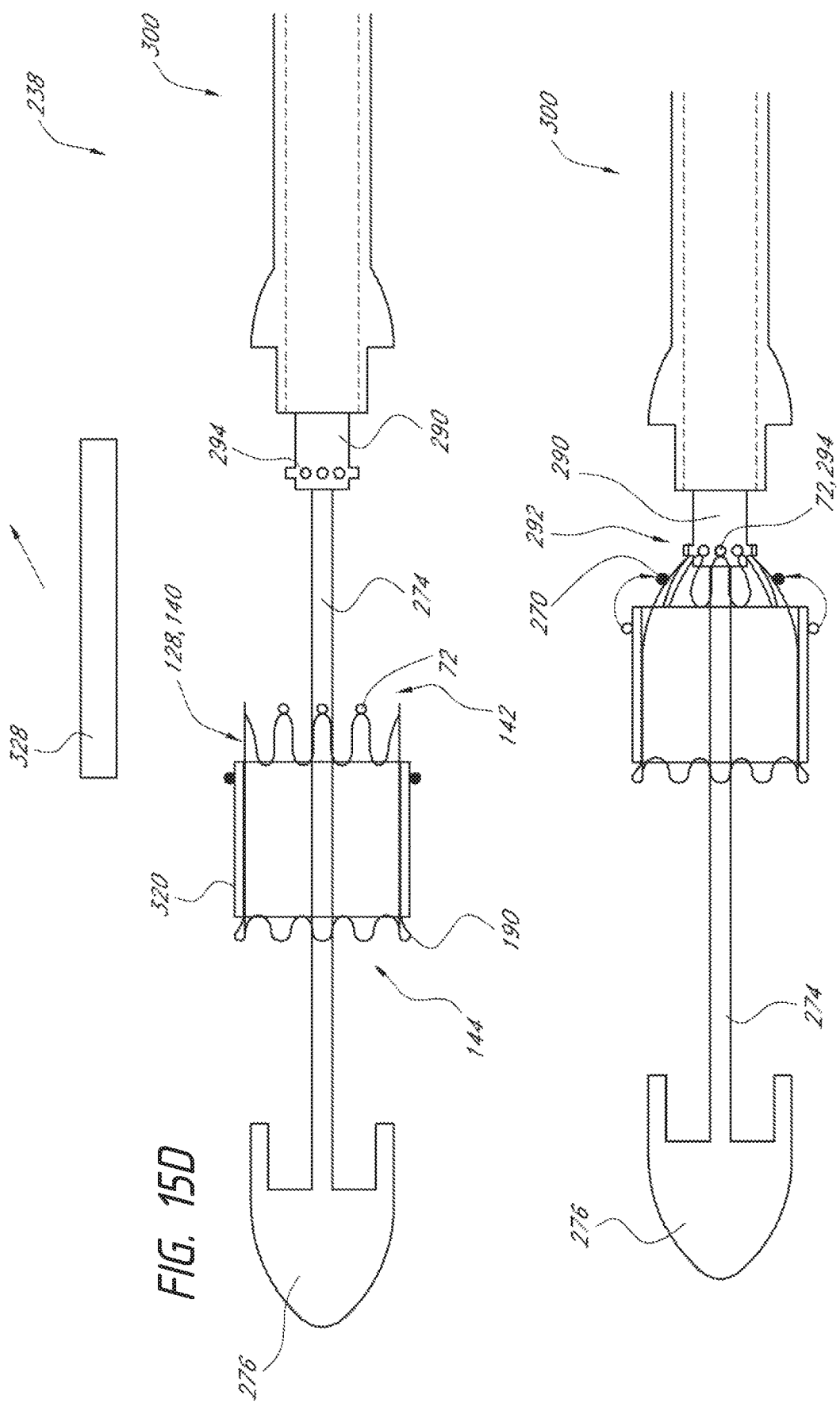

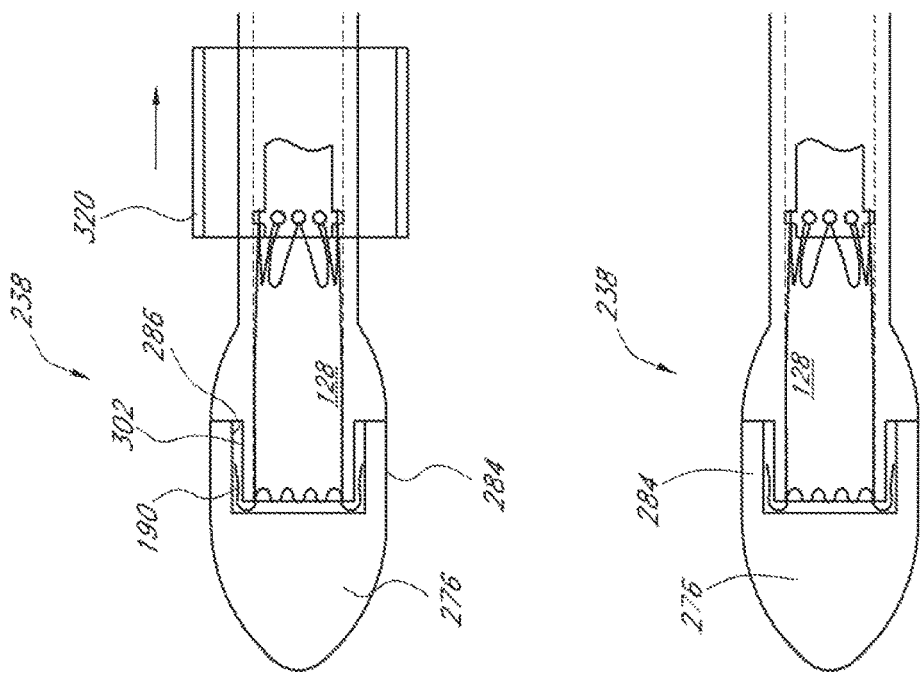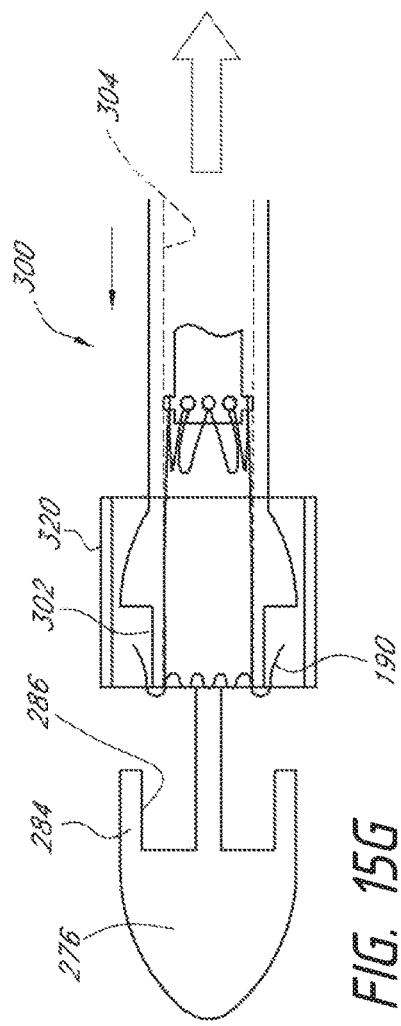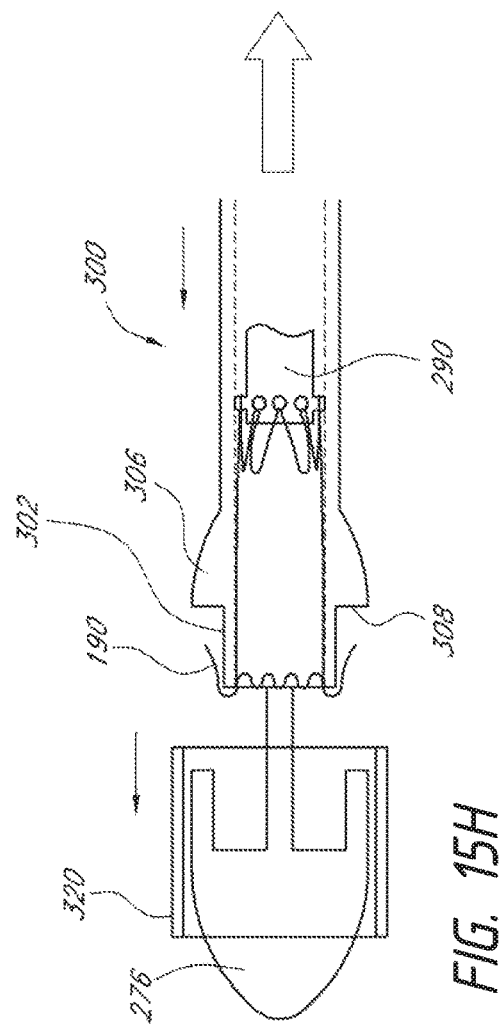
FIG. 15G
FIG. 15H

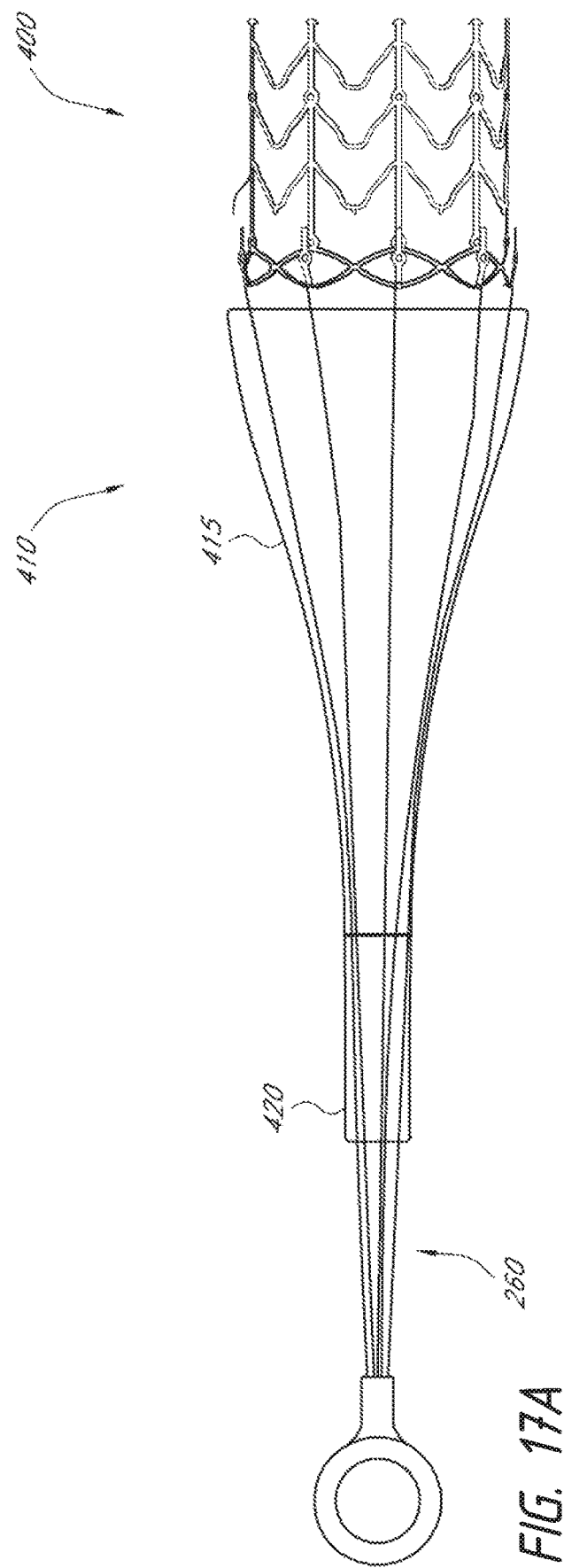

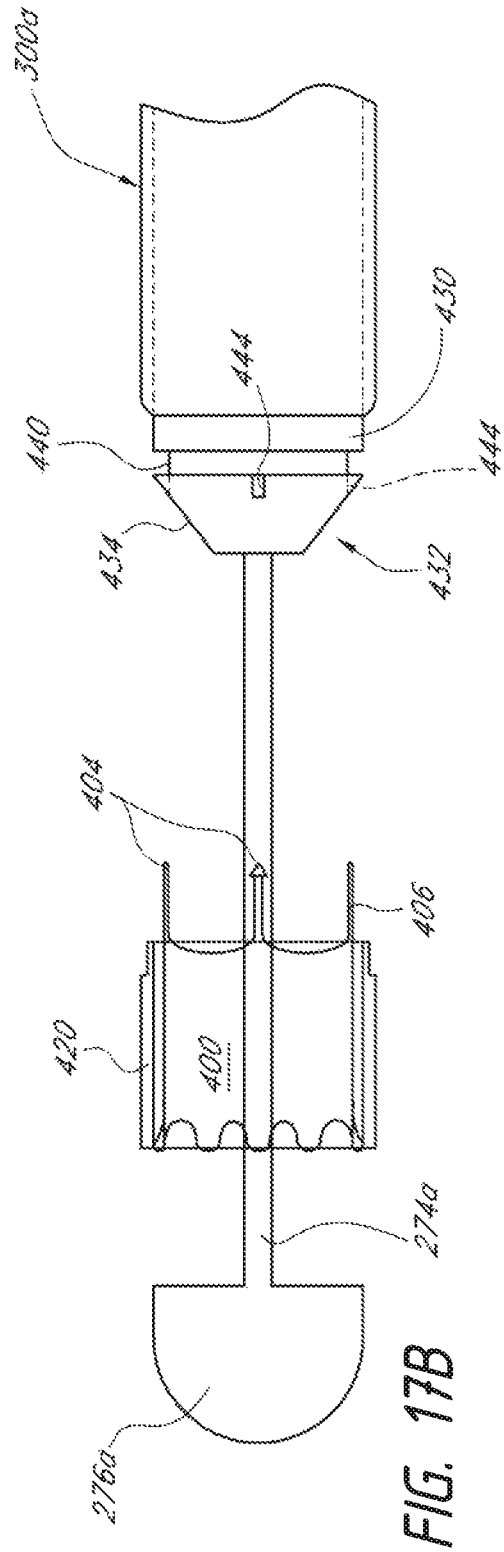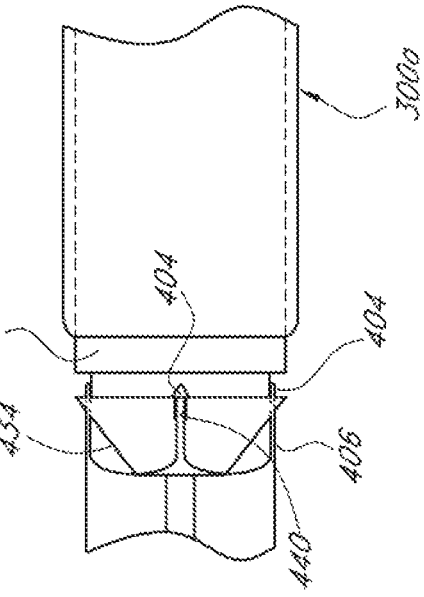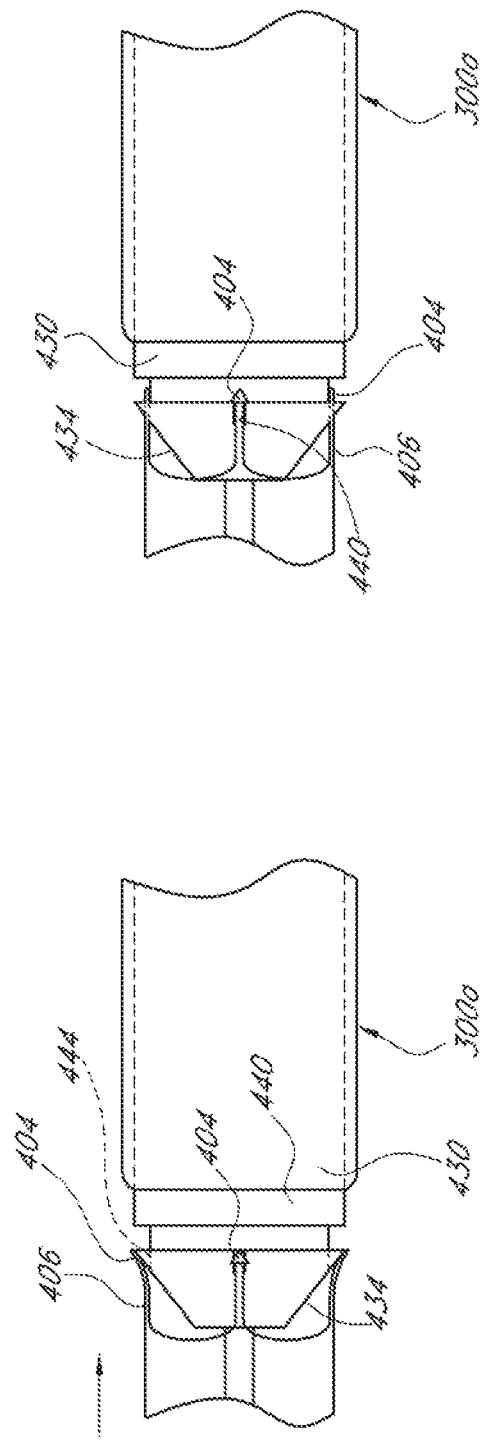

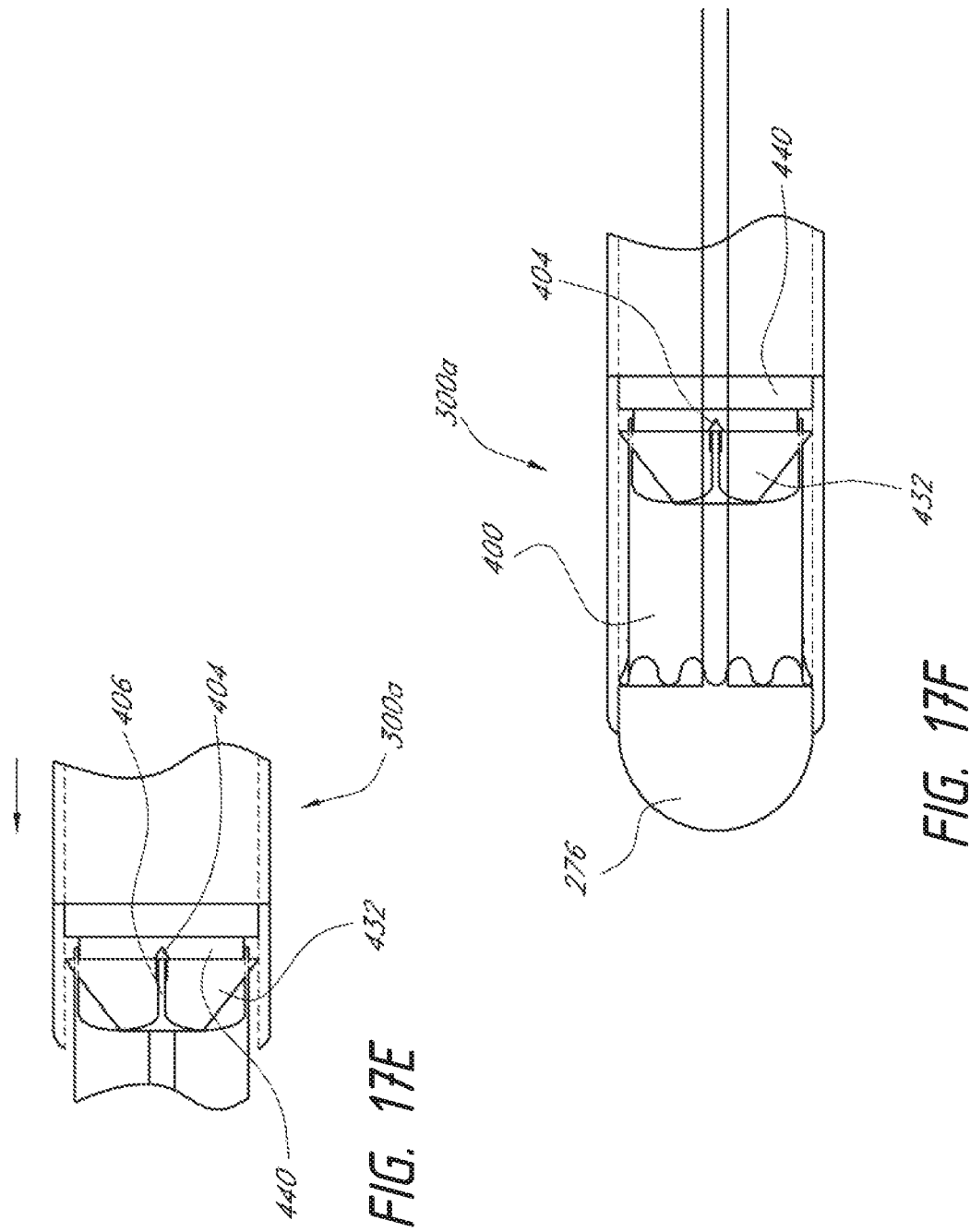

VASCULAR IMPLANT AND DELIVERY SYSTEM

CROSS-REFERENCE TO RELATED APPLICATIONS

This application is a continuation of U.S. application Ser. No. 15/288,693, filed Oct. 7, 2016, now U.S. Pat. No. 10,441,412, which is a continuation of U.S. application Ser. No. 14/313,160, filed Jun. 24, 2014, now U.S. Pat. No. 9,585,747, which is a continuation of U.S. application Ser. No. 13/755,863, filed Jan. 31, 2013, now U.S. Pat. No. 9,339,379, which is a continuation of U.S. application Ser. No. 12/761,349, filed Apr. 15, 2010, now U.S. Pat. No. 8,414,644, which claims priority to U.S. Provisional Application No. 61/169,367, filed Apr. 15, 2009. All of the above applications are hereby incorporated herein by reference in their entirety and are to be considered a part of this specification. Any and all priority claims identified in the Application Data Sheet, or any correction thereto, are hereby incorporated by reference under 37 CFR 1.57.

BACKGROUND

Field of the Invention

The present invention relates to replacement heart valves and systems for delivering replacement heart valves.

Description of the Related Art

Human heart valves, which include the aortic, pulmonary, mitral and tricuspid valves, function essentially as one-way valves operating in synchronization with the pumping heart. The valves allow blood to flow in a downstream direction, but block blood from flowing in an upstream direction. Diseased heart valves exhibit impairments such as narrowing of the valve or regurgitation. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatus to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable stent that is then delivered to the native valve's annulus.

Development of replacement heart valves and associated delivery systems in which the heart valve is compacted for delivery and then controllably expanded for controlled placement has proven to be particularly challenging. Delivery systems that facilitate accurate positioning and reliable placement have also proven to be challenging to develop, particularly systems that enable repositioning of the valve after partial deployment if it is determined that the valve is not positioned correctly.

SUMMARY

Accordingly, there is in the need of the art for an improved replacement heart valve and an improved system for delivering such heart valves in a reliable and controlled manner. The present invention relates to an implantable heart valve design along with a system and method for delivering and implanting the same.

As discussed in U.S. Provisional Application No. 61/169,367, in accordance with some embodiments, a prosthetic heart valve can be attached, without sutures, to a pulmonary valve annulus, an aortic valve annulus (including cases where the native leaflets have been removed), or to an atrio-ventricular valve where the leaflets and subvalvular apparatus can remain intact. Specific attention is paid here to its relevance in the mitral valve position; however, the same technology could be applied to any of the four heart valves depending on the configuration of the design that is used. The implant itself can be comprised of a foldable valve with a plurality of leaflets (utilizing either bovine, equine, or porcine pericardial tissue or a synthetic material), a stent frame, and fabric or tissue-based liner. The valve can be delivered through an open-heart procedure, a minimally-invasive surgical procedure, or remotely through a catheter-based, percutaneous approach.

As further discussed in U.S. Provisional Application No. 61/169,367, in accordance with some embodiments, these and other objects can be achieved by combining a stent frame with a multi-leaflet valve design and a tissue- or fabric-based liner. Some embodiments of the stent frame are made from self-expanding nitinol material; however it could also be made from a self-expanding polymer or a balloon expandable metallic material. In the expanded state, the upper portion of the stent frame may be of a larger diameter than the lower portion. The lower portion sits inside of the native valve annulus (intra-annularly), while the upper portion sits above the native valve annulus (supra-annularly).

In some embodiments, the upper and lower portions of the stent have circular cross-sections; however, it is possible that the upper portion, the lower portion, or the entire stent frame could be formed to have a noncircular cross-section that better approximates the typical cross-section of the native valve annulus in which the prosthetic valve is being implanted. The shoulder that is formed by the transition between the different diameters of the upper and lower portions of the stent frame provides fixation on one side of the native valve annulus and prevents the implant from passing through the native annulus in the axial direction going from the upper portion to the lower portion. The upper portion of the stent frame houses the valve and is designed with a plurality of continuous vertical struts which eliminate foreshortening in that region of the stent frame. As a result, the tensile forces being exerted on the valve material are minimized as it goes from the expanded state to the compressed state during the loading process and from the compressed state to the expanded state during deployment process. The lower portion of the stent frame utilizes the same annular connection mechanism (foreshortening oval cells with anchor features) that is described in U.S. Provisional Application No. 60/735,221. Said features of the stent frame are incorporated by reference to the extent that they are described in U.S. Provisional Application No. 61/169,367 and U.S. patent application Ser. No. 12/084,586, published as U.S. Publication No. 2009/0216314, which claims priority to U.S. Provisional Application No. 60/735,221.

According to certain embodiments, multiple anchor features can extend from the bottom of each of the oval cells that makes up the lower portion of the stent frame. These anchor features can be formed in such a way so that they extend radially outward from the central axis of the stent frame and can be formed in a number of different configurations to achieve optimal fixation. Likewise, the distal tips of these anchor features can have various configurations to achieve optimal tissue engagement, ranging from an atraumatic tip that will not penetrate the tissue at all to a sharp tip that will embed itself into the tissue to some degree. The anchor features oppose the transition shoulder between the upper and lower portions of the stent frame and provide fixation on the opposite side of the native valve annulus, preventing the implant from passing through the native annulus in the axial direction going from the lower portion to the upper portion. The foreshortening that results from the radial expansion of the oval cells in the lower portion of the stent frame will generate an axial clamping force on the native valve annulus between the transition shoulder and the tips of the anchor features. The stent frame may also include some form of radio-opaque markers (e.g. marker bands on the anchor features) to provide for improved visibility under fluoroscope imaging. It is also possible that the transition shoulder between the upper and lower sections of the frame may include small anchor features that facilitate some engagement with the tissue on that side of the annulus.

As further discussed in U.S. Provisional Application No. 61/169,367, in accordance with some embodiments, the valve portion of the prosthetic heart valve implant can utilize the same design as that described in U.S. Provisional Application No. 61/136,716. Said features of the valve portion of U.S. Provisional Application No. 61/136,716 is incorporated by reference to the extent that they are described in U.S. Provisional Application No. 61/169,367 and U.S. patent application Ser. No. 12/569,856, published as U.S. Publication No. 2010/0082094, which claims priority to U.S. Provisional Application No. 60/136,716. In some embodiments, the outer layer of the valve material can be attached to the interior face of the upper portion of the stent frame using suture material or other means. The leaflet portion of the valve material is folded inside of the outer layer of the valve material and attached to the outer layer and/or the stent frame at the commissural posts and along the edges of the leaflets using sutures or other means. The attachment locations may or may not utilize eyelet holes incorporated into the struts of the stent frame. In some embodiments, the location of the fold between the outer layer and the interior leaflet layer does not extend to the end of the stent frame.

During the delivery process, which will be described in detail below, this leaves some portion of the stent frame exposed so that blood can flow freely through the valve and the valve can begin to function prior to final deployment, which in turn, allows more time and control during the delivery process. The lower edge of the outer layer is attached to the upper edge of the tissue- or fabric-based liner, which is attached to the inside face of the lower portion of the stent frame and folds around to the outside face of the anchor features. In some embodiments, the liner is made from a fabric material to facilitate tissue in-growth at the annular region and, thereby, provide better leak prevention overtime. In addition, a fabric-based liner may allow for a greater degree of elasticity to accommodate the radial expansion and axial contraction in the lower portion of the stent frame caused by the foreshortening process. However, the liner could also be made from a separate piece of tissue material or could be constructed by lengthening the outer layer of the valve material and extending it through the intra-annular region of the stent frame, folding it around the base of the lower portion of the stent frame to the outside face of the anchor features, and attaching the terminal edge in the central region of the anchor features, again using sutures or other means.

In accordance with some embodiments, the present disclosure provides a method of loading a device for delivering a self-expanding vascular implant. The method may include drawing a relaxed, expanded vascular implant through an elongate form having a decreasing diameter to a load tube portion having a compacted diameter, engaging a locking end of the implant with a locking mechanism disposed on a support tube, advancing an outer sheath over the engaged locking end and support tube so as to capture the locking end between the sheath and support tube, and advancing the outer sheath over the compacted implant so as to transfer the implant from within the load tube to within the outer sheath.

In one such embodiment, transferring the implant from within the load tube to within the outer sheath comprises further compacting the implant.

As discussed in U.S. Provisional Application No. 61/169, 367, in accordance with some embodiments, accurate and controlled delivery, positioning, and deployment of the implant are achieved by using a delivery device that may consist of a steerable introducer sheath, an outer sheath, a support tube, an inner tube, and a nose cone. The inner tube has an internal diameter sized to fit over a standard guide wire and would be securely attached to the nose cone, such that advancing or retracting the inner tube would also cause the nose cone to move accordingly. The outer diameter of the inner tube is sized to move smoothly within the internal diameter of the support tube. The support tube has an outer diameter sized to move smoothly within the internal diameter of the outer sheath. The distal end of the support tube also has a locking feature that, when covered by the out sheath, maintains a connection to the prosthetic heart valve implant via mating features on the end of the stent frame and prevents the implant from being fully deployed and released until the user chooses to do so.

Some embodiments of a trans-catheter, percutaneous system may utilize a steerable introducer sheath whose inner diameter is sized to accommodate the outer diameter of the outer sheath and which has a separate handle that allows for relative motion between this component and the outer sheath, support tube, and inner tube as a separate system. The steerable introducer sheath would be capable of controlled deflection in one or more planes and would be used as needed to attain proper axial alignment between the delivery catheter and the native annular plane such that the two were perpendicular to one another. In another embodiment, the support tube could be constructed to have the same steerable characteristics, allowing for relative motion of both the inner tube and the outer sheath with respect to the deflectable support tube and eliminating the need for the steerable introducer sheath. In the case of an open-chest or minimally-invasive or surgical procedure, the distal end of the delivery device could be shorter, with a stiff shaft for optimal control. In the case of a trans-catheter or percutaneous procedure, the distal end of the delivery device would be longer with a flexible shaft to more easily navigate the vasculature. In both cases, the hand controls at the proximal are similar, as are the mechanics of delivery and deployment at the distal, which are described in detail below.

In accordance with another embodiment, the present disclosure provides a vascular implant delivery device. The device can comprise an elongate support tube having a distal end, a locking mechanism being disposed at or adjacent the distal end. An elongate sheath is adapted to slide over the support tube. A self-expanding vascular implant has a locking member. The support tube locking mechanism is configured to engage the implant locking member so as to block axial movement of the implant when the locking mechanism and locking member are engaged. The sheath has an inner lumen sized to block the implant locking member from moving radially relative to the support tube locking mechanism sufficient to release from the support tube locking mechanism.

In order for the prosthetic heart valve assembly to be delivered, it must first be loaded into the delivery device. To do this several variations of a loading system have been devised that would be capable of controllably reducing the diameter of the stent frame (and thereby reducing the diameter of the tissue valve and fabric liner). Several embodiments of the loading system are described and can include a funnel with a large diameter side capable of accommodating the implant in its expanded form and a small diameter side that will be just larger than the outside diameter of the outer sheath of the delivery device. A component called the octopus puller is inserted through the small side of the funnel and attached to the end of the stent frame of the prosthetic heart valve assembly. It can then be used to pull the prosthetic heart valve assembly through the funnel and reduce the diameter as it does. With the diameter sufficiently reduced, the prosthetic heart valve assembly can be loaded into the delivery device.

In one such embodiment, the self-expanding vascular implant remains connected to the support tube so long as the sheath extends distally past the support tube locking mechanism, and the device is configured so that when the sheath is moved proximally past the support tube locking mechanism, the implant locking member moves radially out of engagement with the support tube.

In accordance with yet another embodiment, the present disclosure provides a method of delivering a self-expanding vascular implant. The method may include advancing the implant within a patient's vasculature to a desired delivery location, the implant being advanced while maintained in a compacted configuration within a sheath, a first end of the implant being captured between the sheath and a support tube locking mechanism. The method further includes withdrawing the sheath proximally sufficient to enable a second end of the self-expanding implant to expand radially to a fully expanded size while the first end of the implant remains captured. The second end of the implant is positioned in a desired position and orientation while the first end of the implant remains captured. The method further includes withdrawing the sheath proximally sufficient to release the first end of the implant.

In once such embodiment, if it is determined that the second end of the implant is not positioned as desired, the method additionally comprises moving the sheath distally so as to at least partially recapture the implant within the sheath, repositioning the delivery device, and again withdrawing the sheath proximally sufficient to enable the second end of the implant to expand radially.

Other inventive embodiments and features are disclosed below.

BRIEF DESCRIPTION OF THE DRAWINGS

FIG. 7A is a plan view of a stent frame configured in accordance with still another embodiment.

FIG. 7B is a plan view of a stent frame configured in accordance with yet a further embodiment.

FIG. 7C is a plan view of the stent frame of FIG. 7B in a compressed configuration.

FIG. 8A is a plan view of a stent frame configured in accordance with yet a further embodiment.

FIG. 8B is a plan view of a stent frame configured in accordance with yet a further embodiment.

FIG. 8C is a plan view of the stent frame of FIG. 8B in a compressed configuration.

FIGS. 9A-E show exemplary embodiments of anchor portions for use with stent frame embodiments as discussed herein.

FIGS. 10A-D show exemplary embodiments of anchor tip portions for use with stent frame embodiments as discussed herein.

FIGS. 12A-I show a distal end of a delivery device at several stages during a delivery operation in accordance with a preferred embodiment.

FIGS. 14A-L show an embodiment of a delivery device and an embodiment of a structure for loading an implant onto the delivery device, shown at several stages during a loading operation.

FIGS. 15A-H show another embodiment of a loading device and associated method shown at several stages during the operation of loading an implant onto a delivery device.

FIGS. 17A-F show another embodiment of a delivery device and an embodiment of a structure for loading an implant onto such a delivery device, shown at selected stages during a loading operation.

DETAILED DESCRIPTION OF PREFERRED EMBODIMENTS

The present specification and drawings disclose aspects and features of the invention in the context of embodiments of replacement heart valves and delivery systems for delivering replacement heart valves. For illustrative purposes the embodiments disclosed herein are discussed in connection with replacing the patient's mitral valve. However, it is to be understood that the context of a particular valve or particular features of a valve should not be taken as limiting, and features of any embodiment discussed herein can be employed in connection with prostheses and delivery systems for replacing other vascular valves, and features of any embodiment can be combined with features of other embodiments as desired and when appropriate.

Figure 18:
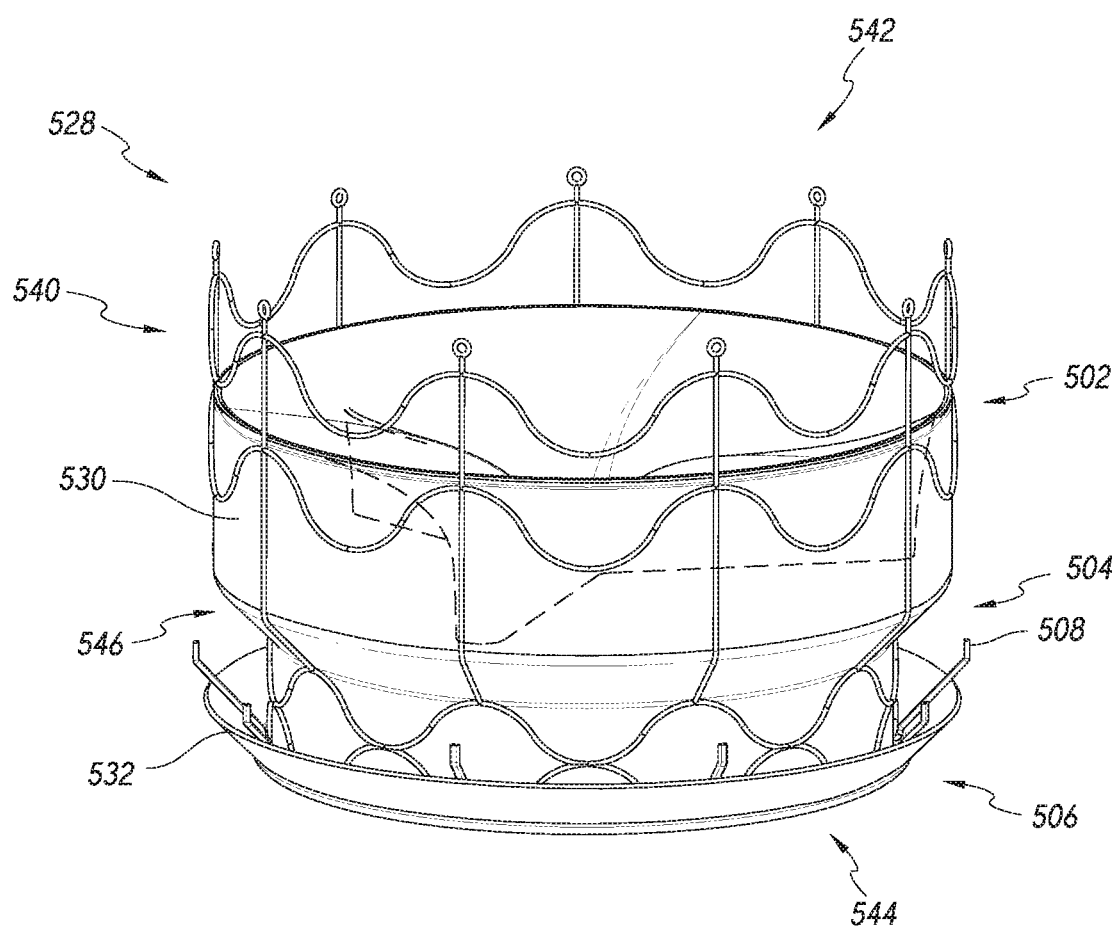
FIG. 18 shows an embodiment of a prosthetic heart valve assembly.

As discussed in U.S. Provisional Application No. 61/169,367, referring to FIG. 18, there is shown a three dimensional view of one embodiment of the prosthetic heart valve assembly 528 intended to be used in the atrio-ventricular position and includes the stent frame 540, a pericardial tissue valve 530, and a fabric-based liner 532. Reference numeral 502 points to the tissue valve in the upper portion of the stent frame 540, which is the same valve design that is described in U.S. Provisional Application No. 61/136,716. Said valve design of U.S. Provisional Application No. 61/136,716 is incorporated by reference to the extent that they are described in U.S. Provisional Application No. 61/169,367 and U.S. patent application Ser. No. 12/569,856, published as U.S. Publication No. 2010/0082094, which claims priority to U.S. Provisional Application No. 60/136,716. In the mitral position, the upper portion 542 of the stent frame 540 and the tissue valve 530 are designed to sit in the left atrium of the heart just above the mitral valve annulus. As noted in the figures of U.S. Provisional Application No. 61/169,367, in this embodiment, the origami valve design can attach to the upper section 542 of the frame 540 located within the left atrium.

Reference numeral 504 points to the connection region of the stent frame 540 where the shoulder 546 formed by the transition between the upper and lower portions 542, 544 of the stent frame 540 captures the low-pressure (atrial) side of the valve annulus and the anchor features 548 extending from the bottom of the lower portion 544 of the stent frame 540 captures the high-pressure (ventricular) side of the annulus. The foreshortening action in the lower portion of the stent frame 540 causes the anchor features 548 to move toward the transition shoulder 546 and generates an axial clamping force that securely attaches the implant onto the valve annulus. The cell geometry in this portion of the stent frame 540 utilizes the same annular connection mechanism (foreshortening oval cells with anchor features) that is described in U.S. Provisional Application No. 60/735,221. Said cell geometry of the stent frame 540 are incorporated by reference to the extent that they are described in U.S. Provisional Application No. 61/169,367 and U.S. patent application Ser. No. 12/084,586, published as U.S. Publication No. 2009/0216314, which claims priority to U.S. Provisional Application No. 60/735,221. Each anchor feature 548 is allowed to move independently and allows the stent frame 540 to accommodate variations in the planar anatomy of the valve annulus.

Reference numeral 506 points to the fabric-liner 532 which lines the intra-annular space on the interior face of the lower portion 544 of the stent frame 540 and wraps around to the outside face of the anchor features 548 where it is securely attached using sutures or other means. As further noted in the figures of U.S. Provisional Application No. 61/169,367, in this embodiment, fabric can line the intra-annular space and wrap around the anchors 548 on the ventricular side to prevent leaks. The fabric-liner 532 facilitates tissue in-growth and provides a tighter seal to the surrounding tissue to reduce the risk of paravalvular leaks.

Figure 19A:
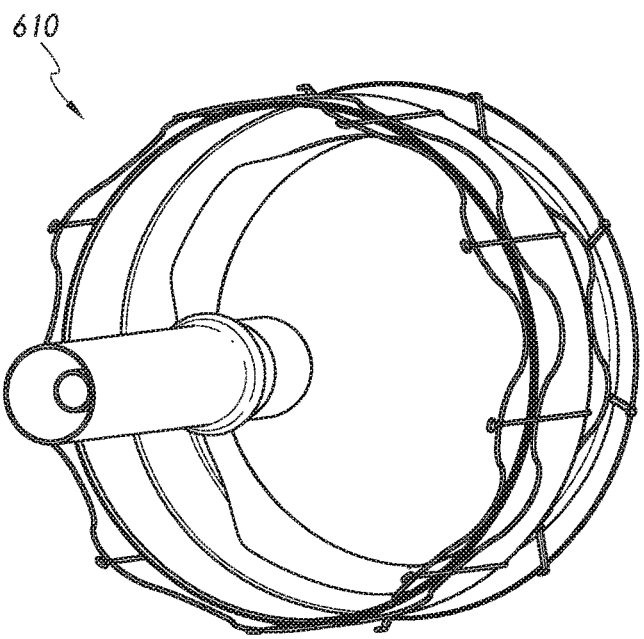
FIGS. 19A-C show isometric views of the functioning valve after it has been deployed.
Figure 19B:
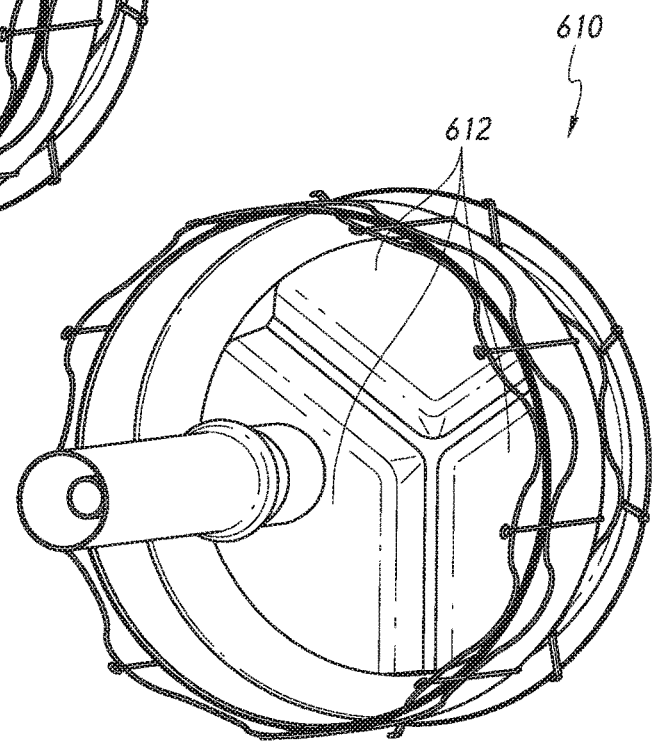
Figure 19C:
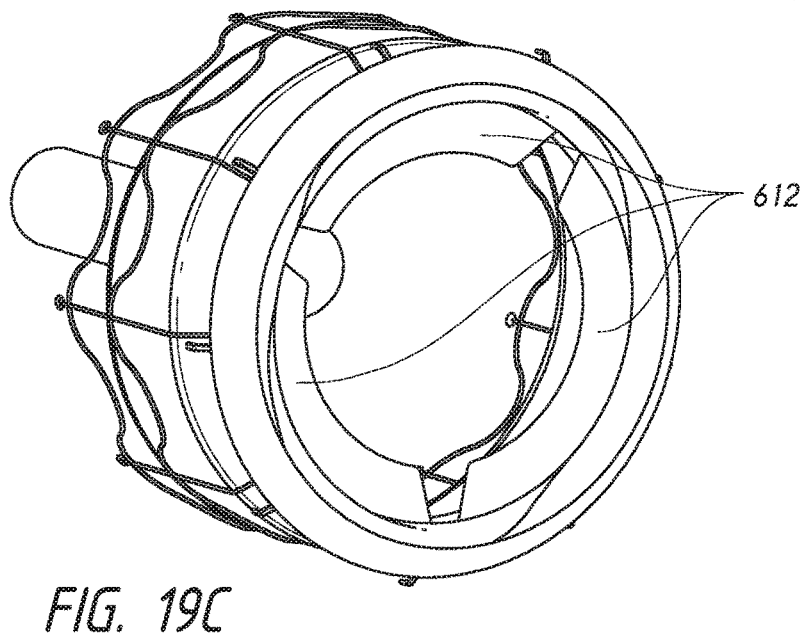

FIGS. 19A-C show alternative isometric views of the fully deployed prosthetic valve implant 610 with functioning valve leaflets 612. FIG. 19A shows the implant 610 from the in-flow side with the valve in the open position. FIG. 19B shows the implant 610 from the in-flow side with the valve in the closed position. FIG. 19C shows the implant 610 from the out-flow side with the valve leaflets partially closed 612 (mid-cycle).

Figure 1:
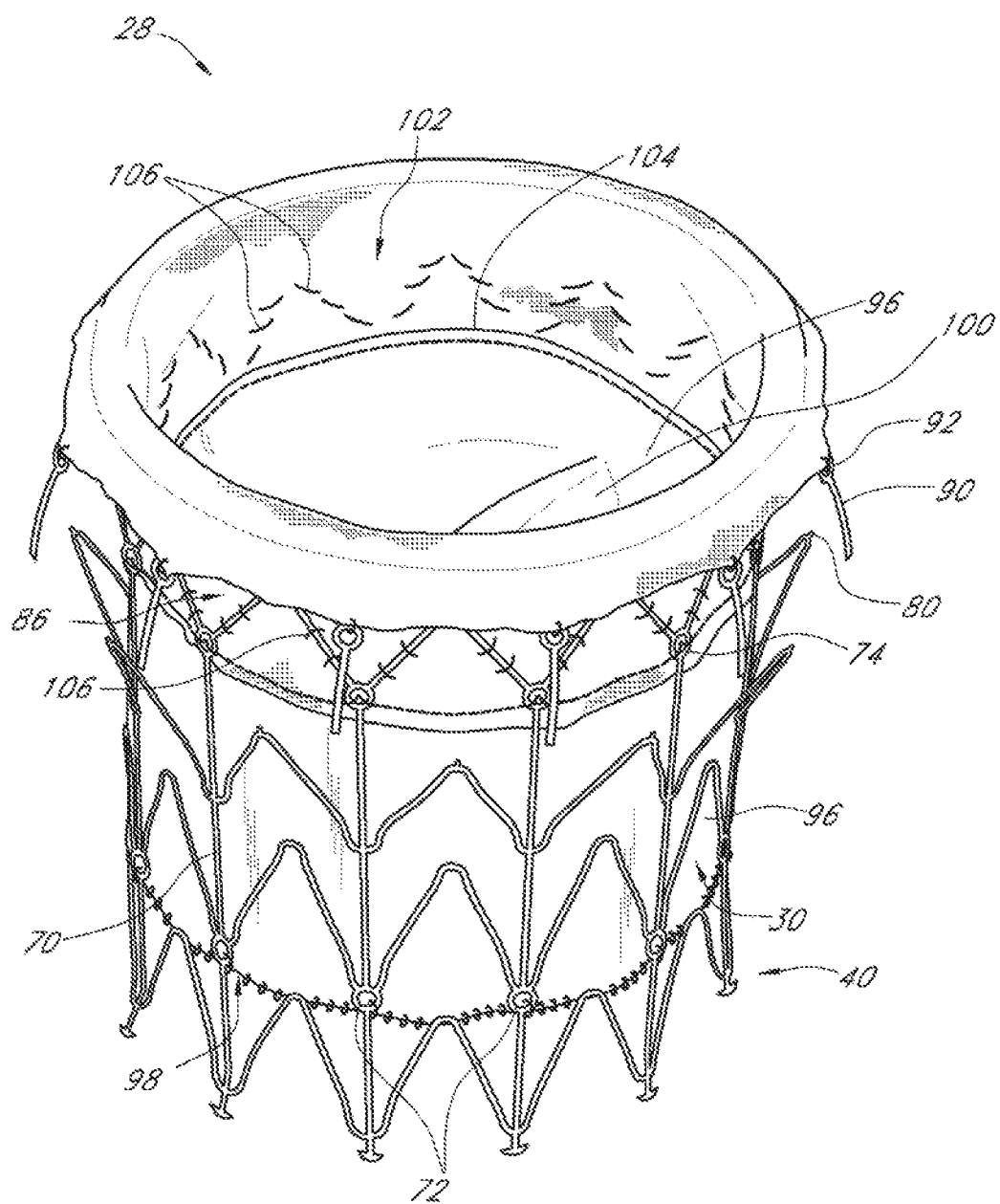
FIG. 1 is a perspective view of a heart valve implant having features in accordance with one embodiment.

With reference to FIGS. 1 and 2, another embodiment of a replacement heart valve 28 comprises a valve body 30 attached to a stent frame 40. In this embodiment, the heart valve body 30 is constructed of a tissue-based media such as bovine, equine and/or porcine pericardium. Vascular tissue, as well as other natural and manmade materials such as those described herein that are thin, flexible and durable, may also be employed for the heart valve body.

Figure 2A:
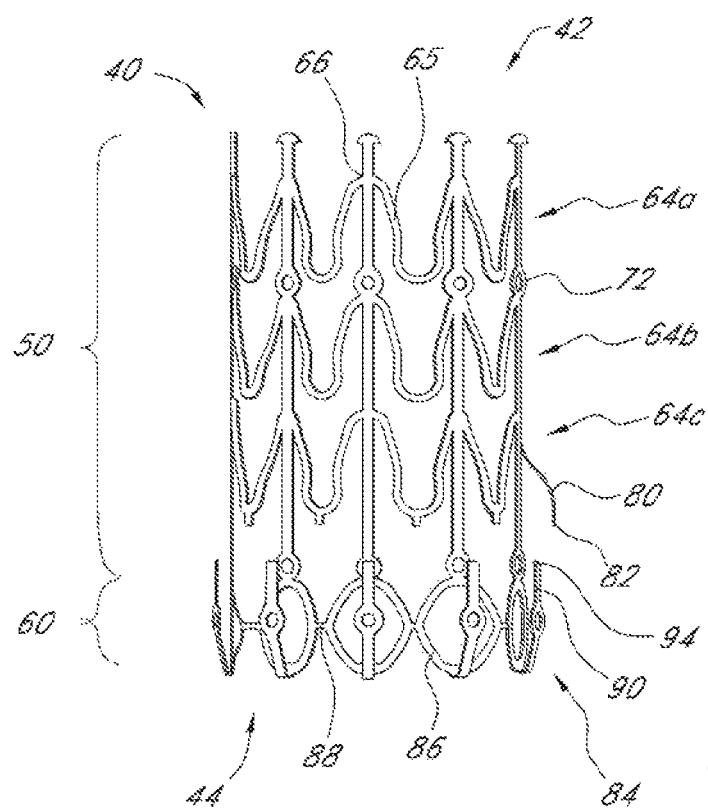
FIG. 2A is a plan view of a stent frame of the implant of FIG. 1 in a radially compacted configuration.
Figure 2B:
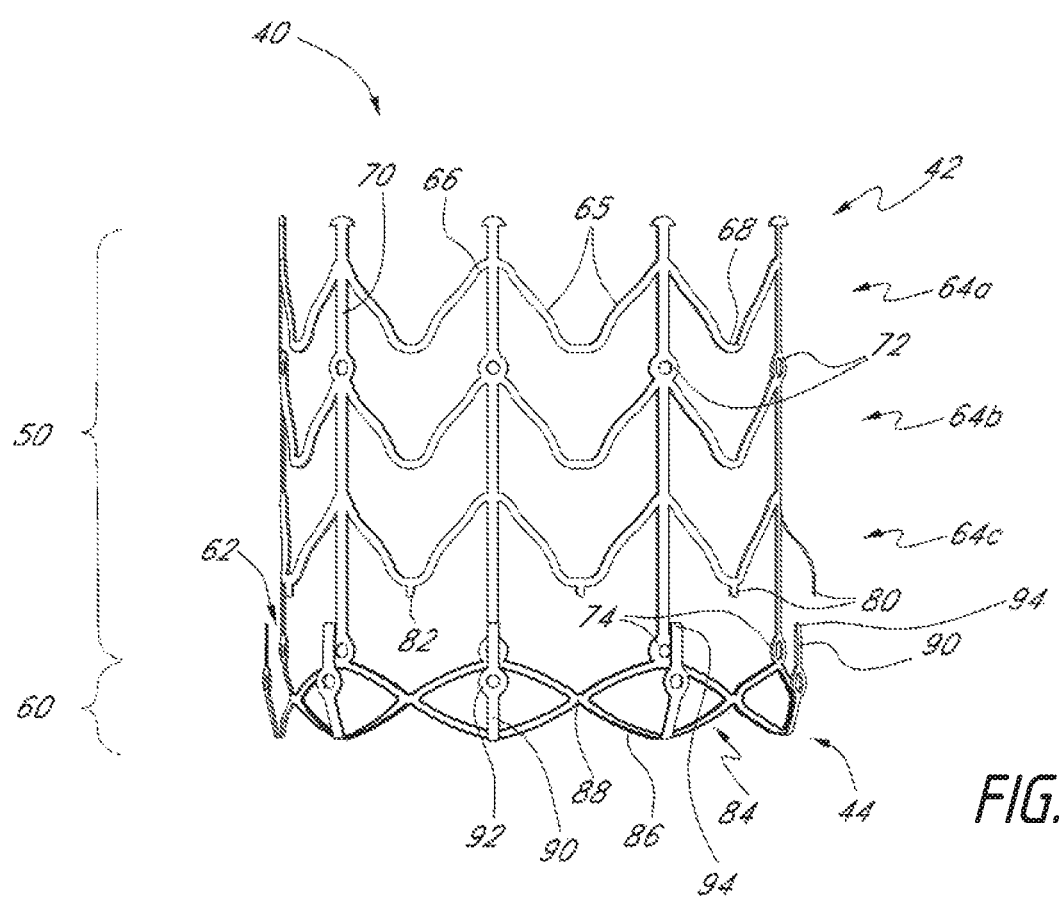
FIG. 2B shows the stent frame of FIG. 2A in a radially expanded configuration.
Figure 26A:
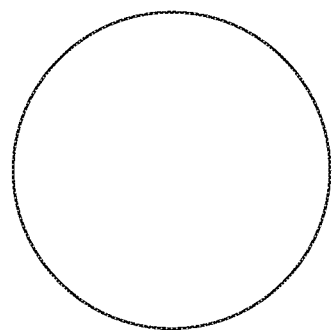
FIGS. 26A-C show three possible variations of the cross-sectional shape of the stent frame.
Figure 26B:
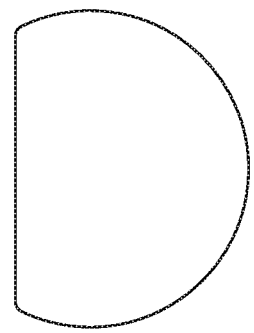
Figure 26C:
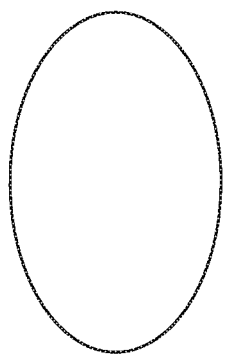

With particular reference to FIGS. 2A and 2B, the illustrated stent frame 40 embodiment supports the valve body 30 and can be expanded from a compacted state as shown in FIG. 2A to an expanded state as shown in FIG. 2B. The illustrated stent 40 preferably is a self-expanding stent constructed of a flexible material, preferably a shape memory material such as nitinol. However, as noted in U.S. Provisional Application No. 61/169,367, while a preferred embodiment of the stent frame is made from self-expanding nitinol material, it could also be made from a self-expanding polymer or a balloon expandable metallic material. As it is self-expanding, the stent 40 is in a fully opened state, as depicted in FIG. 2B, when relaxed. The illustrated stent 40 preferably is elongate from a first end 42 to a second end 44 and is tubular with a longitudinal axis 46 and a generally circular cross section. As noted in U.S. Provisional Application No. 61/169,367, although the preferred embodiment is a circular cross-section (see FIG. 26A) in order to keep the implant symmetric and minimize the need for radial adjustment during delivery, it is possible to form all or a portion of the stent body into a non-circular cross-section. It is to be understood that in other embodiments stents can have a non-circular cross section, such as a D-shape (see FIG. 26B), an oval (see FIG. 26C) or an otherwise ovoid cross-sectional shape. As noted in U.S. Provisional Application No. 61/169, 367, these are just two examples of non-circular cross-sections which may prove to be more advantageous, especially with respect to the atrio-ventricular position, in facilitating optimal engagement with the native valve annulus and minimizing the chance of paravalvular leaks.

The illustrated stent frame 40 has a non-foreshortening portion 50 and a foreshortening portion 60. The portions are joined at a transition 62 between the first and second ends 42, 44. Foreshortening refers to a behavior in which the length of the stent 40 in the foreshortening portion 60 decreases as the radius of the stent increases from the compacted state to the expanded, deployed state. As such, in FIG. 2A, which shows the stent frame 40 in a compacted state, the foreshortening portion 60 of the stent frame 40 is longer than when the stent is in the expanded state illustrated in FIG. 2B.

With continued reference to FIG. 2B, the non-foreshortening portion 50 of the illustrated stent 40 comprises a plurality of rows or rings 64*a-c* of circumferentially expansible elements, or struts 65, arranged in a zigzag pattern. The struts 65 are configured to expand and contract with a change in radius of the stent 40. In the illustrated embodiment, the stent has three such rings 64*a-c*. It is to be understood that more or fewer rings can be employed as desired to accomplish the purposes of this stent frame.

In the illustrated embodiment, the respective ends of each circumferential undulating strut 65 join an adjacent strut 65 at an apex 66, 68 which is, in at least some embodiments, an area of preferential bending. In the illustrated embodiment, the zigzag pattern of the rings 64*a-c* are generally in phase with one another. It is to be understood that, in other embodiments, all or most of the rings can be in phase with one another or out of phase as desired.

With continued reference to FIG. 2B, longitudinal struts 70 extend transversely across the rings 64*a-c* of the non-foreshortening portion 50 from the first end 42 of the frame 40 to the transition 62. More particularly, each ring 64 shares a common longitudinal strut 70. The longitudinal struts 70 extend through apices 66 of adjacent rings 64, and preferably extend the entire length of the nonforeshortening portion 50. Preferably, the longitudinal struts 70 comprise a nonexpandable rod or bar. The apices 66 that are connected to the longitudinal struts 70 are referred to as "connected" apices 66. Apices 68 not connected to longitudinal struts 70 are referred to as "free" apices 68.

As noted above, the longitudinal struts 70 are not substantially expandable in a longitudinal direction. As such, even though the undulating struts 65 provide flexibility in radial expansion or compaction, as the stent 40 changes radial size between the compacted and expanded states, the longitudinal length of the stent in the nonforeshortening portion 50 remains substantially unchanged. In other embodiments, the longitudinal struts may include expansible elements that may allow the struts to expand somewhat longitudinally. However, such longitudinal expansion would not be directly tied to any change in strut radius.

In the illustrated embodiment, a first ring 64*a* is disposed adjacent the first end 42 of the stent and a second ring 64*b* is disposed adjacent the first ring 64*a*. A set of first eyelets 72 is formed at the connected apices 66 of the second ring 64*b*. A set of second eyelets 74 is also formed at the second ends of each longitudinal strut 70, which in the illustrated embodiment is also at the transition 62. In a third ring 64*c*, the free apices 68 each comprise a protuberance 80 extending therefrom, which protuberance can also be referred to as an apical anchor 80. Preferably the apical anchor 80 terminates at a tip 82. Preferably the struts 65 in the third ring 64*c* are pre-shaped so as to flare radially outwardly when the stent frame 40 is in an expanded state as shown in FIGS. 1 and 2.

With continued reference to FIGS. 2A and 2B, the foreshortening portion 60 of the illustrated stent frame 40 comprises a ring 84 of generally diamond-shaped cells 86 connected to one another at connectors 88. A first end of each cell 86 is connected to the nonforeshortening portion 50 at the second eyelets 74. The shape of the foreshortening cells 86 is such that as the stent frame 40 is radially compacted, the foreshortening portion 60 of the stent becomes longitudinally longer and, correspondingly, when the stent frame 40 is expanded radially, the foreshortening portion 60 shortens.

A second end of each cell 86 in the foreshortening portion 60 defines the second end 44 of the stent 40 and also defines a base of an end anchor 90 that extends generally radially outwardly and toward the first end 42 of the stent. An anchor eyelet 92 is formed in each end anchor 90, preferably between the base and a tip 94 of each anchor 90.

A first distance is defined between the tips 82, 94 of opposing apical and end anchors 80, 90 when the stent 40 is in the compacted state, and a second distance is defined between the tips 82, 94 of opposing anchors 80, 90 when the stent 40 is in the expanded state. As shown, the second distance is substantially less than the first distance. As such, due to longitudinal shortening of the foreshortening portion 60, the anchors 80, 90 cooperate to grasp onto tissues so as to hold the stent in place.

In preferred embodiments, the stent 40 may be deployed into a heart valve annulus, and positioned when compacted so that the tips 82, 94 of the opposing anchors 80, 90 are disposed on opposite sides of the native annulus. As the stent is expanded, the opposing anchors are drawn closer together so as to grasp opposite sides of the native annulus and securely hold the stent in position. As such, the stent can be held securely in position without requiring a substantial radial force against the native annulus.

Applicant's U.S. patent application Ser. No. 12/084,586, which was published on Aug. 27, 2009 as U.S. Publication No. 2009/0216314, discusses embodiments of foreshortening stents with anchors, and can be referred to for further discussion of certain aspects of the illustrated stent embodiment. The discussion in this application concerning structure and operation of embodiments of a foreshortening stent, particularly a foreshortening stent having anchors, is expressly incorporated by reference herein.

Applicant's U.S. patent application Ser. No. 12/569,856, which was published on Apr. 1, 2010 as U.S. Publication No. 2010/0082094, discusses several additional embodiments of stents and associated valve bodies, and can be referred to for further explanation and discussion of additional features and embodiments thereof. The entirety of this application is also expressly incorporated by reference herein.

With particular reference again to FIG. 1, in this embodiment the valve body 30 is disposed inside the stent 40. More specifically, a skirt portion 96 of the valve body 30 is sewn to the first eyelets 72 of the stent. A hemmed upstream end of the valve body 30 engages the first eyelets 72 in the nonforeshortening portion 50 of the stent 40. Valve leaflets are attached to the skirt portion and are configured to open and close during valve operation.

An elongate tubular portion 102 of flexible, longitudinally expandable fabric is attached to a downstream end 104 of the skirt portion 96 in the illustrated embodiment. More particularly, a first end of the fabric 102 is sewn to the downstream end 104 of the skirt portion about the circumference of the skirt portion by a downstream seam, which also connects to the second eyelets 74 of the stent frame 40. Preferably, the fabric 102 is also sewn to the foreshortening cells 86 at several points by connector stitches 106.

In the illustrated embodiment, the fabric 102 curves around the second end of the stent frame 40, generally following the curvature of the end anchors 90. A second end of the fabric portion 102 is sewn to the anchor eyelets 92. Preferably, the flexible fabric 102 is sufficiently expandable to move with the foreshortening portion 60 as the stent 40 moves between the compacted state and the deployed, relaxed expanded state. As such, in the illustrated embodiment, the tissue valve body 30 is confined to the nonforeshortening portion 50 of the stent and the flexible fabric 102 spans the foreshortening portion 60 of the stent. Thus, the tissue valve body 30 is not subject to longitudinal expansion and contraction with the stent 40.

Figure 3:
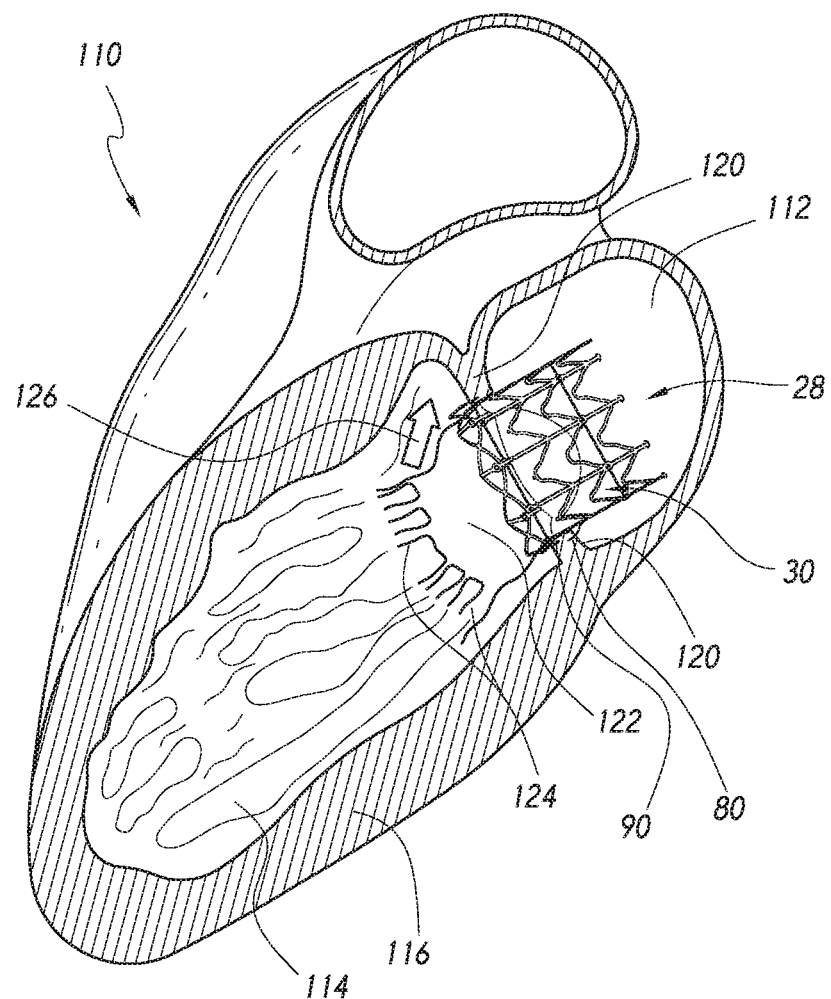
FIG. 3 schematically shows an implant as in FIGS. 1-2 deployed in a native mitral annulus of a human heart.

With reference next to FIG. 3, a schematic representation of the heart valve 28 as discussed above in connection with FIGS. 1 and 2 is depicted installed in a human heart 110. The heart is shown in cross-section, and represents typical anatomy, including a left atrium 112 and left ventricle 114. The left ventricle 114 is defined by a muscular wall 116. The left atrium 112 and left ventricle 114 communicate with one another through a mitral annulus 120. Also shown schematically in FIG. 3 is a native anterior mitral leaflet 122 having chordae tendinae 124 that connect a downstream end of the anterior mitral leaflet 122 to the muscle wall 116 of the left ventricle 114. A left ventricle outflow tract 126 extends toward the top of the left ventricle 114.

As shown in FIG. 3, the valve 28 of FIGS. 1 and 2 is disposed so that the mitral annulus 120 is grasped between the end anchors 90 and apical anchors 80 in accordance with a method of aligning and deployment of the stent 40 discussed previously. As such, all or most of the stent 40 extends into the left atrium. The portion of the stent 40 disposed upstream of the annulus 120 can be referred to as being positioned supra-annularly. The portion generally within the annulus 120 is referred to as positioned intra-annularly. The portion downstream of the annulus is referred to as being positioned sub-annularly. In the illustrated embodiment, only a part of the foreshortening portion is positioned intra-annularly or sub-annularly, and the rest of the stent 40 is supra-annular.

In the illustrated embodiment, the anterior mitral leaflet 122 has not been removed prior to deploying the replacement valve 28. Preferably, the posterior mitral leaflet (not shown) also has not been removed prior to deploying the replacement valve. However, in other embodiments, one or both of these natural valve leaflets may be removed before deploying the replacement valve.

Figure 20A:
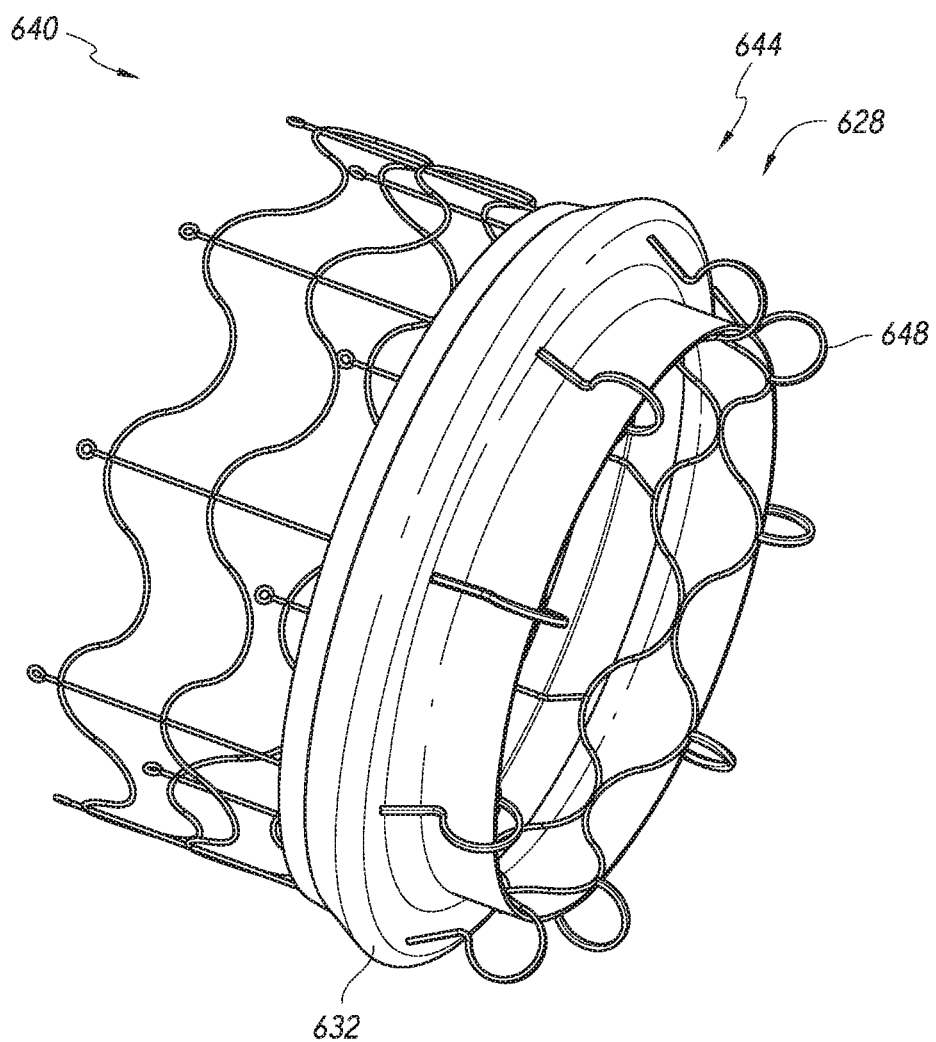
FIG. 20A shows a perspective view of the expanded stent frame with fabric-liner and with an alternative bend configuration of the anchor features.
Figure 20B:
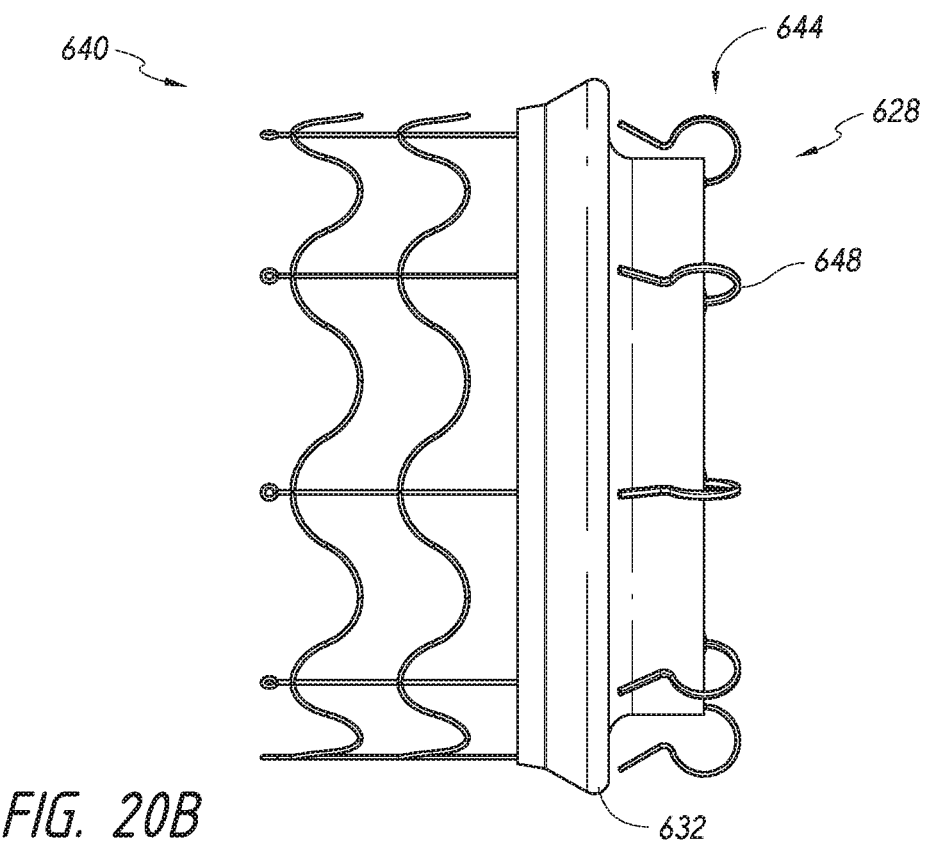
FIG. 20B shows a side view of the expanded stent frame of FIG. 20A.
Figure 20C:
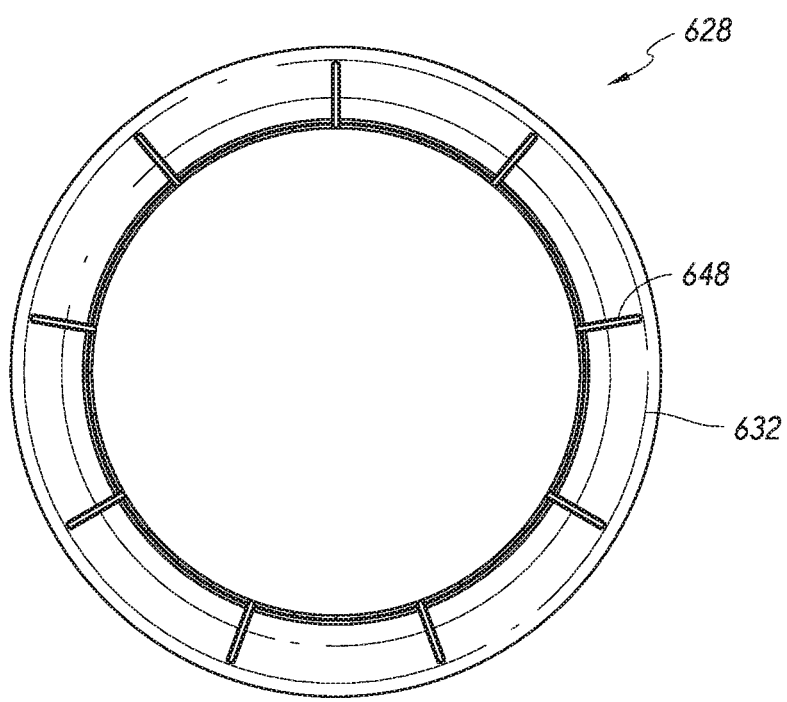
FIG. 20C shows a front view of the expanded stent frame of FIG. 20A.

As discussed in U.S. Provisional Application No. 61/169, 367, FIGS. 20A-20C show multiple views of a stent frame 640 and fabric liner sub-assembly 632 with an alternative anchor feature 648 configuration. In this embodiment, the anchor features 648 incorporate a bulge feature that, in the case of atrio-ventricular valve replacement, may help direct the native valve leaflets and subvalvular apparatus away from the distal tips of the anchor features 648 prior to attachment. In addition, the larger radius of curvature between the lower portion 644 of the stent frame 640 and the anchor features 648 that is created by the bulge feature may help to distribute forces and reduce stress in that region.

Figure 21:
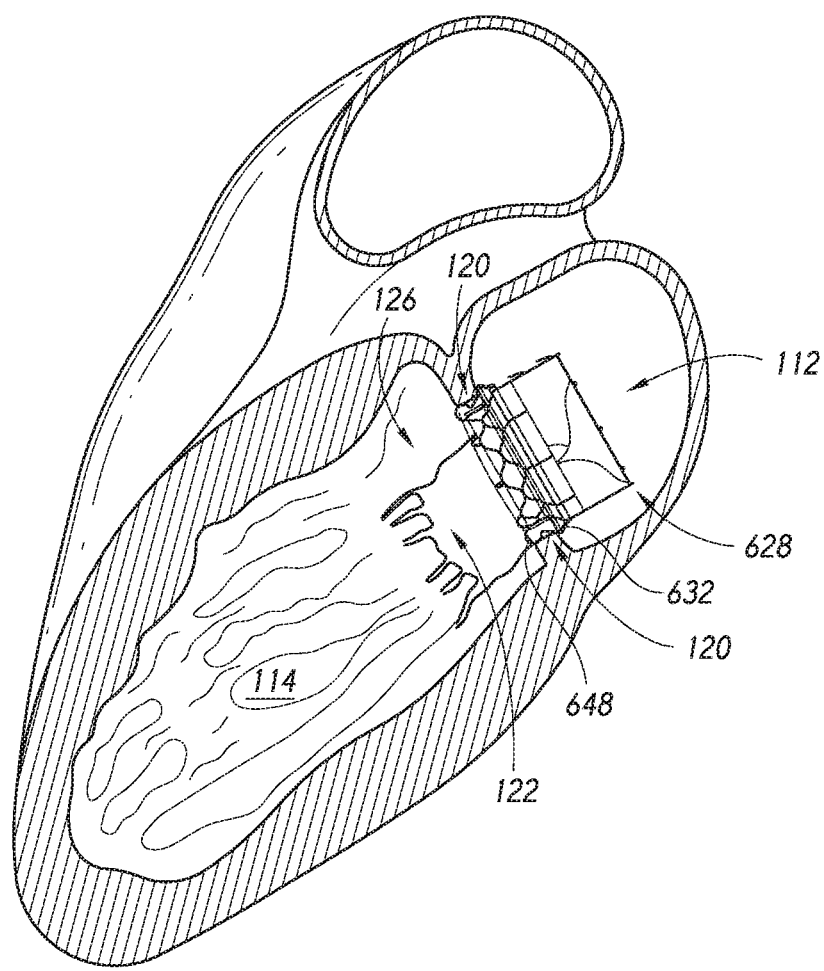
FIG. 21 shows a cross-section view of another embodiment as it would be positioned and anchored in the mitral valve annulus.

FIG. 21 illustrates a lateral, cross-sectional view of the heart showing the embodiment of the prosthetic heart valve implant 628 positioned between the left atrium 112 and the left ventricle 114 with the mitral valve annulus 120 captured between the transition shoulder 646 on the atrial side and the anchor features 648 on the ventricular side. The anterior leaflet 122 of the mitral valve is also depicted and specific attention is drawn to the left ventricular outflow tract 126 to show that it is not obstructed by the presence of the prosthetic heart valve implant 628.

Figure 22A:
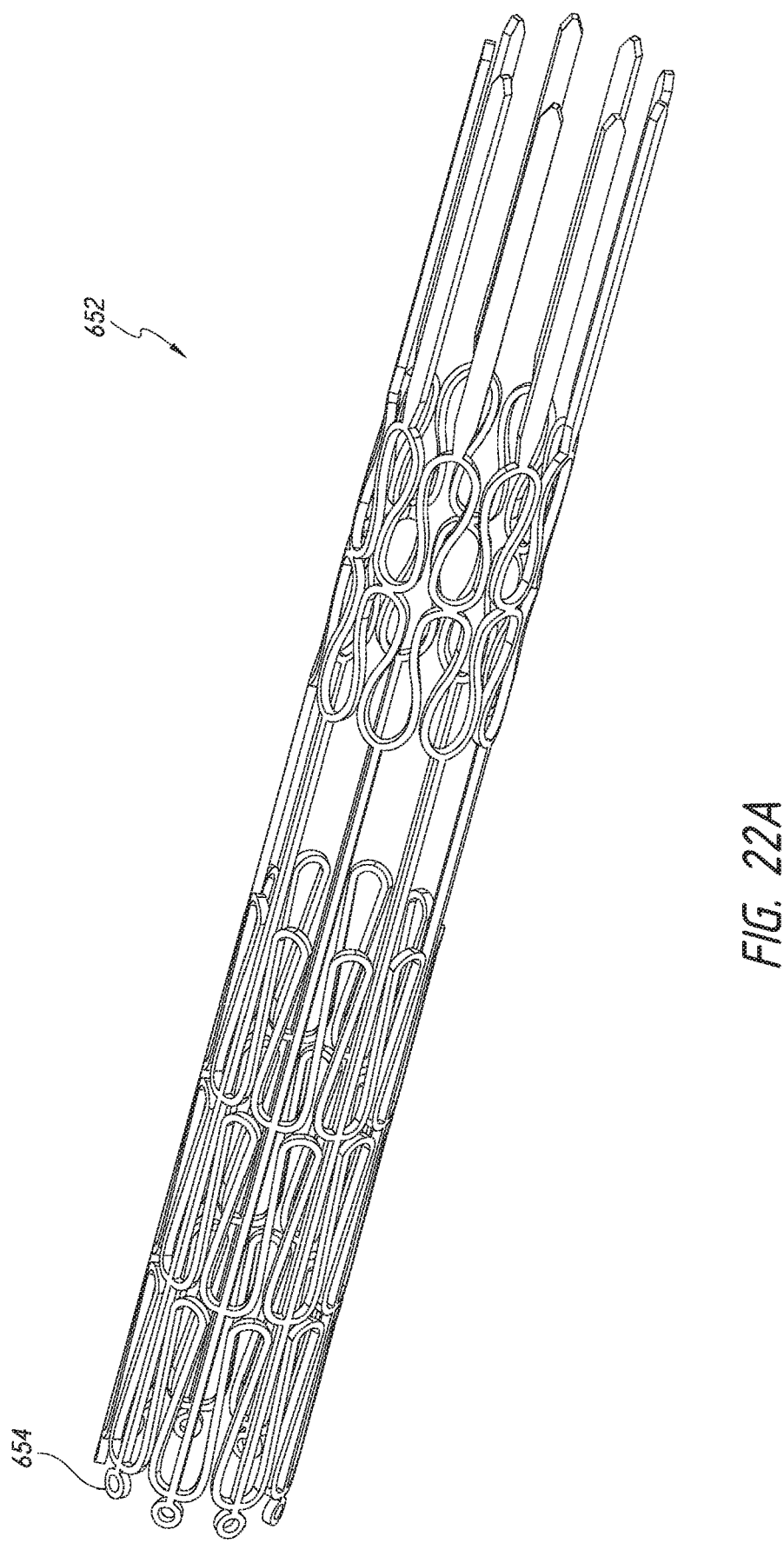
FIG. 22A shows the strut geometry of a stent frame in the pre-expanded condition after the pattern has been laser cut into a tube.
Figure 22B:
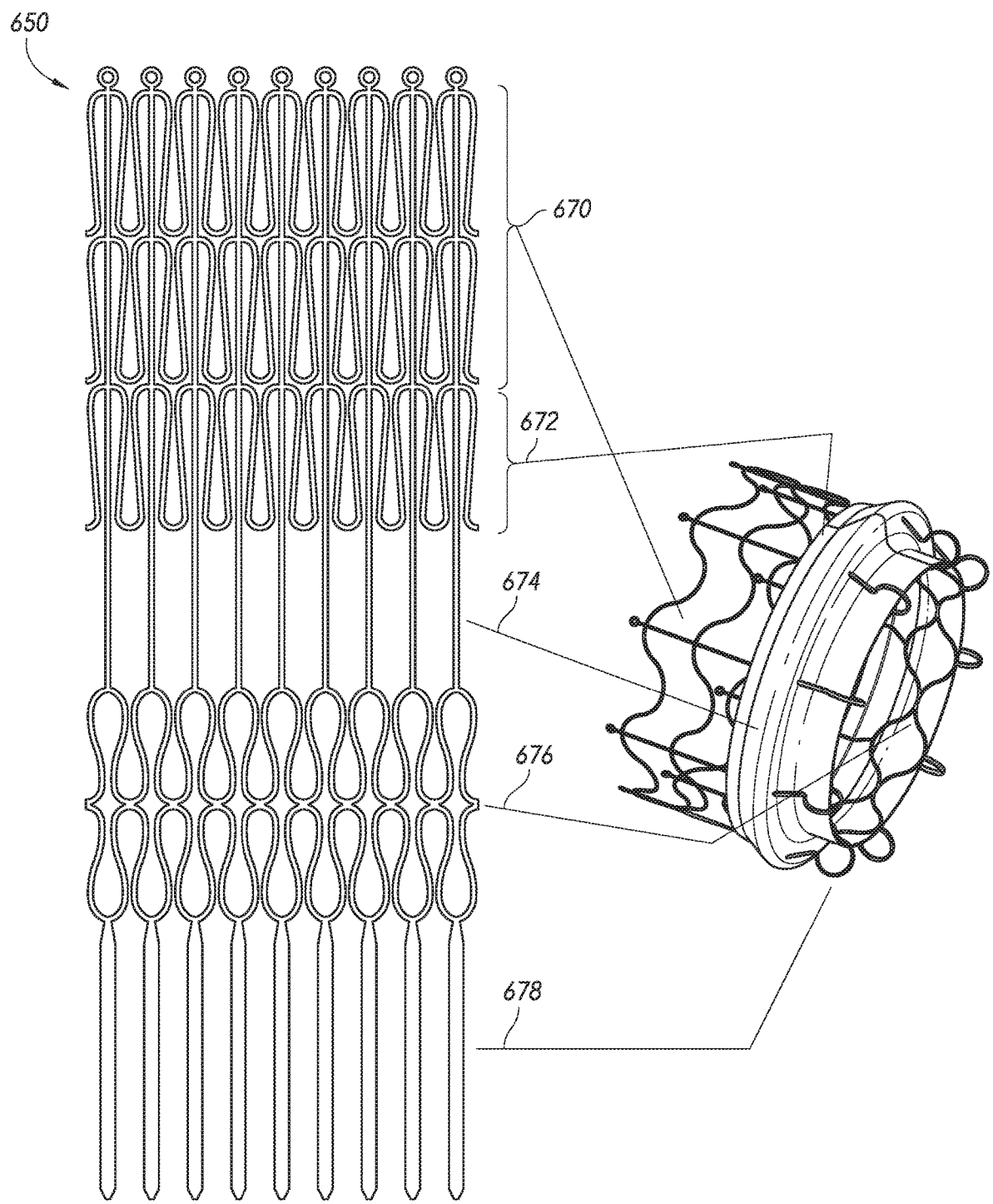
FIG. 22B shows the stent of FIG. 22A in both a flat pattern and expanded configurations to describe the various regions of the stent frame geometry.
Figure 23A:
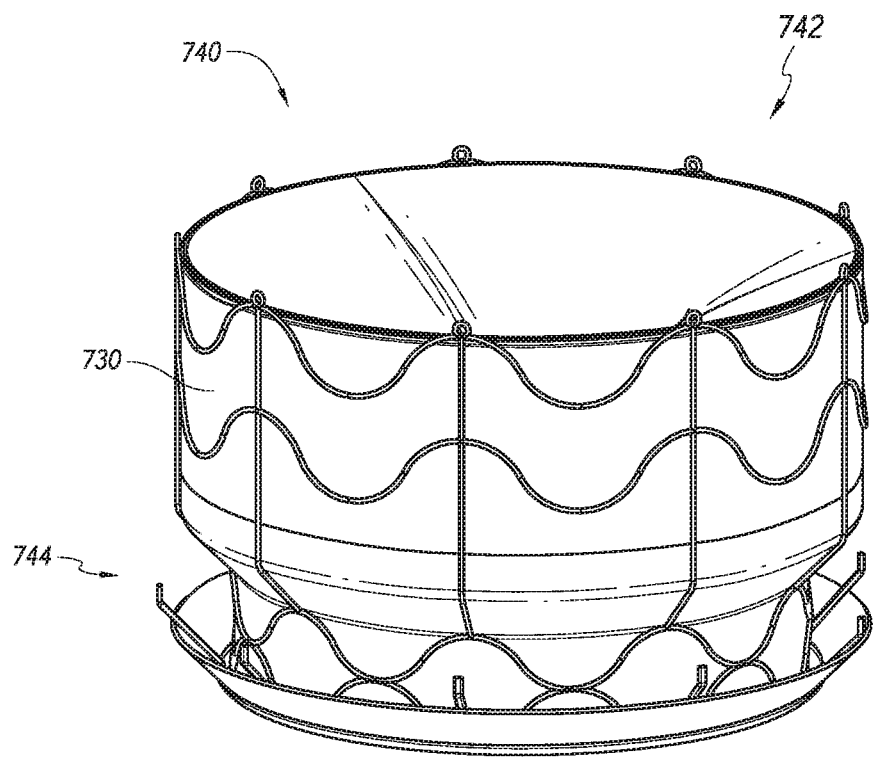
FIG. 23A shows a first perspective view of one embodiment of the prosthetic heart valve assembly with the valve positioned in the upper portion of the stent frame.
Figure 23B:
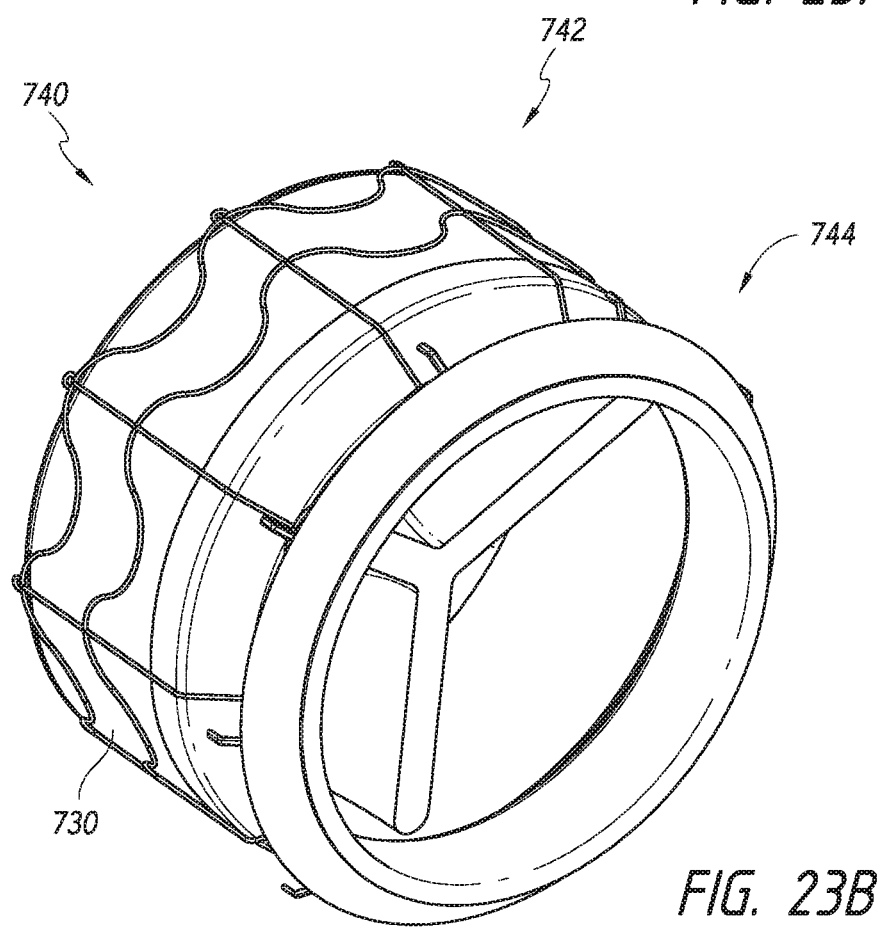
FIG. 23B shows a second perspective view of the embodiment of FIG. 23A.
Figure 23C:
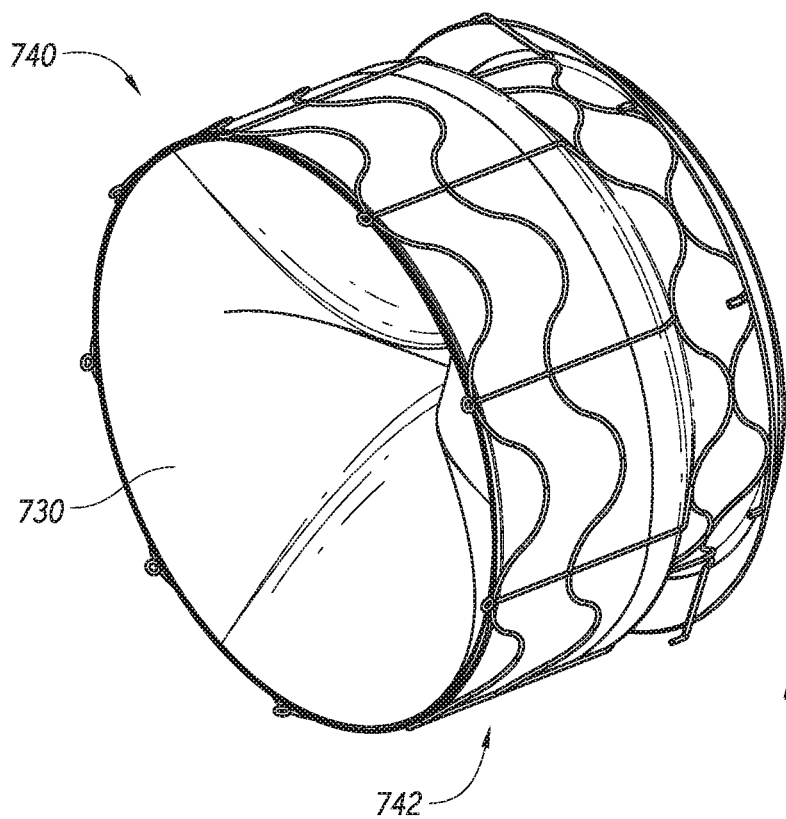
FIG. 23C shows a third perspective view of the embodiment of FIG. 23A.
Figure 23D:
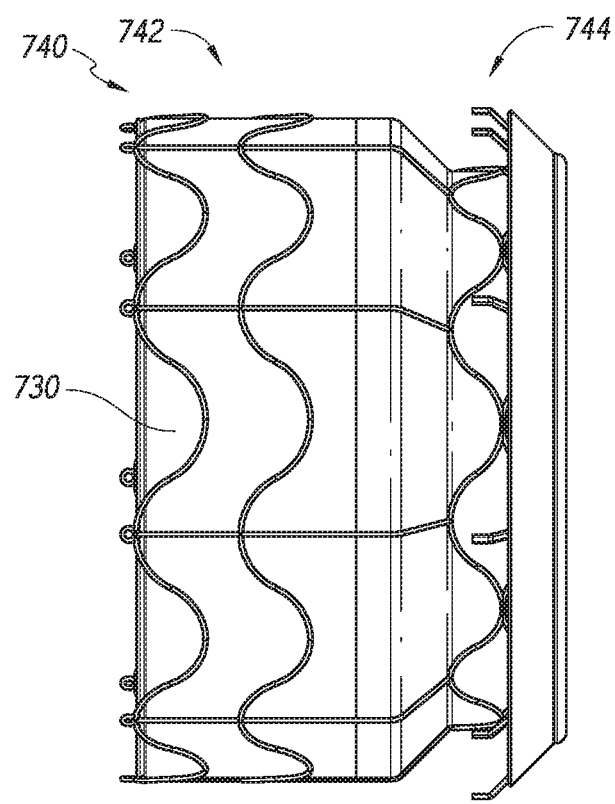
FIG. 23D shows a side view of the embodiment of FIG. 23A.
Figure 24A:
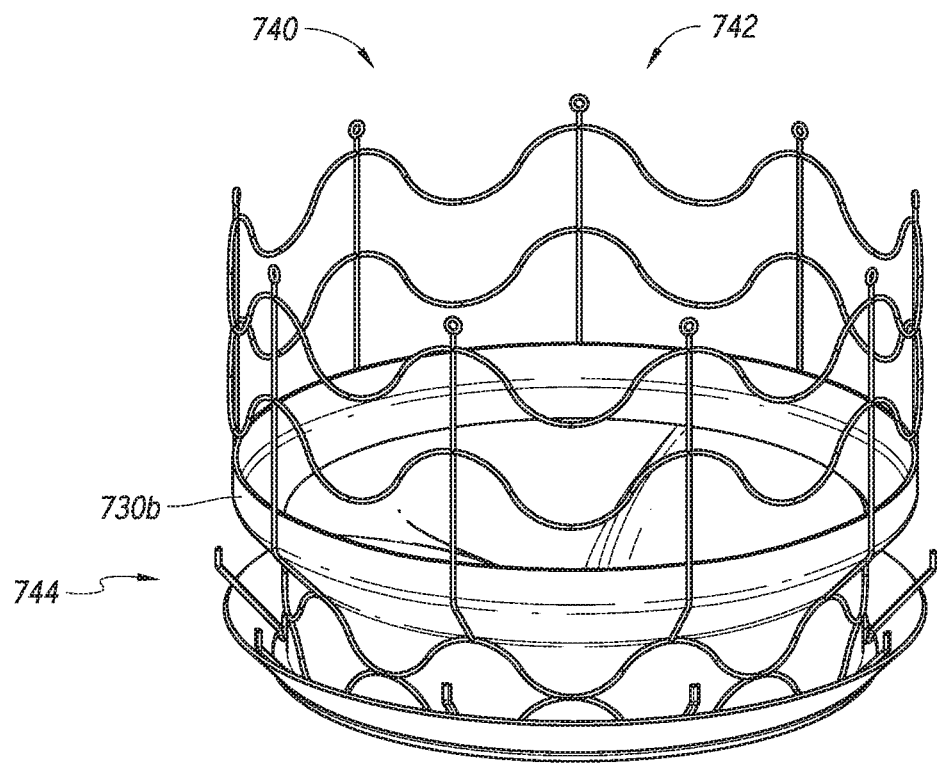
FIG. 24A shows a first perspective view of one embodiment of the prosthetic heart valve assembly with the valve positioned entirely in the lower portion of the stent frame.
Figure 24B:
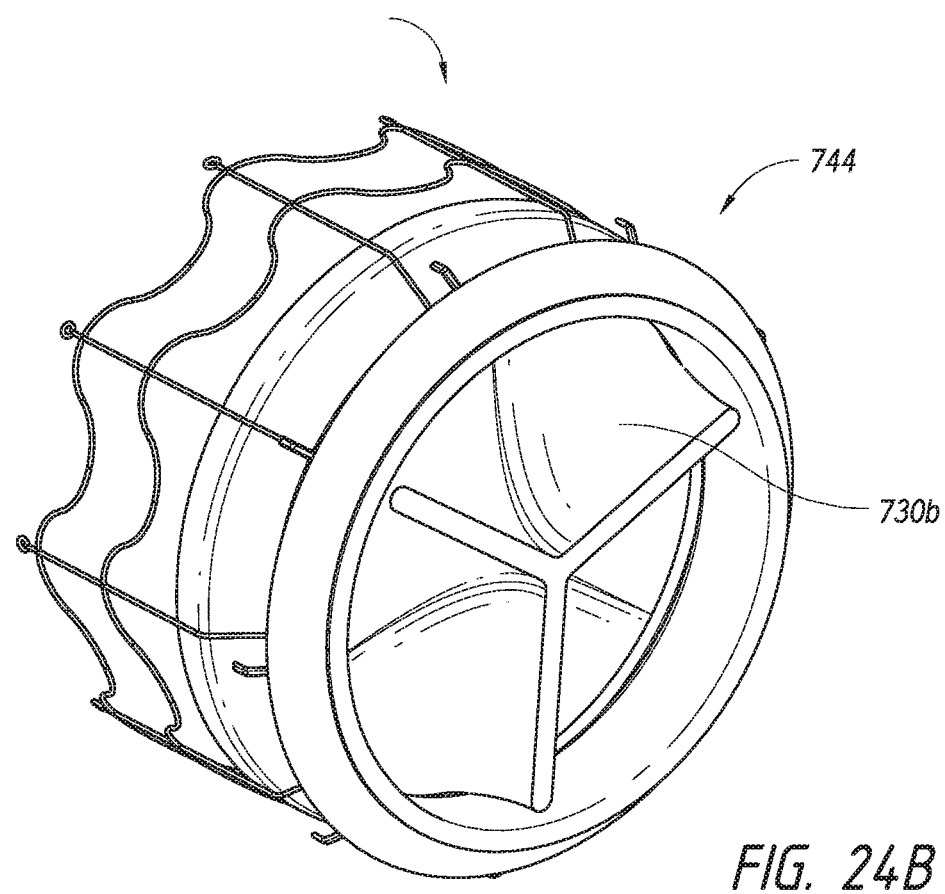
FIG. 24B shows a second perspective view of the embodiment of FIG. 24A.
Figure 24C:
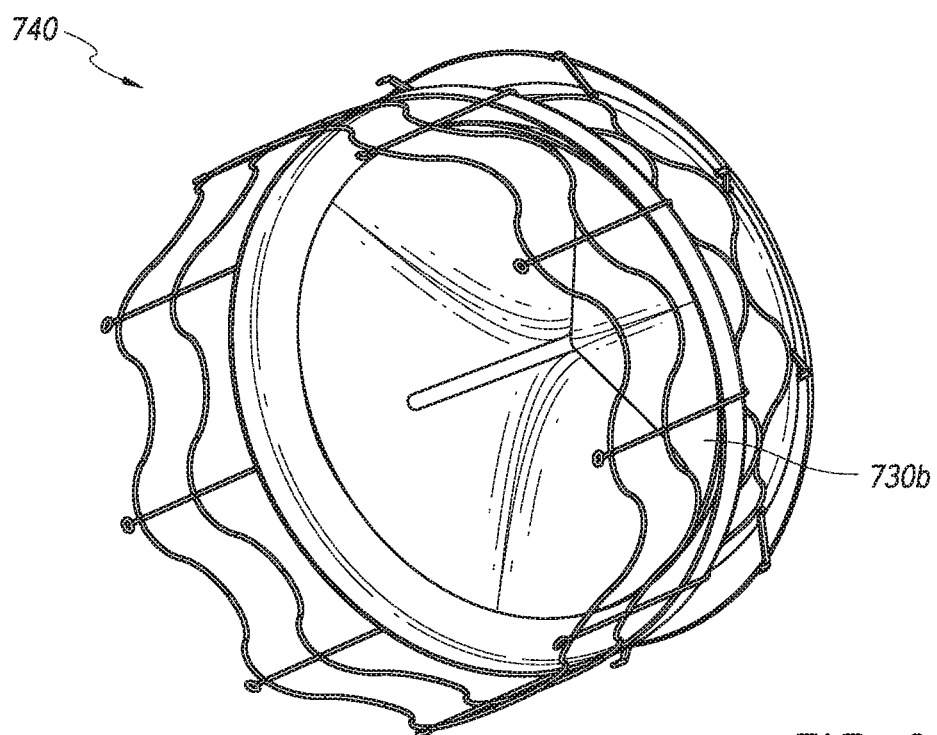
FIG. 24C shows a third perspective view of the embodiment of FIG. 24A.
Figure 24D:
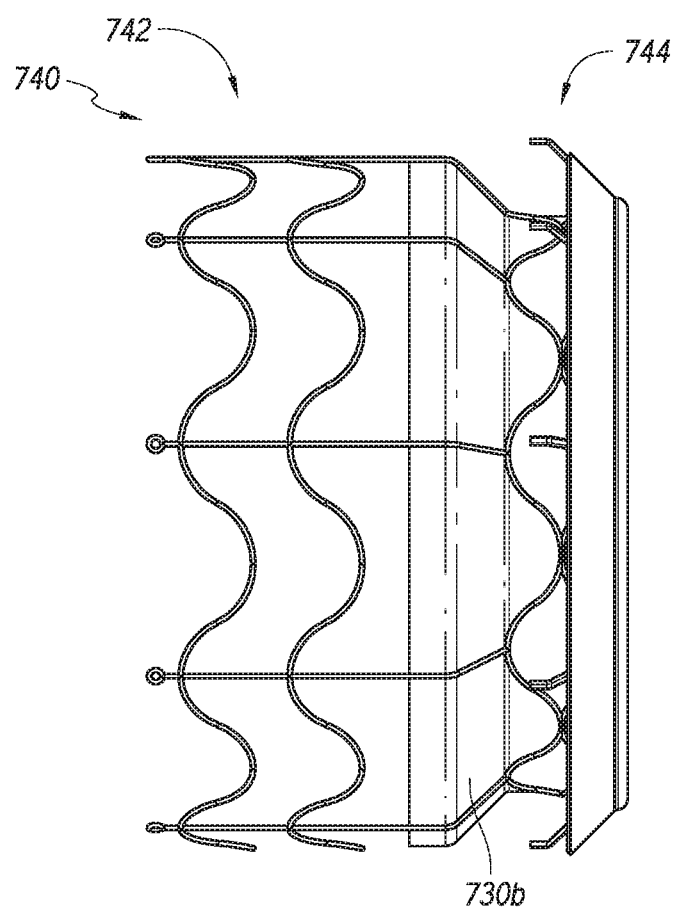
FIG. 24D shows a side view of the embodiment of FIG. 24A.
Figure 25A:
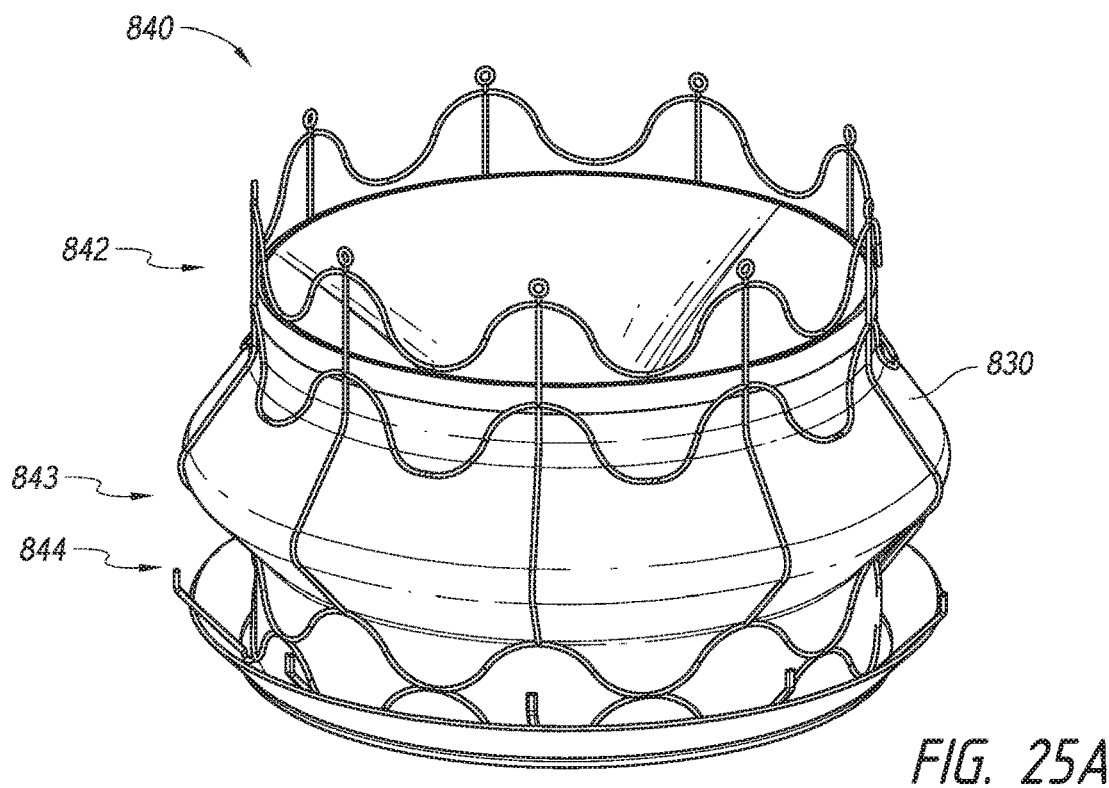
FIG. 25A shows a first perspective view of one embodiment of the prosthetic heart valve assembly with the valve positioned between the upper and lower portions of the stent frame and a flared diameter in the stent frame at the transition between the upper and lower portions.
Figure 25B:
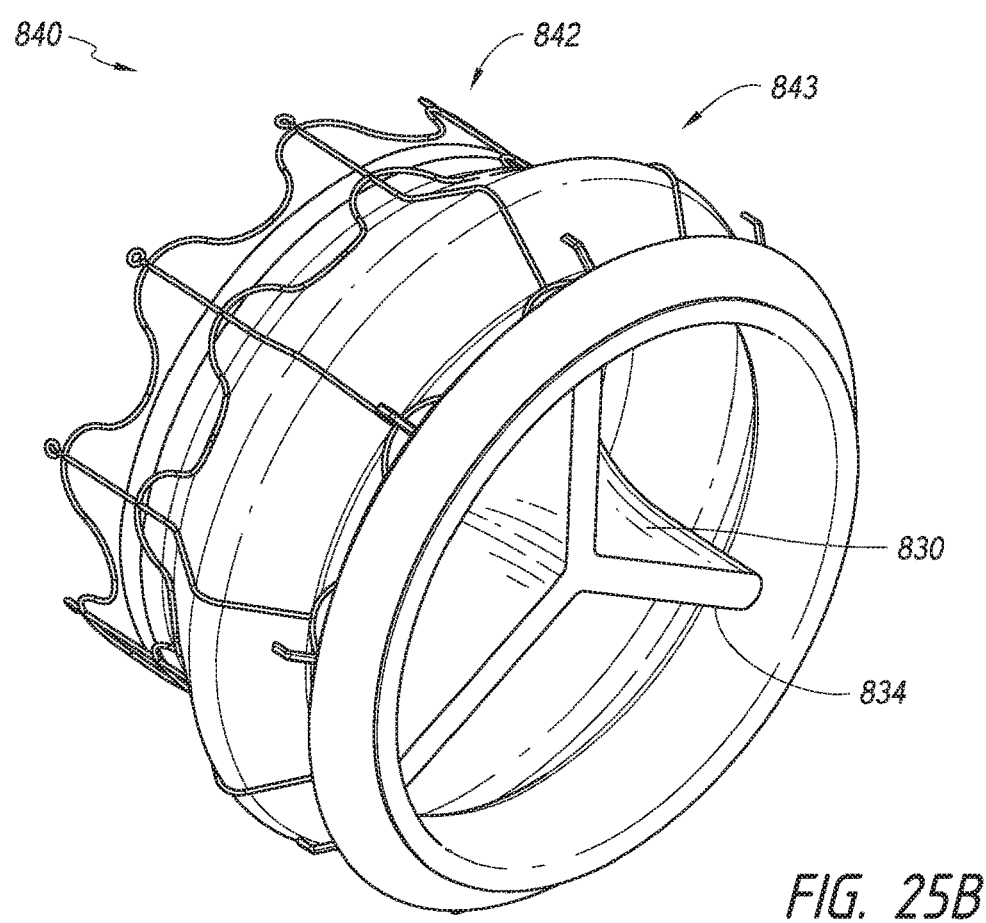
FIG. 25B shows a second perspective view of the embodiment of FIG. 25A.
Figure 25C:
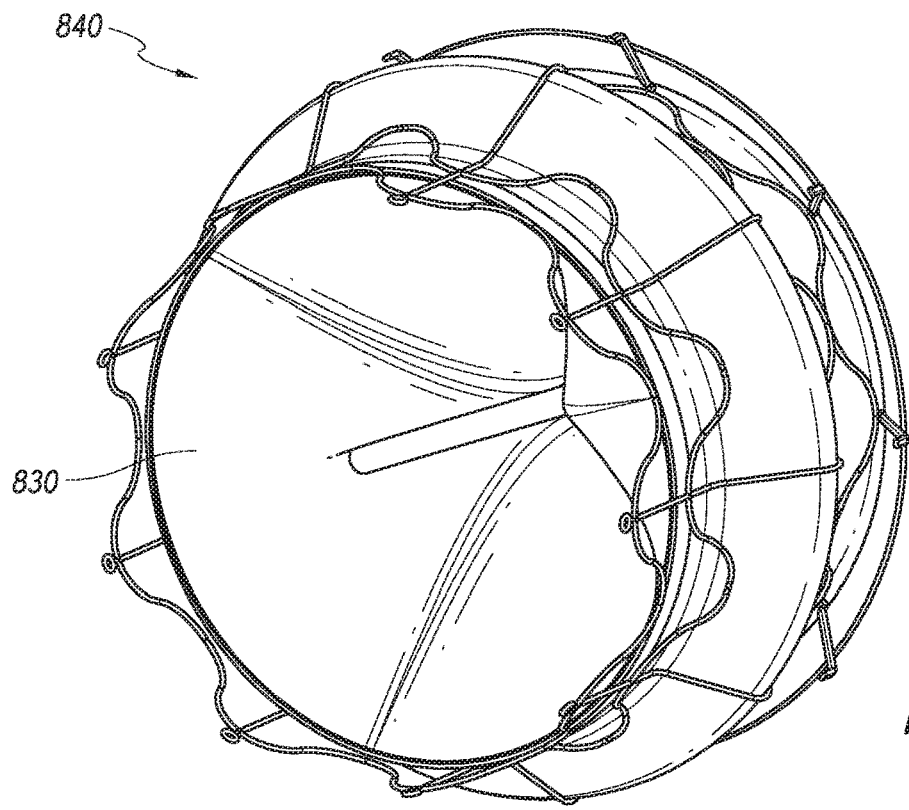
FIG. 25C shows a third perspective view of the embodiment of FIG. 25A.
Figure 25D:
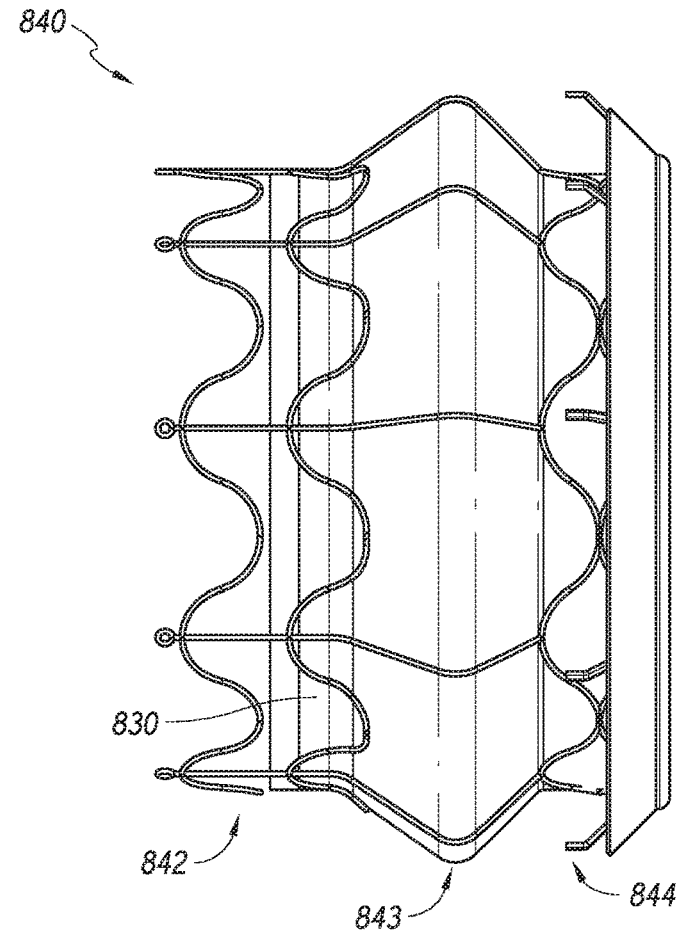
FIG. 25D shows a side view of the embodiment of FIG. 25A.

As shown in U.S. Provisional Application No. 61/169, 367, FIGS. 22A and 22B show a stent frame, such as stent frame 640, in its pre-expanded condition after the strut pattern 650 has been laser cut into a tube 652. It also highlights the locking loop features 654 on the upper edge of the stent frame which engage with mating features on a support tube of the delivery device and are used to maintain control over the implant during the delivery process and prior to final deployment and release. FIG. 22B shows a flat pattern 650 of the same strut geometry as if the stent frame in FIG. 22A were un-rolled. An expanded version of the same stent frame (with a fabric liner) is also shown in FIG. 22B with the various sections of the stent frame numbered and labeled. Section 670 indicates the upper tissue valve portion or area of the stent frame. Section 672 shows an optional group of struts for this embodiment intended to provide additional support the transition shoulder, such as shoulder 646, or flare region or section depending on the configuration. Section 674 points out the flare radius and flat lip section. In other embodiments this would also refer to the transition shoulder. In both cases, this region of the stent frame is meant to engage the top side of the valve annulus. Section 676 is the lower connection portion or section of the stent frame which provides foreshortening and axial clamping as the stent frame expands radially. Section 678 refers to the anchor features, such as anchor features 648, which can be bent and formed to a variety of configurations after the flat pattern 650 is cut. As shown in the illustrated embodiment, the anchors are bent back with bulge and tip.

Figure 4A:
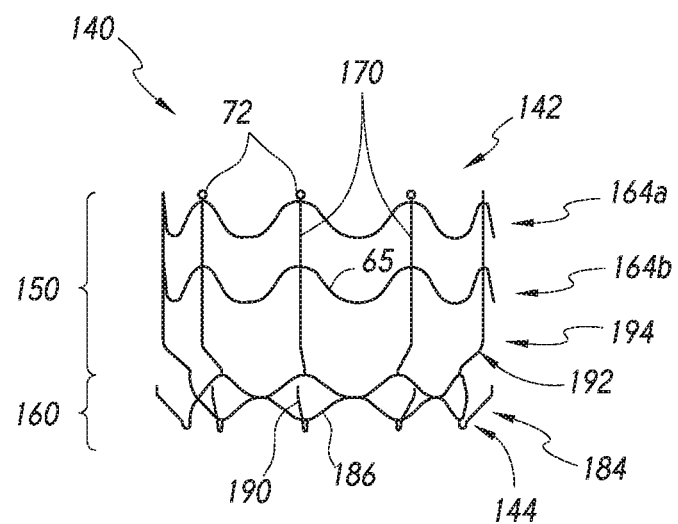
FIG. 4A is a plan view of a stent frame configured in accordance with another embodiment.
Figure 4B:
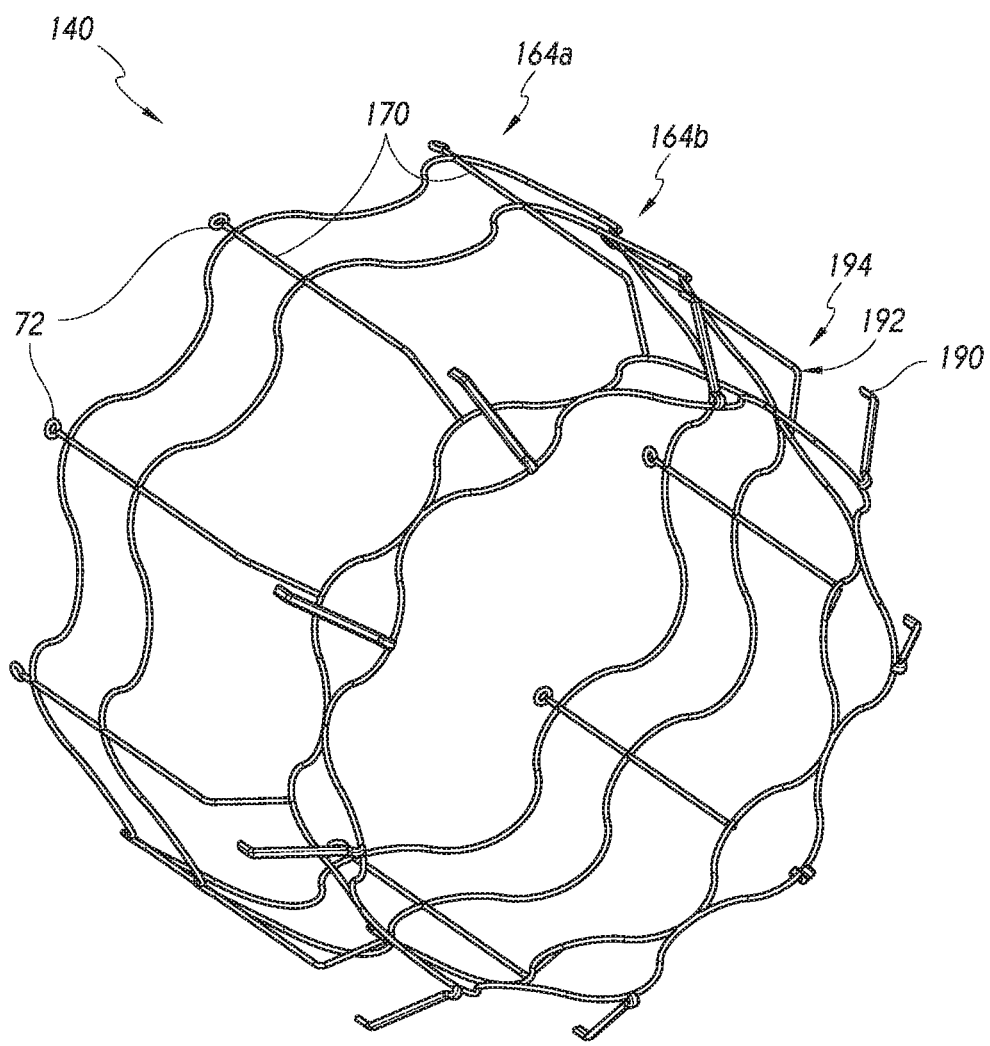
FIG. 4B shows an isometric view of an embodiment of the expanded stent frame.

With reference next to FIGS. 4A and 4B, another embodiment of a stent frame 140 is illustrated. The stent frame 140 is elongate and has opposing first and second ends 142, 144.

A first circumferential ring 164*a* comprising undulating struts is arranged adjacent the first end 142. A second circumferential ring 164*b* of undulating struts is disposed adjacent the first circumferential ring 164*a*. A circumferential foreshortening ring 184 comprised of interconnected generally diamond-shaped foreshortening cells 186 is disposed generally adjacent the second end 144. A plurality of longitudinal struts 170 extend from the first end 142 toward the second end and terminate at a connection to corresponding foreshortening cells 186. Preferably, the longitudinal struts 170 pass through the undulating rings 164 and connect to apices of the rings 164. Preferably a locking member is formed on each longitudinal strut 170 at the first end 142. In the illustrated embodiment the locking members comprise eyelets 72.

Anchors 190 extend from the foreshortening cells 186 at the second end 144 of the stent. In the illustrated embodiment, the anchors are bent so as to be directed generally toward the first end 142 and generally radially outwardly.

The elongate portion of the stent 140 through which the longitudinal struts extend is a nonforeshortening portion 150. The elongate portion of the stent made up of the foreshortening cells comprises a foreshortening portion of the stent. An elongate portion of the stent between the undulating rings 164 and the foreshortening ring 184 is referred to as a transition portion 194.

In a manner as discussed above in connection with other embodiments, when the stent 140 is radially compacted, the length of the longitudinal section will remain substantially constant, but the length of the foreshortening portion will increase. Correspondingly, when radially expanded from a compacted state to the expanded state as shown in FIG. 4A, the length of the foreshortening portion will decrease, while the length of the nonforeshortening portion remains the same.

The stent frame 140 is configured to support a flexible valve body having valve leaflets so as to provide a prosthetic heart valve implant. Preferably the valve body is disposed on the inside of the stent frame. This specification presents multiple stent frame embodiments, which can support valve bodies of multiple shapes and configurations so as to provide valve implants. For ease of illustration, this specification and associated drawings will refer to a stent or implant without necessarily discussing or showing the valve body. However, it is to be understood that valve implants are to include a valve body having leaflets.

In the illustrated embodiment, each of the longitudinal struts bends radially inwardly in the transition portion 194 between the second ring 164*b* and the foreshortening ring 184 so as to define a shoulder 192 along which the outer diameter of the stent lessens. As such, and as shown in FIG. 4A, the diameter of the stent at the first end 142 is greater than the diameter of the stent 140 at the second end 144 when the stent is in the relaxed position. In the illustrated embodiment, the anchors 190 extend radially outwardly sufficient so that tips of the anchors are disposed diametrically about the same as or outwardly from the shoulder. As discussed in U.S. Provisional Application No. 61/169,367, the use of the anchor features on the ventricular side of the stent frame is intended to maximize the stent frame's ability to counteract the high pressures that the atrio-ventricular valves will experience during the systolic portion of the heart's pumping cycle. The bend configuration of the anchor features in this embodiment is different from that shown previously in FIG. 19 in that it does not incorporate the bulge feature and instead has a smaller radius of curvature in the region where the anchor features extend radially outward from the stent frame. A tighter radius in that region is expected to provide further anchoring strength in the axial direction. In addition, this embodiment does not incorporate the additional support struts shown in Section 672 of FIG. 22B.

As discussed in U.S. Provisional Application No. 61/169,367, FIGS. 23A-D show a stent frame 740, similar to stent frame 140 of FIG. 4A, with a larger diameter upper portion 742 and a smaller diameter lower portion 744 with the valve 730 located solely in the upper portion 742 of the stent frame 740. Of the three embodiments described herein in connection with FIGS. 23A-D, 24A-D and 25A-D, this embodiment provides the largest possible effective orifice area for the valve 730. It also minimizes or eliminates foreshortening in the valve region which may provide additional durability in the case of tissue valve materials by reducing any tensile forces that could be acting on the tissue as the stent frame 740 changes diameter during loading and expansion. As shown in the figures of U.S. Provisional Application No. 61/169,367, in some embodiments, the upper portion 742 can have a diameter of 38 millimeters, the lower portion 744 can have a diameter of 32 millimeters and the valve 730 can have a length of 14 millimeters and be tied to the 38 millimeter section sitting in the left atrium.

A variation of this embodiment is shown in FIG. 18 where the stent frame formation 540 and valve 530 location are identical; however in FIG. 18, the height of the valve 530 has been reduced. This allows blood to flow through the stent frame 540 and around the delivery device, which provides intermediate valve functionality when the implant 528 is partially deployed.

As further discussed in U.S. Provisional Application No. 61/169,367, FIGS. 24A-D show a same stent frame 740 formation as previously described in connection with FIGS. 23A-D but with an intra-annular valve 730*b* position. In this configuration, the valve 730*b* is attached to the lower portion 744 of the stent frame 740 resulting in an intra-annular position. As shown in the figures of U.S. Provisional Application No. 61/169,367, in some embodiments, the upper portion 742 can have a diameter of 38 millimeters, the lower portion 744 can have a diameter of 32 millimeters, and the valve 730*b* can have a length of 8 millimeters and tied to the 32 millimeter section. This design minimizes the potential for stagnant blood flow and eliminates any low-flow regions within the left atrium, while still maintaining a single diameter valve.

In a preferred embodiment, the stent frame is initially provided as a circular cross-section nitinol tube. The tube is laser cut according to a pattern corresponding to the struts, cells and the like. The cut tube preferably is electrochemically polished to as to remove rough edges. The cut and polished nitinol tube may be shaped in accordance with a desired manner, such as shaping the anchors to extend radially outwardly, and the nitinol stent frame may be heated-treated to both establish the shape memory and to obtain desired elasticity attributes.

Figure 5A:
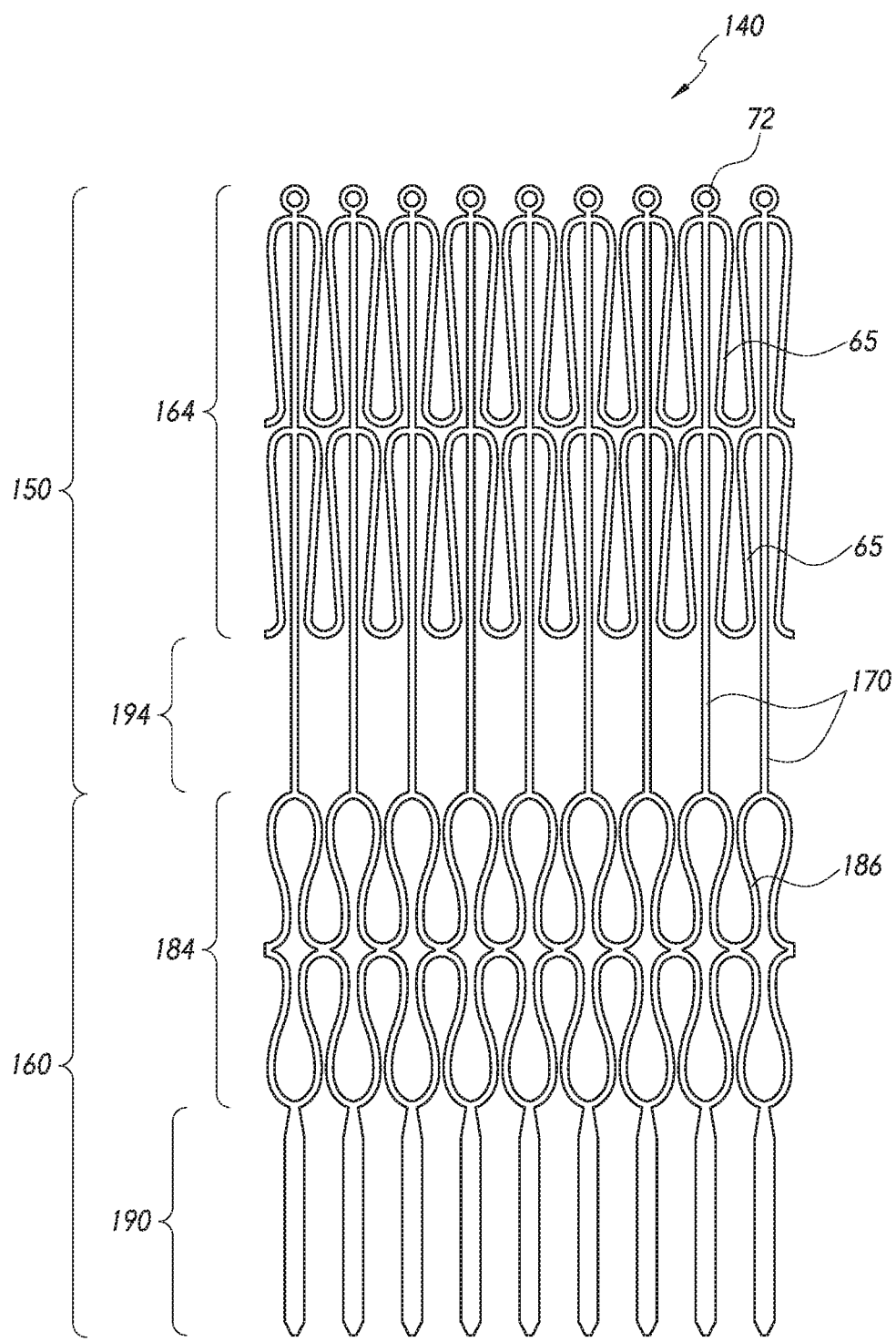
FIG. 5A shows a flat cutting pattern for a stent frame as in FIG. 4A.

With specific reference to FIG. 5A, a flat pattern for laser cutting a nitinol tube to form the stent 140 of FIG. 4A is shown. As indicated, the rings 164 are formed near a first end of the flat pattern and the anchors 190 formed are at an opposite second end of the flat pattern. The rings 164 include the cuts for the undulating struts, and the foreshortening ring 184 includes the cells 186 in a flat configuration. The transition area 194 is shown between the undulating rings 164 and the foreshortening ring 184. Although the stent is initially cut to the pattern shown in FIG. 5A, further shaping and manipulation is performed to form it into the shape shown in FIG. 4A. For example, the stent as a whole is stretched radially, the anchors 190 are bent backwardly, and the longitudinal struts 170 in the transition portion are deformed to form the shoulders 192. The stent is then heat treated, as appropriate, so as to take on the illustrated desired shape as its relaxed shape.

Figure 5B:
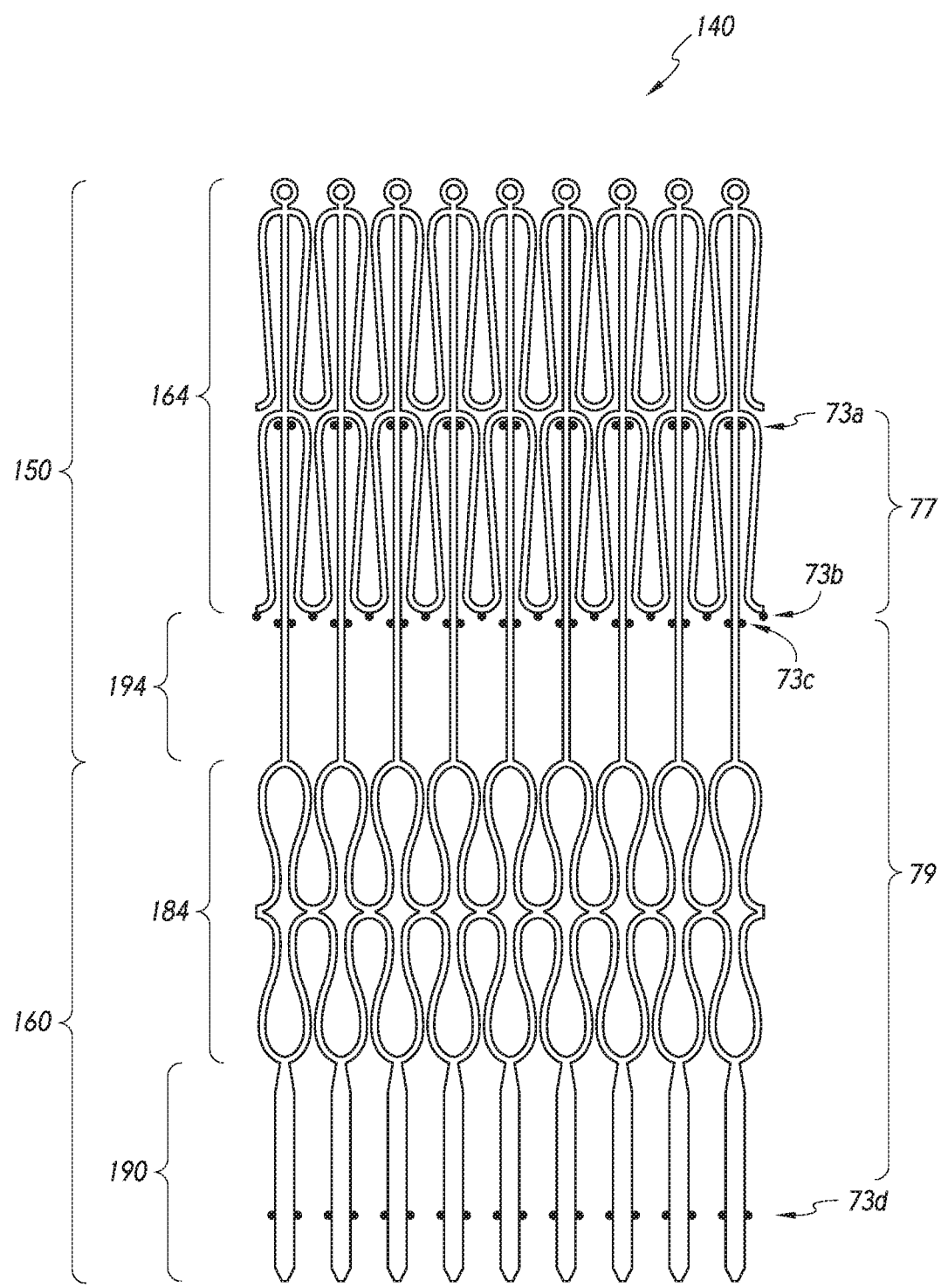
FIG. 5B shows possible eyelet locations within the stent frame to facilitate assembly of the tissue and/or fabric.
Figure 5C:
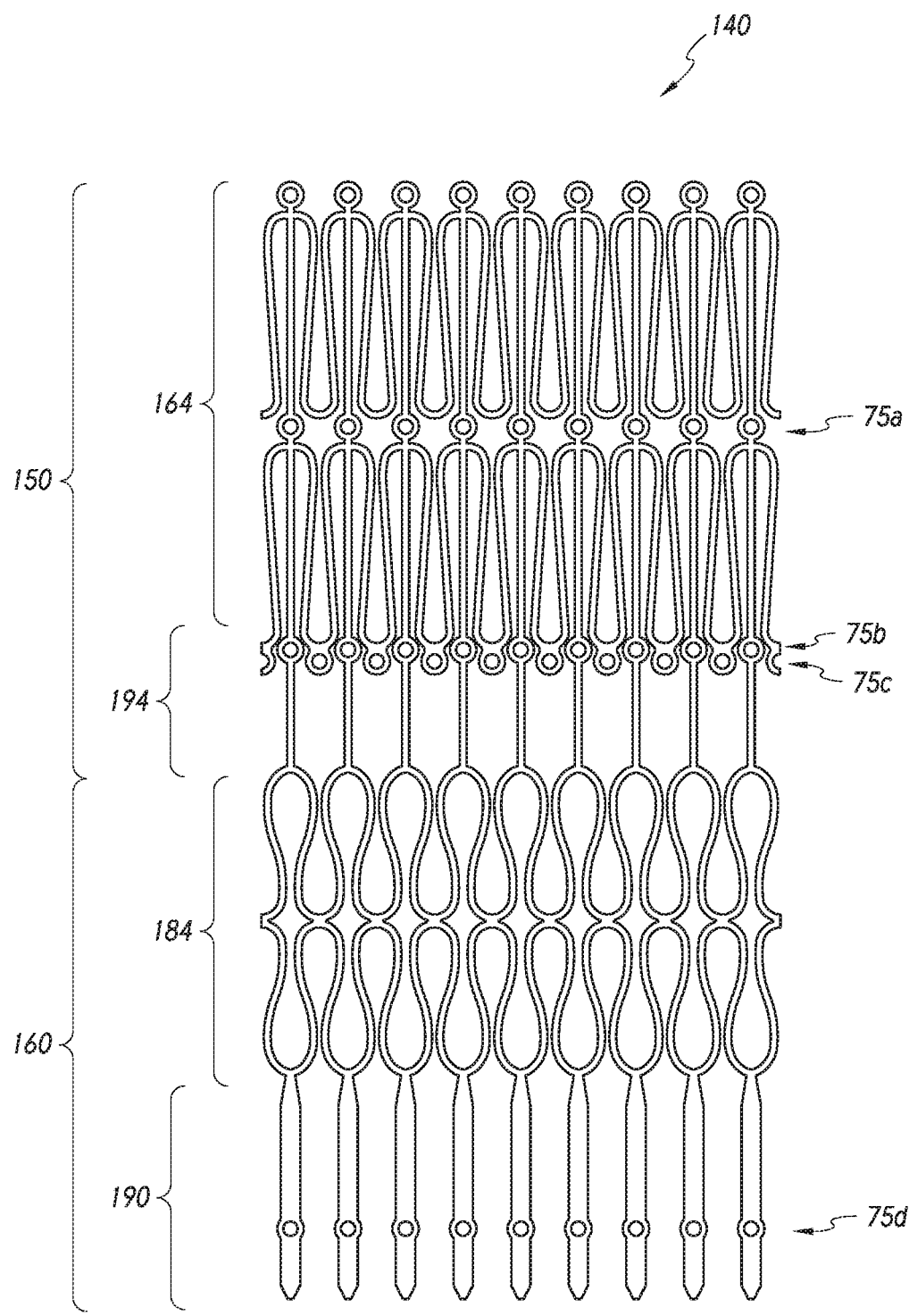
FIG. 5C shows another embodiment of possible eyelet locations within the stent frame to facilitate assembly of the tissue and/or fabric.

As further discussed in U.S. Provisional Application No. 61/169,367, FIGS. 5B and 5C show the flat pattern stent frame geometry with locations for eyelet holes, 73a-d, 75a-d, that will be utilized during the assembly process to attach the valve material and the liner material to the stent frame. FIG. 5B designates potential eyelet locations 73a-d in both the tissue area 77 and the fabric liner area 79 of the stent frame 140. FIG. 5C shows another variation where the eyelet holes 75a-d have been incorporated into the flat pattern stent frame geometry.

In the embodiment illustrated in FIG. 4A, there is no outwardly-extending anchor barb upstream from the anchors 190. Preferably, in practice, the stent 140 is placed so that the valve annulus is captured between the anchors 190 and the shoulder 192. As such, the shoulder 192 and anchors 190 cooperate to hold the stent 140 in place, preventing the stent from being forced either way through the native annulus.

Figure 6:
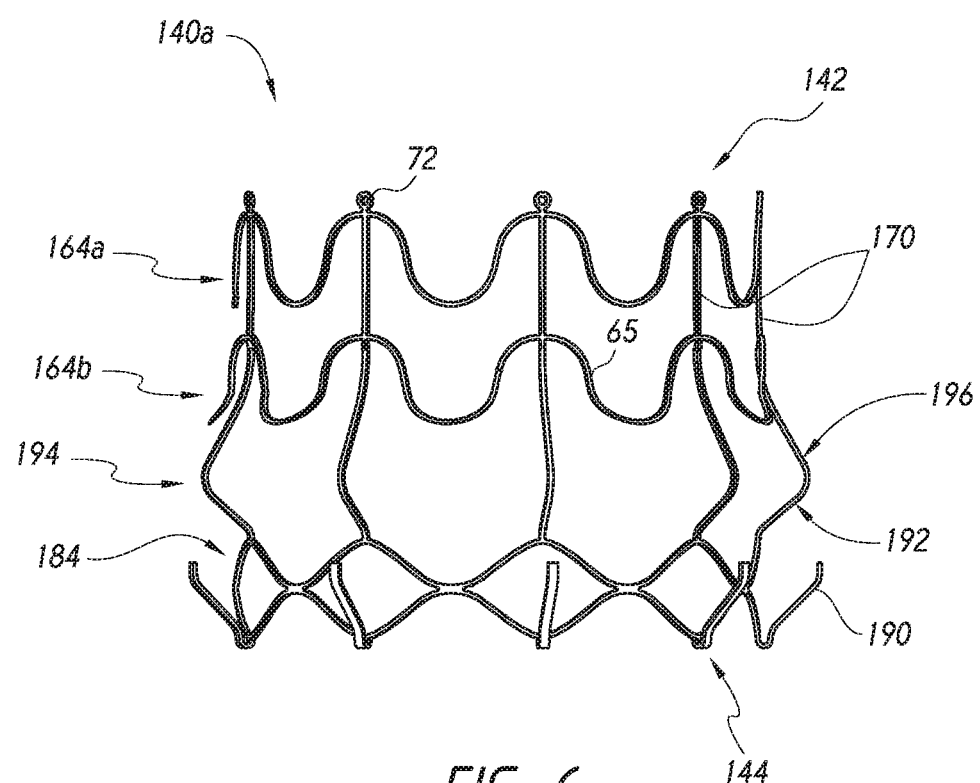
FIG. 6 shows a plan view of a stent frame in accordance with yet another embodiment.

With reference next to FIG. 6, another embodiment of a stent 140a is shown, having structure similar to the stent 140. However, in the transition portion 194 of stent 140a, the longitudinal struts 170 bend along their length to extend radially outwardly, and then bend again to extend radially inwardly so as to define an outward flare 196. In the illustrated embodiment, at least portions of the undulating struts 65 of the second undulating ring 164b take on the curvature of the at least part of the flare 196.

In a manner similar to the embodiment of FIG. 4A, the flare portion 196 of the transition portion 194 effectually creates a shoulder 192. However, in the stent 140a embodiment illustrated in FIG. 6, the diameter at the first end 142 of the stent 140a is substantially the same as the diameter of the stent at the second end 144. Preferably, and in a manner having similarities to the discussion above, during valve deployment, the native valve annulus will be captured in the area between the anchors 190 and the shoulder 192. In a preferred embodiment, the flat cut pattern as illustrated in FIG. 5A can be formed into the shape of stent 140a. Thus, multiple stent shapes can be formed from the same cut pattern.

As discussed in U.S. Provisional Application No. 61/169,367, FIGS. 25A-D show a stent frame 840, similar to stent 140a of FIG. 6, with a smaller diameter upper portion 842, a central flare 843 to provide the transition shoulder, and a smaller diameter lower portion 844 (equal to that of the upper portion 842). Here the upper edge of the valve 830 is attached in the center of the upper portion 842 of the stent frame 840, while the lower edge of the valve 830 and the commissural posts 834 of the interior leaflets are attached in the lower portion 844 of the stent frame 840. This configuration maintains a consistent diameter for the valve 830 while allowing for longer leaflets which could offer improved hemodynamics by minimizing opening and closing angles of the valve leaflets. As shown in the figures of U.S. Provisional Application No. 61/169,367, in some embodiments, the upper portion 842 can have a diameter of 32 millimeters, the outward flare 843 can have a diameter of 38 millimeters, the lower portion 844 can have a diameter of 32 millimeters, and the valve 830 can have a length of 16 millimeters and be tied to the upper and lower 32 mm sections.

There are two options shown for possible anchor features that may be added to the upper section of the stent frame to offer additional fixation. In the atrio-ventricular position, this would correspond to additional fixation on the atrial side of the annulus. With reference to FIG. 7A, yet another embodiment of a stent 140b has a structure much like that of stent 140. However, as shown, an upstream anchor 190b extends from each of the free apices 118 of the second ring 164. Preferably the upstream anchors 190b extend distally past the initial bend of the shoulder 192. As discussed in U.S. Provisional Application No. 61/169,367, in an embodiment, the anchor 190b would extend downward from the supporting struts in the upper section of the stent frame and would be equally spaced between the contact points of the opposing anchor features extending from the lower portion of the stent frame. As noted in U.S. Provisional Application No. 61/169,367, in an embodiment the contact location would be the same radial distance from the edge of the annulus. In this embodiment, during valve deployment, a native annulus preferably is captured between and engaged by the anchors 190, shoulders 192 and upstream anchors 190b. An embodiment of another stent 140d, similar to stent 140b, is illustrated in FIG. 7B in an expanded state and FIG. 7C in a collapsed state.

With reference next to FIG. 8A, still another embodiment of a stent 140c having basic structure very similar to stent 140 of FIG. 4A is illustrated. In the illustrated embodiment, the longitudinal struts 170 bend in a transition portion 194 so as to define a shoulder 192. However, as shown in the illustrated embodiment, at or near the beginning of the inward radial bend, the longitudinal struts each split into three arms 198a, 198b, 190c. First and second arms 198a, b cooperate to define a cell which preferably extends the length of the shoulder 192 from the point of bending to a foreshortening cell 186 of the foreshortening ring 184. A third arm 190c between the first and second arms 198a, b extends from the bend portion toward the second end 144 of the stent 140c and radially outwardly so as to define a strut anchor 190c generally opposing the corresponding downstream anchor 190. As discussed in U.S. Provisional Application No. 61/169,367, in an embodiment, the anchor 190c would extend outward at the start of the transition shoulder 192 and would be aligned with the tips of the opposing anchor features extending from the lower portion of the stent frame. As noted in U.S. Provisional Application No. 61/169,367, in an embodiment the contact location would be the same radial distance from the edge of the annulus. In a manner similar to other embodiments discussed above, during valve placement, preferably a native valve annulus is captured in the space between the downstream anchor 190 and the strut anchor 190c. The stent 140c is held securely in place by the opposing anchors 190, 190c, and shoulder 192. An embodiment of another stent 140e, similar to stent 140c, is illustrated in FIG. 8B in an expanded state and FIG. 8C in a collapsed state.

In the embodiments discussed above, stent frames have been described in which upstream end of the stent has a diameter greater than a downstream end of the stent, and embodiments have been described in which the upstream and downstream ends have substantially the same diameter. It is also to be understood that other stent embodiments may have a downstream end having a greater diameter than an associated upstream end.

In the stent frame embodiments discussed above, the stents are cut from a tube having similarities to the embodiment shown in FIG. 5A, and the anchors are formed during processing by bending the anchor portions backwardly and radially outwardly. It should be understood that a plurality of anchor shapes may be employed as desired. For example, with reference next to FIG. 9A, one embodiment of an anchor 90a comprises a relatively large base radius having a generally "U"-shaped bend. FIG. 9B shows an anchor 90b also having a relatively large base radius but then continuing bending about the radius beyond 180° so as to define a bulged feature before bending again so as to extend toward the first end of the stent. FIG. 9C presents an anchor 90c having a relatively tight base radius leading to an outward bend and then another bend back inwardly so that the anchor tip is directed generally parallel to or slightly outwardly from a longitudinal axis of the stent. FIG. 9D illustrates an anchor 90d with a relatively large base radius leading to an outward bend before bending back inwardly so that the anchor tip is directed generally parallel to or slightly outwardly from a longitudinal axis of the stent. FIG. 9E shows an anchor 90e having a tight base radius that completes only about a 130°-160° turn, and then continues to curve slightly along its length having a very long bending radius so as to approach, but not necessarily complete, a 180° turn at its tip.

In the illustrated embodiment, the tips of the anchors have been shown as generally pointed or flat. It is to be understood that numerous tip configurations can be employed as desired to optimize the engagement and attachment of the replacement heart valve to the native valve annulus. For example, FIG. 10a shows an anchor tip 92a having a smooth radius configured to limit trauma to the tissue. FIG. 10b illustrates an embodiment of an anchor tip 92b having an expanded ball radius. Such a ball radius can be created as a two-dimensional circular shape during the laser cutting process, or can be a three-dimensional sphere attached to the anchor tip during, for example, a ball welding procedure. FIG. 10c shows a pointed anchor tip 92c configured to provide some degree of penetration into the tissue of the valve annulus. FIG. 10d illustrates a flared anchor tip 90d configured to distribute anchor forces over a surface area of tissue, but also comprising a serrated edge to penetratingly engage such tissue. In additional embodiments a flared tip may have a smooth edge. Additionally, further tip configurations can be employed as desired to optimize engagement and fixation for different valves and different disease morphologies. In further embodiments, as noted in Provisional Application No. 61/169,367 different tip configurations can be combined within a single stent frame to further optimize engagement and fixation as needed.

Figure 11A:
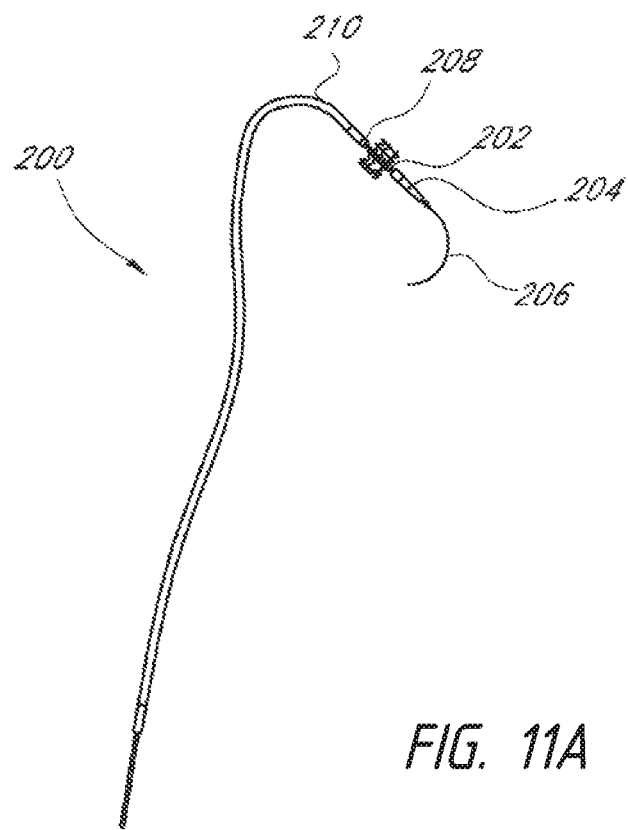
FIG. 11A shows an embodiment of a delivery device for delivering a valve implant in accordance with one embodiment.
Figure 11B:
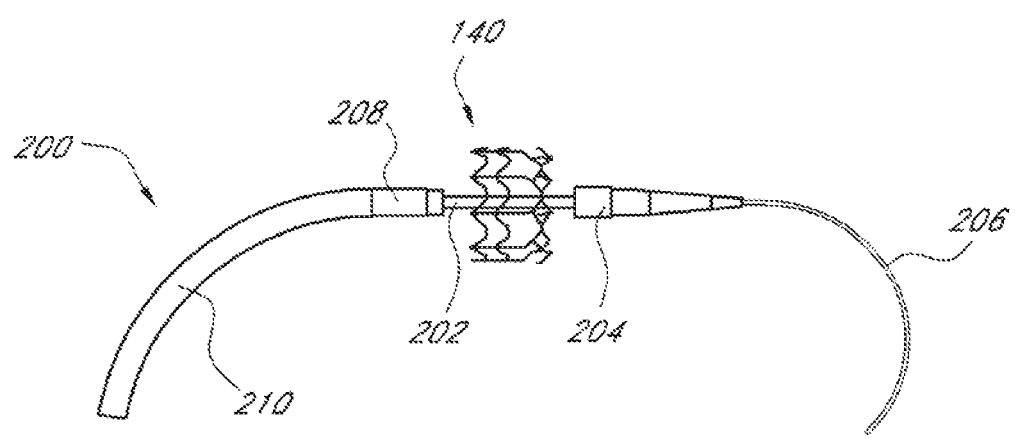
FIG. 11B shows a distal portion of the delivery device of FIG. 11A.
Figure 11C:
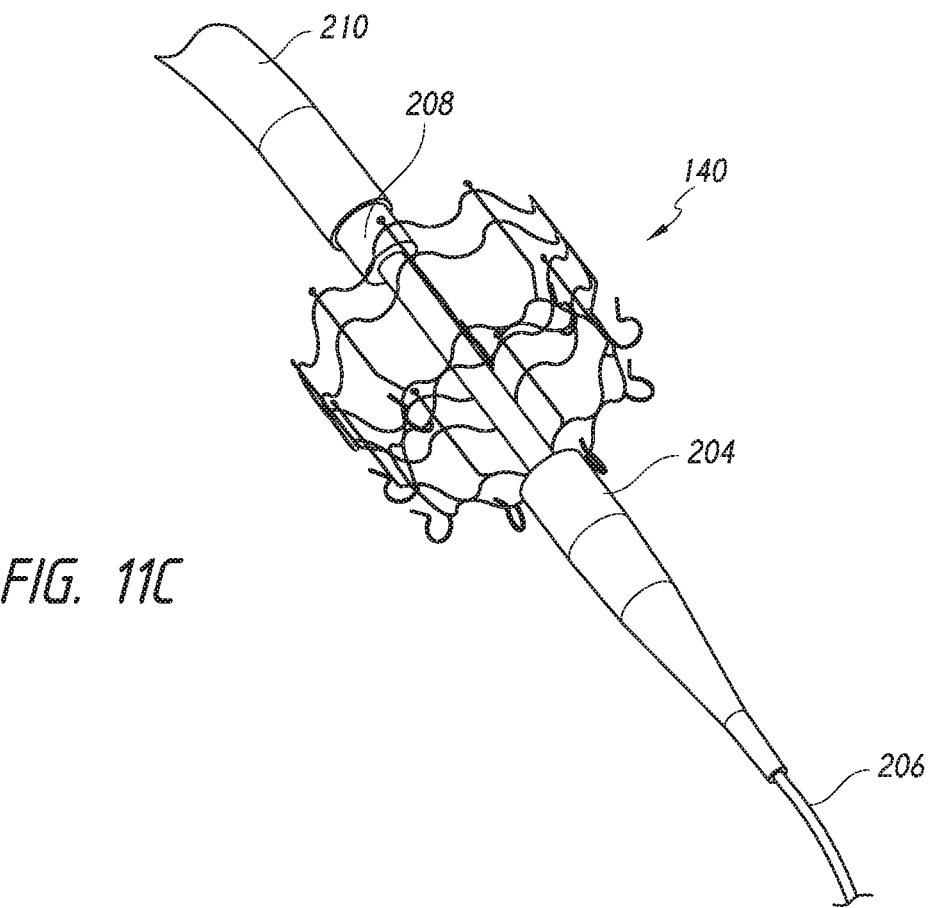
FIGS. 11C-11D show several views of one embodiment of the delivery catheter.
Figure 11D:
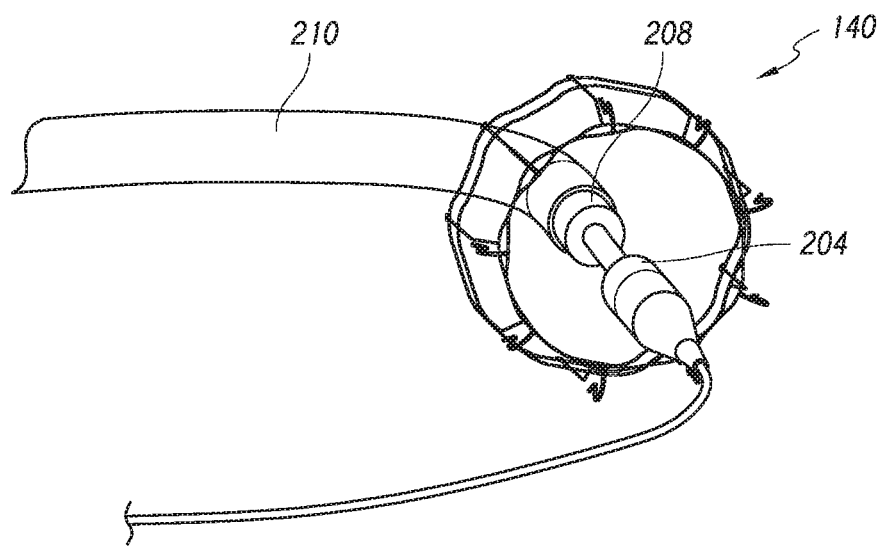

The embodiments as disclosed above in connection with replacement heart valves can be delivered to a patient's heart valve annulus in various ways, such as by open surgery, minimally-invasive surgery, and percutaneous, or transcatheter, delivery through the patient's vasculature. With reference next to FIGS. 11A and 11B, an embodiment of a delivery device 200 is shown in connection with a replacement heart valve. The illustrated embodiment comprises an elongate, steerable delivery catheter configured to be advanced through a patient's vasculature in a percutaneous delivery approach. The illustrated device 200 comprises an elongate inner tube 202 that is attached at its distal end to a nose cone 204. The inner tube 202 has a lumen sized and configured to slidably accommodate a guidewire 206 so that the device 200 can be advanced over the guidewire 206 through the vasculature. A support tube 208 concentrically encircles the inner tube 202 and is sized to be slidable over the inner tube. An outer sheath 210 is disposed so as to be slidable over the support tube 208. In the illustrated embodiment, and preferably, in a manner as discussed in embodiments presented below, the support tube 208 and outer sheath 210 cooperate to grasp onto an end of the replacement heart valve, which, for ease of illustration, is here represented by showing only a stent frame. For delivery, the valve is compacted and held within the outer sheath 210. As noted in Provisional Application No. 61/169,367, the device shown here represents a percutaneous or trans-catheter embodiment of the delivery device. In a surgical or minimally-invasive embodiment, the components would remain the same, however, the overall length of the system would be shorter and flexibility of the sheath and tube components may or may not be required.

Figure 12G:
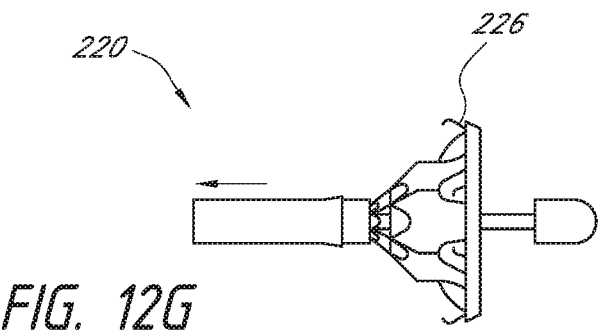
Figure 12H:
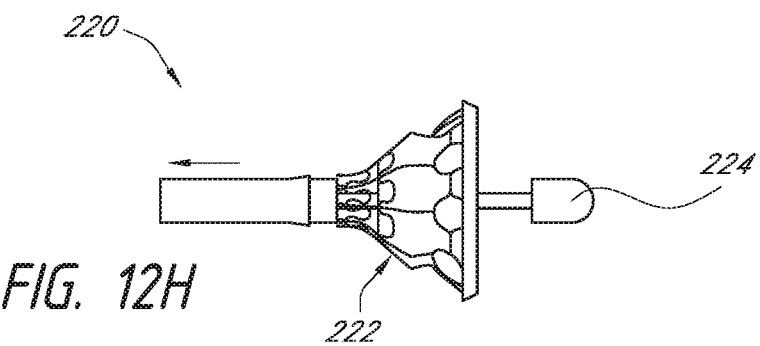
Figure 12I:
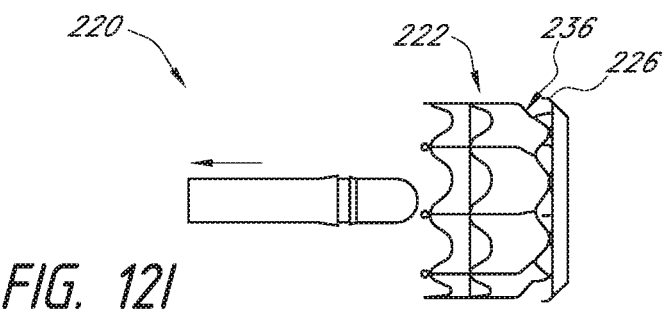
Figure 13A:
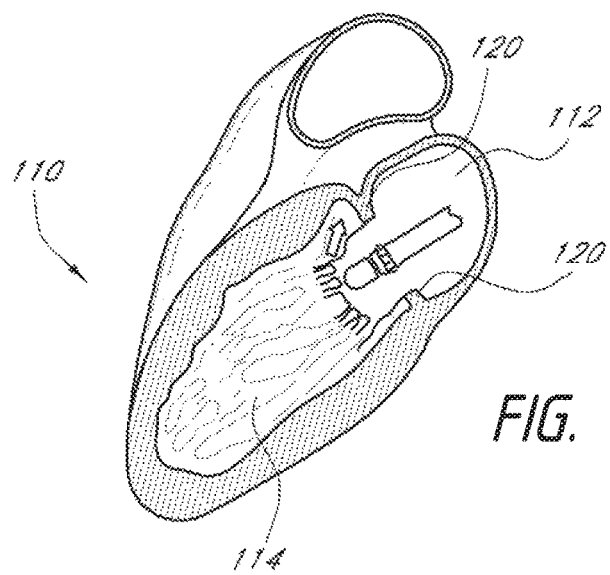
FIGS. 13A-C show the delivery device of FIGS. 12A-I at selected stages of the deployment operation in connection with a human heart.
Figure 13B:
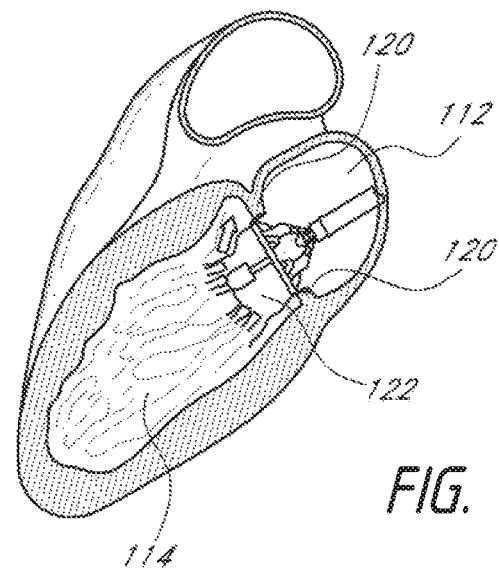
Figure 13C:
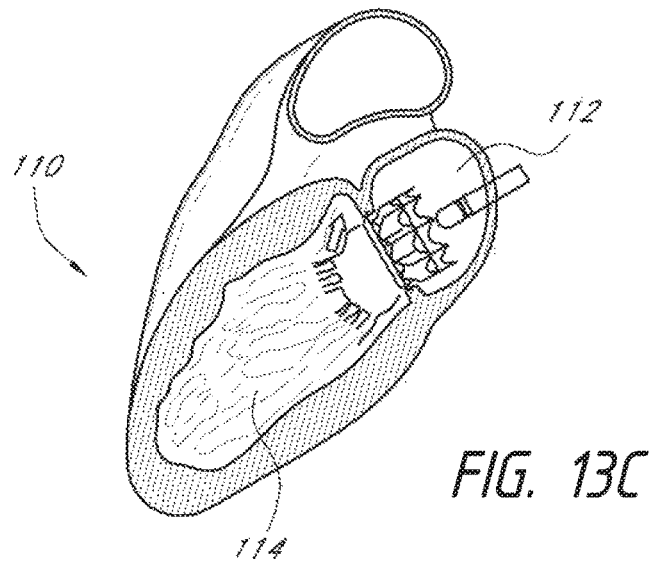

With reference next to FIGS. 12 and 13, delivery device 220 configured in accordance of one embodiment is shown at various steps along a sequence or method of valve implant deployment. More specifically, FIGS. 12A-12I demonstrate schematic views of various steps of a deployment process, and FIGS. 13A-13C show the state of the delivery device 220 relative to a native heart valve annulus 120 at certain stages of deployment. In the embodiment illustrated in FIG. 13, the deployment device 220 deploys the heart valve implant 222 into a patient's native mitral annulus 120. It is to be understood, however, that features and aspects as discussed herein may be employed when employing valves elsewhere in a patient's heart or other vasculature.

With specific reference to FIG. 13A, in use preferably the delivery device 220 is advanced into the patient's heart 110 so that a distal end including a nose cone 224 passes through the diseased native valve and through the native annulus 120. As such, the delivery device 220 preferably is positioned so that the anchor portions 226 of the valve implant 222, though still compacted within an outer sheath 230, are disposed generally on a side of the native annulus opposite an approach direction. Once the delivery device 220 is in place, and as next depicted in FIG. 12A, the outer sheath 230 begins to be retracted thereby exposing the distal, or anchor end 232, of the valve implant 222. In the illustrated embodiment, barb-shaped anchors 226 are disposed at the anchor end 232. It is to be understood that other embodiments may employ other anchor structures. As the outer sheath 230 continues to be retracted as shown in FIG. 12B, more of the stent 222 is exposed and the anchor end of the stent begins to expand radially as progressively shown in FIGS. 12B, C and D. However, and as more particularly shown in FIG. 12D, a proximal end 234 of the stent frame 222 is still held securely within the outer sheath 230, preferably by the outer sheath cooperating with a support tube so as to restrain the proximal end 234 of the stent 222 from being released from the delivery device 220. Nevertheless, since the distal portion 232 of the stent has been substantially released it is free to expand and, in the embodiment shown in FIG. 12D, the distal end 232 of the stent can expand to its fully expanded state while the proximal end of the stent remains restrained within the outer sheath.

With additional reference now to FIG. 13B, when the distal end 232 is fully expanded a slight back pressure preferably is applied to the entire delivery device 220 so as to pull the stent 222 proximally and seat the implant 222 and particularly the anchor features 226, against the native annulus. In the illustrated embodiment, the anchor features 226 are seated against the subvalvular side of the initial annulus 120. Proper seating of the implant can be confirmed via tactile feedback, external imaging, and/or other suitable methods.

With continued reference to FIGS. 12 and 13, if, for example, data indicates that the placement of the stent frame 222 should be modified, such as due to improper seating, alignment, engagement or the like. The implant 222 can be at least partially resheathed and repositioned. For example, with particular reference to FIGS. 12E and 12F, since the implant has not been fully deployed from the outer sheath 230, the outer sheath 230 can be moved distally, thus engaging and compacting the stent frame so as to force it back into the outer sheath. Such compaction will remove the implant 222 from its faulty positioning. The implant can then be repositioned and redeployed in a new position by again moving the outer sheath 230 proximally as depicted in FIG. 12G.

Once it is determined that the implant 222 is correctly seated, with the anchors 226 disposed as desired in the subvalvular side of a native annulus, the implant can be completely released from the delivery device 220. Preferably, and with reference next to FIG. 12H, such complete release comes when the outer sheath 230 continues to be retracted proximally, exposing the proximal end 230 of the stent frame 222 and disengaging the locking mechanism between the stent frame, support tube and outer sheath. As such, the entire stent becomes free of any constraint by the delivery device and expands freely as depicted in FIGS. 12I and 13C so that the implant is fully deployed at the native annulus.

As shown in FIG. 13C, preferably a foreshortening portion of the stent 222 is generally aligned with the native annulus 120 so that the annulus is captured between the anchor features 226 and an opposing anchor feature such as a shoulder portion of the stent. Of course, in other embodiments, other configurations of anchoring portions may or may not include a shoulder, may include upstream and downstream anchors, and/or may include other structure for engaging one or both sides of an annulus. Once the implant is fully deployed, preferably the sheath is again moved distally to re-engage the nose cone, and the delivery device is removed from the patient.

In the embodiment discussed and illustrated in connection with FIGS. 12 and 13, only a distal portion of the delivery device 220 is shown. It is to be understood that such a distal portion may be employed in multiple delivery device configurations. For example, a percutaneous, transcatheter-approach delivery device such as shown in FIGS. 11A and 11B can employ a distal portion similar to that in the embodiment shown in FIGS. 12 and 13. Also, delivery devices for us in minimally-invasive or even open surgical procedures may have similar structure and similar operation principles although such devices may advantageously have some different mechanical properties such as increased stiffness, than do embodiments used in trans-catheter approaches.

Figures 14A, 14B:
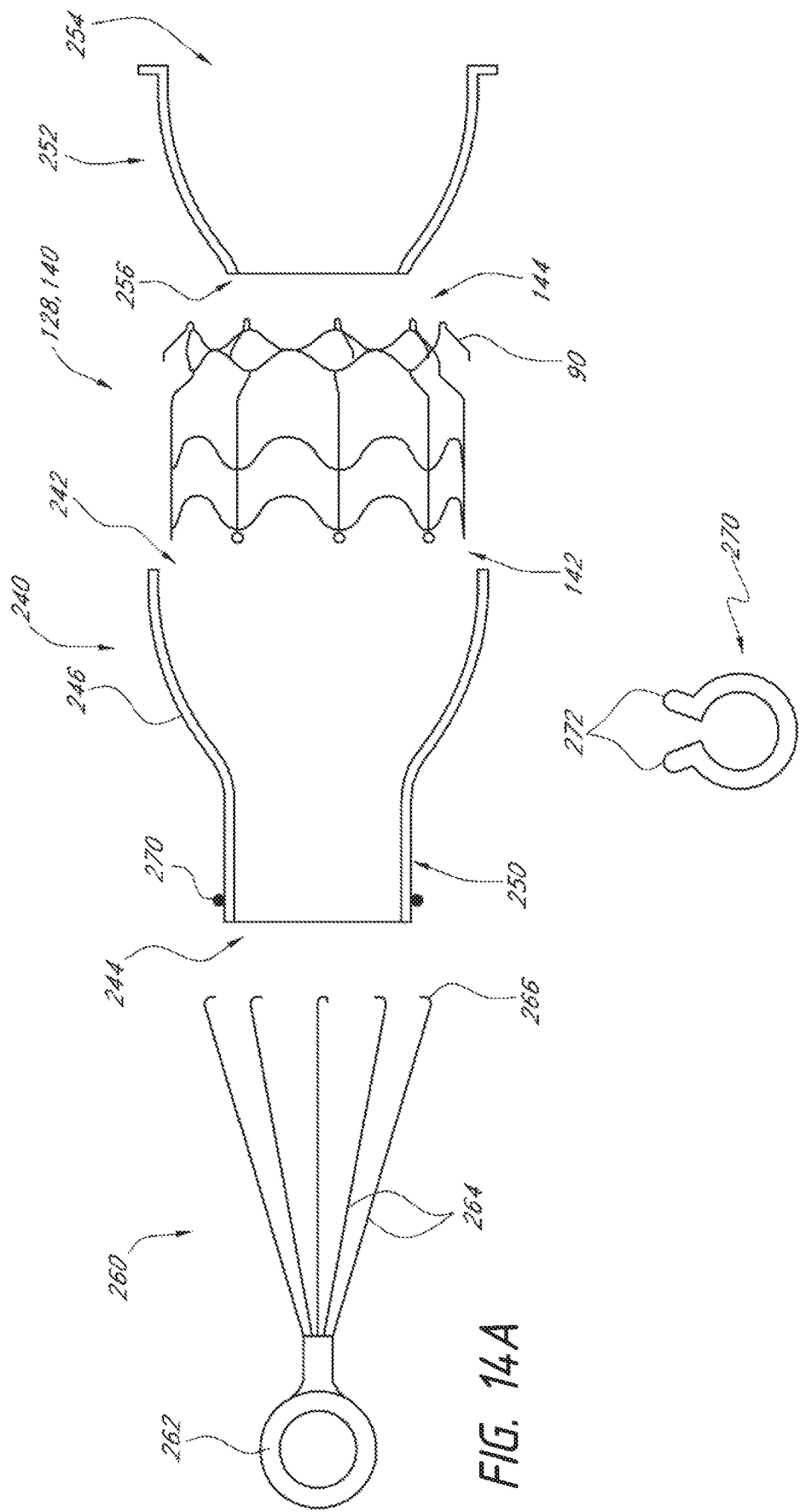

With reference next to FIGS. 14A-14L, an embodiment of a delivery device 238 and a method and apparatus for loading a heart valve implant 128 onto the delivery device is shown. With reference first to FIG. 14A, the loading apparatus comprises a compacting device 240 which, in the illustrated embodiment, is generally funnel-shaped. The funnel 240 is elongate and comprises a first and second end 242, 244. The first end 242 has a comparatively large diameter and the second end 244 has a comparatively small diameter. A transition 246 progressively decreases the diameter between the first and second ends. Preferably, an elongate compaction portion 250 is disposed at and adjacent second end 244. Preferably, the diameter within the compacted portion 250 is generally constant along its length and approaches or matches the diameter of the second end 244.

A cap 252 is provided and is shaped to fit through the first or large end 242 of the funnel 240. Preferably an outer surface of the cap 252 is configured to fit generally complementarily against the inner surface of the funnel 240. A first end 254 of the cap 252 is configured to fit generally onto and hook onto the first end 242 of the funnel. A second end 256 of the cap 252 is configured to fit within the funnel and preferably proximal of the compacting portion 250 of the funnel 240. The second end of the cap preferably comprises a blocking structure.

With continued reference to FIG. 14A, an example heart valve 128 is shown. In the illustrated embodiment, the heart valve comprises the stent frame 140 described above in connection with FIG. 4A. To aid in simplicity of illustration, only the stent frame, and not the valve body, is shown. It is to be understood, however, that in practice preferably a completely assembled heart valve implant is employed. Additionally, it is to be understood that implants and stents having configurations other than the specifically shown implant can make use of a compacting apparatus and delivery device having features in accordance with the features and principles discussed in connection with this embodiment. However, this structure and method are particularly preferred in connection with implants having self-expanding stents.

As shown in FIG. 14A, preferably, the first end 242 of the funnel 240 has a diameter large enough to accommodate the fully expanded, at rest stent frame 140. Further, preferably, the stent frame is positioned so that its first end 142, at which the locking members 72 are disposed, is facing toward the funnel. In the illustrated embodiment, the locking members comprise eyelets. Other structures may be employed in other embodiments.

A pull member 260 or "octopus" preferably comprises a pull ring 262 that is connected to a plurality of elongate arms 264. Each of the arms preferably terminates in a hook 266 or other securing member that is configured to engage one of the locking members/eyelets 72. Preferably, there are the same number of arms 264 as there are eyelets 72. Additionally, preferably the arms are substantially flexible so as to appropriately distribute forces and to obtain secure purchase on the stent frame. In one embodiment, the arms 264 comprise a suture material, although various types of string and even semi-rigid plastics, wires or the like may be employed.

With additional reference to FIG. 14B, an O-ring 270 is preferably disposed about the compacting portion 250 of the funnel 240 and generally adjacent the second end 244 of the funnel. In the illustrated embodiment, the O-ring 270 is an inwardly biased broken ring shape having a pair of tabs 272 adjacent the break in the ring. The tabs assist in placing the ring over the compacting portion 250 of the funnel and other side manipulating the O-ring. Preferably, the O-ring 270 is configured so that its at-rest position is at a diameter substantially less than the diameter of the compaction portion.

With reference next to FIG. 14C, in operation preferably the octopus arms 264 are threaded through the open second end 244 of the funnel, out the first end 242 of the funnel, and engaged with the implant 128 so that each octopus hook 266 connects to one of the eyelets 72, on the stent frame 140. The pull ring 262 is then pulled so as to pull the implant into and through the first end of the funnel. As the pull ring continues to be pulled distally, the stent engages the inner surface of the funnel at the transition 246 and is forced to be radially compacted as the stent 140 is pulled through the funnel 240 until it is substantially compacted within the compaction portion 250 of the funnel and with the locking members 72 of the stent frame extending out of the second end of the funnel as shown in FIG. 14D.

With continued reference to FIG. 14D, once the implant has been pulled into the compaction portion 250 of the funnel so that the locking member portions of the frame are exposed and extend out of the second end of the funnel, the cap 252 preferably is inserted through the first end of the funnel so that its second end 256 is generally adjacent the second end 144 of the stent frame. The blocking structure at the second end of the cap 252 preferably is configured to prevent the stent frame from moving backwards out of the funnel. For example, the cap may have a thickness that substantially blocks such backwards movement. Other structures such as partial or full blocking of the funnel may also be employed. With the cap in place, the octopus arms are disengaged from the locking members as shown in FIG. 14E.

With reference next to FIG. 14F, additional structure of the delivery device is illustrated in connection with the funnel 240 and implant 128 in the configuration of FIG. 15E. As shown, the delivery device 238 comprises an elongate inner tube 274 that is connected to a nose cone 276. Preferably, the inner tube 274 has a lumen sized and adapted to accommodate a standard guidewire 278 extending therethrough. The nose cone 276 preferably has a generally atraumatic tip portion 280 at its distal end and has a cavity 282 formed in its proximal end. A circumferential skirt 284 extends from the proximal end of the nose cone 276 and an inner surface 286 of the circumferential skirt 284 defines the cavity 282.

An elongate support tube 290 has a lumen sized and configured to slidably accept and slide over the inner tube 274. A locking mechanism 292 comprising a plurality of locking features 294 is disposed adjacent a distal end of the support tube 290. In the illustrated embodiment, the locking features comprise bosses 294 extending radially outwardly from an outer surface of the support tube. The illustrated bosses 294 are sized and shaped to generally matingly fit the eyelets of the stent frame 140.

An outer sheath 300 is configured to fit slidably over the support tube 290. The outer sheath 300 has a thickness defined between an outer surface 302 and an inner surface 304. A diameter of a lumen of the outer sheath is defined by the inner surface 304 and preferably the lumen diameter 75 such that the inner surface just clears the locking bosses 294 of the support tube, as will be discussed and shown in more detail below. A raised portion 306 of the outer sheath 300 is disposed near but spaced from a distal end of the outer sheath, and a seat 308 is defined on the distal end of the raised portion 306. As will be discussed in more detail below, the raised portion and seat 308 are configured to engage a proximal end of the nose cone circumferential skirt 284.

Although the delivery device has just been introduced in connection with FIG. 14F, it is to be understood that, in some embodiments, the funnel is threaded over the delivery device so that the funnel concentrically surrounds the inner tube and is disposed between the nose cone and the support tube before the heart valve implant is loaded into the funnel. Thus, in some embodiments, preferably the heart valve is loaded into and compacted within the funnel while the funnel is already disposed over the inner tube of the delivery device.

With reference next to FIG. 14G, with the implant loaded into the compaction portion of the funnel, the support tube 290 preferably is advanced distally so that the eyelets 72 of the implant 140 are generally aligned with the bosses 294 of the support tube. However, in the illustrated embodiment, the diameter of the compaction portion 250 of the funnel is greater than the diameter of the support tube 290, and thus the eyelets 72 are disposed radially outwardly from the bosses 294. With reference next to FIG. 14H, preferably the inwardly biased O-ring 270 is slipped off of the end of the funnel and onto the exposed connecting portions of the stent frame so as to urge the eyelets inwardly and into engagement with the aligned bosses. The implant is thus connected to the support tube 220.

With reference next to FIG. 14I, with the eyelets 72 and bosses 294 engaged, the outer sheath is then advanced distally over the support tube 290 so that the distal end of the outer sheath extends over and distally past the bosses. As discussed above, the lumen diameter of the outer sheath is chosen so that the inner surface 304 just clears the bosses 294 of the support tube. Thus, when the outer sheath is moved distally past the bosses when the bosses are engaged with the eyelets 72, the eyelets are captured between the outer sheath 300 and support tube 290, and the first end of the stent is securely held by the support tube. With the eyelets now fully captured, the O-ring is removed.

With reference next to FIG. 14J, the outer sheath 300 continues to be moved distally relative to the support tube 290 and attached implant 140. In the illustrated embodiment, the outer sheath inner diameter is less than the diameter of the funnel compaction portion. Thus, as the outer sheath is moved distally, it progressively radially compacts the heart valve implant. As the implant is progressively compacted within the outer sheath, the funnel 240 preferably is also moved distally so that the implant is progressively transferred from being contained within the funnel to being contained within the outer sheath 300. Eventually, the funnel is completely removed from the implant and the outer sheath contains the implant from its first to its second end, as shown in FIG. 14K.

In the embodiment illustrated in FIG. 14K, the stent frame 140 of the implant has anchors 190 extending radially outward at the second end 144. Those anchors are not captured within the outer sheath in this embodiment, although the outer sheath preferably captures substantially the rest of the stent frame therewithin.

With the implant captured in the outer sheath, the funnel preferably can be removed from the delivery device. In the illustrated embodiment, the smallest diameter portion of the funnel is greater than the outer diameter of the nose cone. Thus, the funnel can be removed by moving it distally over the nose cone. In other embodiments, the funnel may have a lesser diameter than the nose cone, and can be moved by other means such as by cutting the funnel. In still other embodiments, the funnel can have a multiple piece and/or hinged construction and may be held closed by a releasable clamp, clip, or the like. As such, once it has served its purpose and the implant is transferred to the outer sheath, the funnel can be disassembled and/or opened and removed without necessarily drawing the funnel over the nose cone.

With reference next to FIGS. 14K and 14L, with the funnel removed and the implant substantially captured within the outer sheath 300, the nose cone 276 is pulled proximally until as shown in FIG. 14L, the skirt portion 284 of the nose cone engages and compacts the anchors 190, and eventually the proximal end of the nose cone skirt engages the seats 308 defined on the raised portion of the outer sheath. The anchors 190 are thus secured between the nose cone skirt inner surface 286 and the outer sheath outer surface 302. The implant is thus fully contained within the delivery device 238 which preferably maintains a substantially contiguous outer surface. The implant may be delivered to a native heart valve annulus in a manner having similarities to the embodiment discussed above in connection with the FIGS. 12 and 13.

In the embodiment discussed above in connection with FIG. 14, the nose cone 276 is depicted as rigidly attached to the inner tube 274. In another embodiment, the nose cone may be selectively detachable from the inner tube so that the valve implant can be independently drawn into a funnel compaction apparatus, without the funnel being mounted over the delivery device. Thus, a loaded funnel as depicted in FIG. 14E can be advanced over an inner tube, and then the nose cone may be attached to the inner tube. In such an embodiment, the funnel may have a smaller diameter than as shown and discussed above, as the funnel is not necessarily of large enough diameter to be drawn over the nose cone, and instead the nose cone may be removed in order to remove the funnel. In fact, in such an embodiment and in some options of such an embodiment, the nose cone is not attached to the inner tube until after the funnel is removed and the implant is substantially captured within the outer sheath.

With reference next to FIGS. 15A-H further embodiments of a device for loading a heart valve implant 128 onto a delivery device 238 are shown. For ease of illustration, the same implant 128/stent frame 140 used in connection with the embodiment described in FIG. 14 is employed, as well as other similar structures, such as the pull member 260, and delivery device 238 structure such as the inner tube 274, nose cone 278, support tube 290 and outer sheath 300.

Figure 15A:
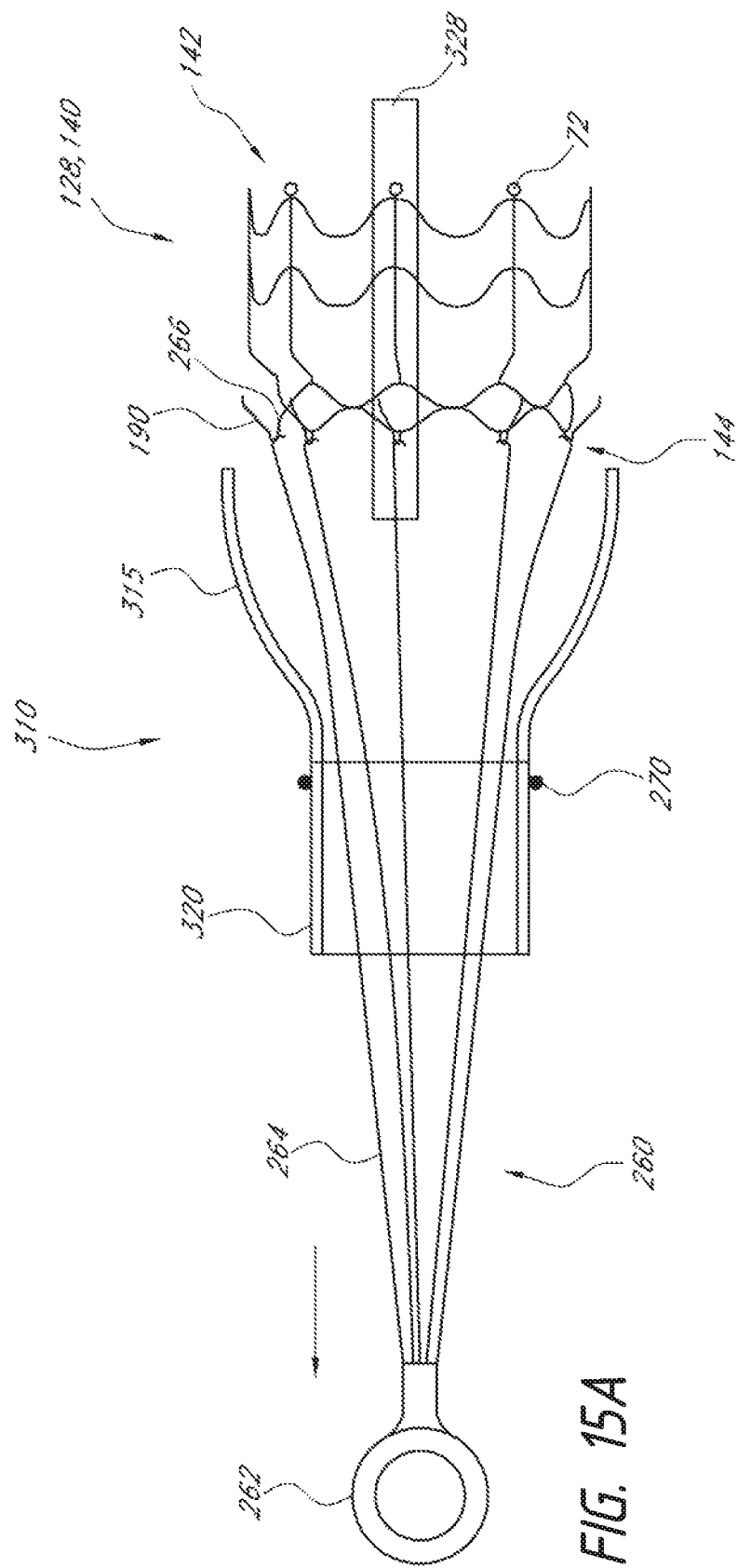

With particular reference to FIG. 15A, the illustrated embodiment comprises a two-piece compaction device 310 comprising a funnel portion 315 and a loading tube portion 320. Preferably, the funnel portion 315 and the loading tube portion are detachably connected to one another. Further, preferably the loading tube portion 320 is elongate and has a substantially constant diameter. As with other embodiments, preferably the octopus arms 264 of the pull member 260 extend through the compaction device 310 to hook onto and engage portions of the implant 128, 140. In the illustrated embodiment, the hooks 266 engage the stent 140 at the second end 144 of the stent.

Figure 15B:
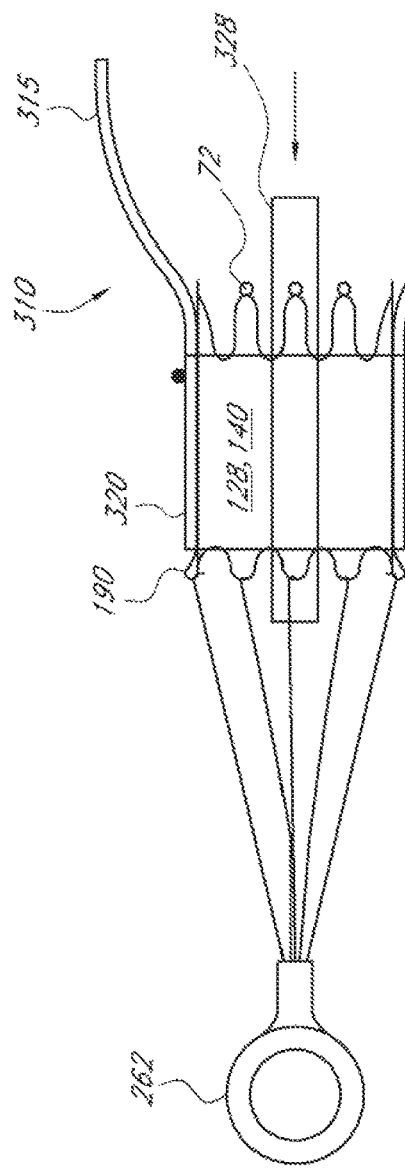

In practice, the pull ring 262 is pulled so as to pull the stent into the compaction device and through the funnel portion 315 to radially compact the stent 140. Preferably, however, a loading inner tube 328 is arranged concentrically within the stent 140 as it is being compacted. As shown in FIG. 15B, the implant 128, 140 eventually is radially compacted within the loading tube 320 and concentrically surrounding the loading inner tube 328. As shown in FIG. 15B, preferably the loading tube 320 has a length that is somewhat less than the total length of the stent 140 when the stent is in its compacted arrangement. As such, at least the eyelets 72 of the first end 142 extend beyond an end of the loading tube 320.

Figure 15C:
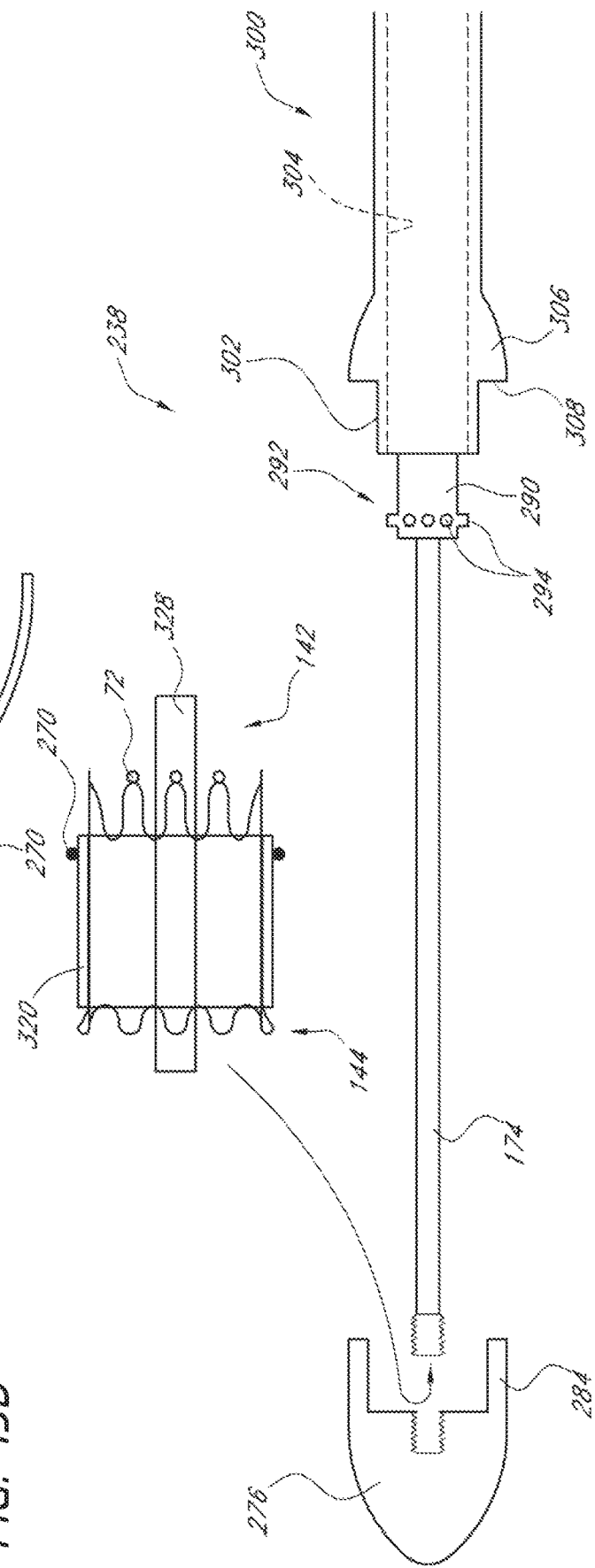
Figure 15F:
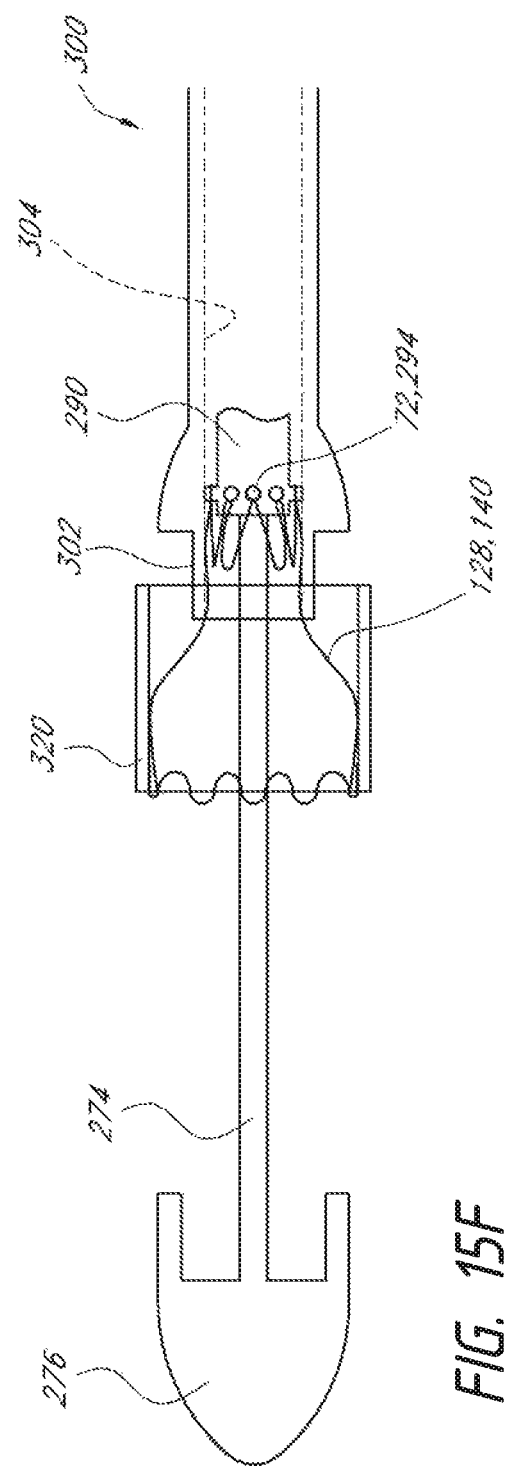

With reference next to FIG. 15C, once the implant 128 is compacted within the loading tube 320, the pull member 260 may be detached from the implant and the loading tube may be detached from the funnel portion 315 so that the loading tube end associated compacted stent 140 and inner loading tube 328 can be independently moved and manipulated.

FIG. 15C shows an embodiment in which the delivery device 238 is configured so that the nose cone 276 can be releasably detached from the inner tube 274. Preferably, the inner loading tube 328 defines an inner lumen having a diameter greater than the outer diameter of the inner tube 274 so that the inner loading tube can be threaded over the inner tube so as to place the compacted implant 128, 140 on the delivery device 238 between the nose cone 276 and the support tube 290. In another embodiment, the nose cone is not detachable from the inner tube. Thus, in order to get the compacted implant disposed on the delivery device 238, the implant is threaded onto the inner tube 274 before the support tube 290 and outer sheath 300 are threaded over the inner tube 274.

In either case, however, once the support tube 320 with its accompanying compacted implant are threaded over the inner tube 274 as desired, the inner loading tube preferably is removed from within the compacted implant and removed from the delivery device. For example, in the embodiment illustrated in FIG. 15C, the loading inner tube 328 can be removed distally off the end of the inner tube 274 when the nose cone 276 is detached. In other embodiments, the loading inner tube 328 can be slid off of the inner tube 274 before the support tube 290 and outer sheath 300 are advanced over the inner tube 274. As such, and as shown in FIG. 15B, the loading tube 320 with its attendant compacted implant 128, 140 is disposed on the inner tube 274 between the nose cone 276 and the support tube 290.

With reference next to FIGS. 15E-15H, preferably the delivery device 238 is then manipulated and operated in a manner similar to that as discussed above in connection with FIGS. 14G-K so as to capture the first end 142, and more specifically the eyelets 72, of the stent frame 140 within the outer sheath 300 using a method of apparatus including the support tube 290 and bosses 294, although other configurations of locking mechanisms 292 may be employed as desired.

With specific reference next to FIG. 15G, in one embodiment, after the implant has been captured within the outer sheath 300, the loading tube portion 320 preferably is removed from around the delivery device 238. In the embodiment illustrated in FIG. 15G, the loading tube 320 can be moved proximally over the outer sheath 300 as the outer sheath engages the nose cone 276. In the embodiment illustrated in FIG. 15H, the loading tube 320 is advanced distally so as to be removed over the nose cone 276 as the outer sheath also is distally to engage the nose cone 276.

In the illustrated embodiments, the loading tube 320 has a lumen diameter sufficiently large so that it can be removed over the nose cone 276, or at least clear the raised portions 306 of the outer sheath 300. In other embodiments, however, the loading tube may have a lumen diameter more closely approaching the inner diameter of the outer sheath lumen. Removal of the loading tube 320 after the implant is sheathed within the outer sheath 300 may involve breaking or cutting the loading tube 320 or, in other embodiments, the loading tube comprises multiple pieces that can be disassembled or opened so as to remove the tube from the delivery device 238.

In one of the embodiments discussed above, the nose cone is detachable from the inner tube. It should be understood that, in one such embodiment, the nose cone is not reattached to the inner tube until after the compacted stent is at least partially pulled into the outer sheath, and the loading tube is removed from the delivery device 238. As such, in this embodiment, the loading tube can have a lumen diameter less than an outer diameter of other structures of the delivery device.

In the embodiments discussed above, an inwardly-biased O-ring 270 is employed to urge locking members 72 of the stent into engagement with locking bosses 294 of the support tube 290. It is to be understood, however, that other methods and structures can be employed to engage the locking members of the stent with the support tube. For example, a user can manually urge the locking members into engagement with the bosses. Additionally, other structures, such as a belt, specially-configured clamping pliers, or the like can be employed to urge the locking members into engagement with one another. It is contemplated that yet further structures can be employed for this purpose.

Figures 16A, 16B:
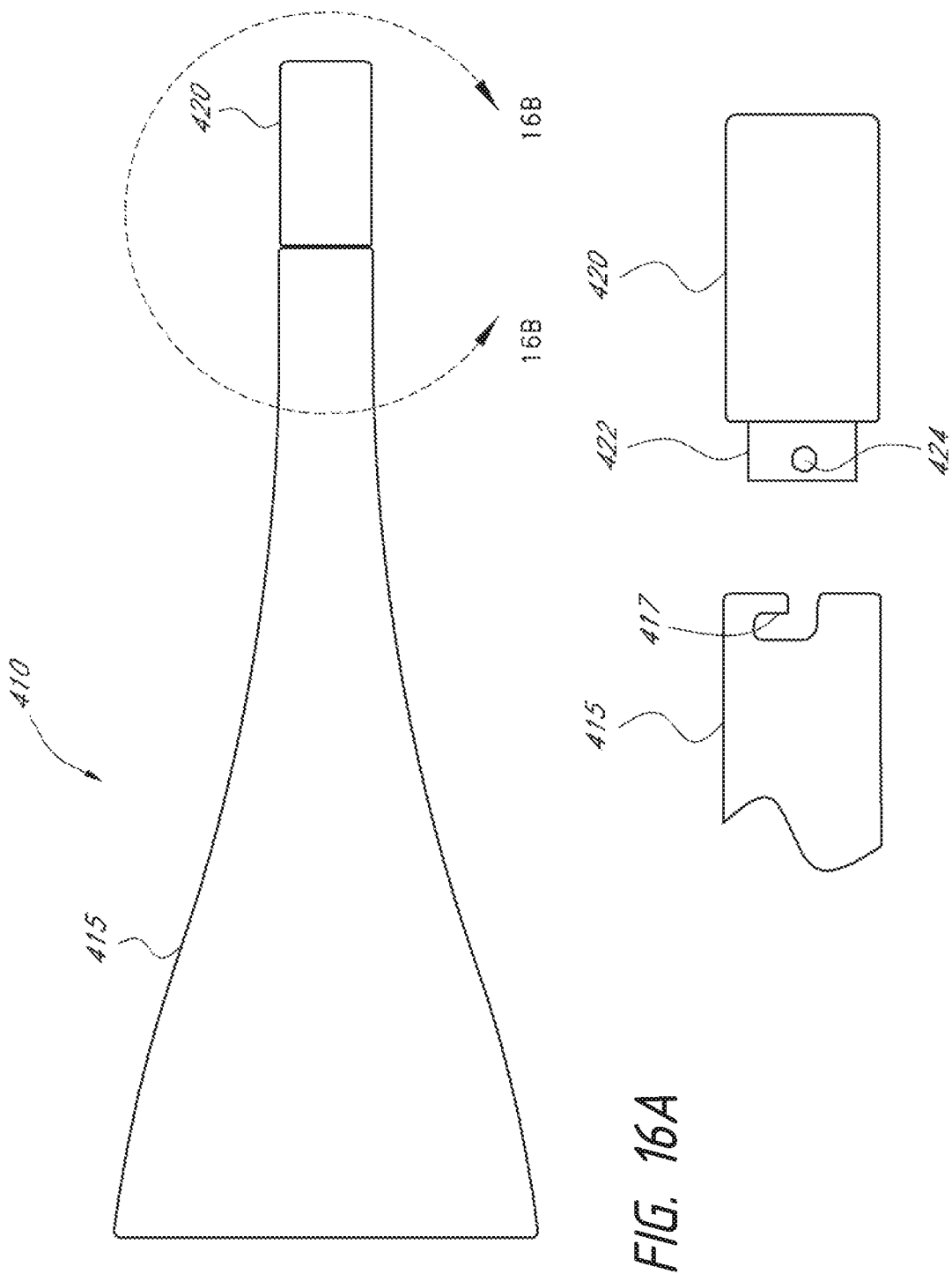
FIGS. 16A and 16B show an embodiment of a multi-piece loading device in an assembled and a disassembled configuration.

With reference next to FIGS. 16A and 16B, another embodiment of a multi-piece compaction device 410 comprises a funnel portion 415 and an elongate load tube 420 that are detachably connected to one another. The funnel portion and load tube preferably share at least some features with other embodiments discussed in this specification. In the illustrated embodiment, the smaller end of the funnel portion comprises an L-lock track 417 formed therein. The load tube 420 comprises an overlap portion 422 having a lock member 424. A diameter of the overlap portion 422 is reduced so that the overlap portion will fit within the end of the funnel portion 415 at the L-lock track 417. The lock member 424 is slidable within the track 417 so as to detachably secure the funnel portion 415 and load tube 420 together. It is to be understood that other structures can be employed to detachably connect the funnel and load tube.

With reference next to FIGS. 17A-G, in another embodiment, an implant 400 is provided in which longitudinal struts 406 terminate in locking member 404 at a non-anchoring end of the stent 400. The illustrated locking members 404 have a generally arrowhead-type shape that is enlarged relative to the adjacent strut 406. Preferably a pull member 260a engages the stent 400 and pulls it through the compaction device 410 so that the implant 400 is compacted within the load tube 420. The load tube and implant can then be removed from the pull member 260a and funnel portion 415 and loaded onto an inner tube 274a of a delivery device.

With particular reference to FIG. 17B, the delivery device preferably includes the inner tube 274a, which is attached to a nose cone 276a. A support tube 430 is slidably disposed over the inner tube, and an outer sheath 300a is slidably disposed over the inner tube. Preferably an inner lumen diameter of the outer sheath 300a is greater than, but very close to, an outer diameter of the support tube 430. A locking mechanism 432 is provided at the distal end of the support tube 430. The locking mechanism 432 preferably comprises a tapered surface 434 that leads to a circumferential capture slot 440. A plurality of guide slots 444 are provided and configured to generally align with struts 406 of the implant 400. Preferably, the load tube 420 is sized such that the radially compacted implant 400 has an outer diameter less than an outer diameter of a proximal ridge of the tapered surface 434 immediately adjacent the capture slot 440.

To load the compacted implant 400, the support tube 430 is advanced so that the tapered surface 434 engages and deflects the locking members 404 and associated struts 406 of the implant 400, as shown in FIG. 17C. The support tube 430 continues to be advanced until the deflected locking members 404 clear the proximal edge of the tapered surface 434, at which point the locking members 404 are no longer deflected, and will spring into the capture slot 440, preferably with an audible "click". When properly aligned, the struts 406 correspondingly spring into the guide slots 444 as depicted in FIG. 17D, and the stent 400 and support tube 430 are now engaged.

With reference next to FIG. 17E, the outer sheath 300a is next advanced distally so as to cover the capture slot 440 and thus securely capture the locking members 404 within the sheath 300a. As the sheath 300a continues to be advance distally, the compacted implant is transferred from the load tube 420 to the sheath 300a. Preferably a distal end of the sheath engages an end of the load tube 420 during such advancement, and thus anchor members that may in some embodiments be biased radially outwardly can be effectively transferred from within the load tube 420 to within the sheath 300a.

With additional reference to FIG. 17F, preferably the nose cone 276a is sized so that the load tube 420 can be slid thereover and removed from the delivery device. In the illustrated embodiment the distal end of the sheath 300a at least partially overlaps the nose cone, and the sheath is shaped to provide a smooth transition from the distal end of the sheath to the nose cone. Of course, other embodiments may employ other structural interaction between the outer sheath and the nose cone, which may in some embodiments be removable.

In practice, the illustrated delivery device has operational features that may be similar to other embodiments discussed herein. For example, the implant can be partially deployed, but resheathed for repositioning. If necessary, the implant can also be resheathed for removal from the patient. In some such embodiments, in the event of complete resheathing, radially-outwardly-biased anchor members may not be able to be completely recaptured within the outer sheath 300a in the same position as originally provided. However, continued advancement of the sheath 300a after engagement of the anchor can have the effect of bending the anchor backwardly (distally) so that it is effectively captured between the sheath and nose cone. The delivery device can then be further manipulated, and even removed from the patient, with the entire implant, including anchor portions, fully resheathed.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. In fact, the embodiments specifically disclosed herein have been used as a vehicle to describe certain inventive features that can be employed alone or in various combinations in multiple additional embodiments. Thus, it is contemplated that various combinations or subcombinations of the specific features and aspects of the embodiments may be made and still fall within the scope of the invention. For example, support tube embodiments such as in FIG. 14 can be modified to capture locking members within a capture slot as disclosed in FIG. 17, and vice versa. Further, even though the stents described herein have been configured to foreshorten, certain features such as the methods and apparatus for controlled delivery as discussed in connection with FIGS. 12 and 13, can be employed with self-expanding stents that don't necessarily foreshorten, and don't necessarily have anchoring features comparable to the embodiments disclosed herein. Further, the delivery device depicted in FIGS. 12 and 13 can be replaced with delivery devices employing principles as discussed in FIG. 14, 15, 17 or the like. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

The invention claimed is:

1. A system for replacing a native valve, the system comprising:
a replacement valve comprising:
an expandable frame having a proximal and a distal end and configured to transition between a compacted configuration and an expanded configuration;
a plurality of distal anchors each extending from the expandable frame at an attachment point, wherein when the expandable frame is in the expanded configuration:
at least a portion of each distal anchor extends proximally towards a proximal end of the expandable frame; and
a proximalmost portion of each distal anchor is positioned radially outward from the expandable frame;
an anchoring component positioned proximal of the attachment point, the anchoring component comprising an enlarged portion of the expandable frame, the enlarged portion having a diameter greater than diameters of the proximal and distal ends of the expandable frame when the expandable frame is in the expanded configuration; and
a locking component extending from the expandable frame; and
a delivery device comprising:
an elongate inner tube having a locking structure configured to receive and engage the locking component;
a cover configured to surround the locking structure and the locking component when the locking component is engaged with the locking structure.

2. The system of claim 1, wherein the enlarged portion is monolithic with the expandable frame.

3. The system of claim 1, further comprising a valve body connected to the expandable frame.

4. The system of claim 1, wherein the proximalmost portion of each of the distal anchors is proximal to the attachment point.

5. The system of claim 1, wherein the proximalmost portion of each of the distal anchors extends substantially parallel with a longitudinal axis of the expandable frame.

6. The system of claim 1, wherein the proximalmost portion of each of the distal anchors is atraumatic.

7. The system of claim 1, wherein the replacement valve is a replacement atrio-ventricular valve.

8. The system of claim 7, wherein the replacement valve is a replacement mitral valve.

9. The system of claim 1, wherein the locking structure comprises a capture slot configured to engage with the locking component.

10. The system of claim 9, wherein the locking structure comprises a plurality of guide slots configured to engage with the locking component, wherein each of the plurality of guide slots is distal to the capture slot.

11. The system of claim 1, wherein the cover is configured to move with respect to the locking structure.

12. A system for replacing a native valve, the system comprising:
a replacement valve comprising:
an expandable frame having a proximal and a distal end and configured to transition between a compacted configuration and an expanded configuration;
a plurality of distal anchors each extending from the expandable frame at an attachment point, wherein when the expandable frame is in the expanded configuration:
at least a portion of each distal anchor extends proximally towards a proximal end of the expandable frame; and
a proximalmost portion of each distal anchor is positioned radially outward from the expandable frame; and
an anchoring component positioned proximal of the attachment point, the anchoring component comprising an enlarged portion of the expandable frame, the enlarged portion having a diameter greater than diameters of the proximal and distal ends of the expandable frame when the expandable frame is in the expanded configuration; and
a locking component extending from the expandable frame;
a delivery device comprising:
a capture slot configured to engage the locking component;
a guide slot distal to the capture slot, the guide slot configured to engage the locking component;
a cover configured to surround the capture slot, the guide slot, and the locking component when the locking component is engaged with the capture slot and the guide slot.

13. The system of claim 12, wherein the replacement valve is a replacement atrio-ventricular valve.

14. The system of claim 13, wherein the replacement valve is a replacement mitral valve.

15. The system of claim 12, further comprising a valve body connected to the expandable frame.

16. The system of claim 12, wherein the cover is configured to translate with respect to the guide slot and the capture slot.

17. A system for replacing a native valve with a replacement valve, the system comprising:
a self-expandable tubular stent having a plurality of anchors extending from a distal end portion, an enlarged shoulder portion located along an intermediate portion, and a plurality of locking struts extending from a proximal end portion;
a valve body supported within the tubular stent; and
a delivery device comprising an inner tube having guide slots sized to receive the plurality of locking struts and an outer sheath adapted for maintaining the plurality of locking struts in the guide slots during delivery, the outer sheath being retractable for releasing the plurality of locking struts from the guide slots during implantation at the native valve;
wherein, after implantation, the plurality of anchors are positioned radially outwardly of the stent on a downstream side of the native valve annulus and the shoulder is positioned on an upstream side of the native valve annulus such that the native valve annulus is captured between the anchors and the shoulder; and
wherein the valve body replaces the function of the native valve.

18. The system of claim 17, wherein the replacement valve is a replacement atrio-ventricular valve.

19. The system of claim 18, wherein the replacement valve is a replacement mitral valve.

20. The system of claim 17, wherein the plurality of anchors comprise atraumatic tips.

\* \* \* \* \*